(12) United States Patent
Zeitlmann et al.

(10) Patent No.: US 9,067,888 B2
(45) Date of Patent: Jun. 30, 2015

(54) INHIBITORS OF PROTEIN KINASES

(71) Applicant: Ingenium Pharmaceuticals GmbH, Martinsried (DE)

(72) Inventors: Lutz Zeitlmann, Munich (DE); Andre Niestroj, Sennewitz (DE); Ulrich Heiser, Halle/Saale (DE)

(73) Assignee: AstraZeneca AB, Molndal (SE)

( * ) Notice: Subject to any disclaimer, the term of this patent is extended or adjusted under 35 U.S.C. 154(b) by 0 days.

(21) Appl. No.: 14/011,057

(22) Filed: Aug. 27, 2013

(65) Prior Publication Data

US 2013/0345233 A1   Dec. 26, 2013

Related U.S. Application Data

(62) Division of application No. 12/932,955, filed on Mar. 10, 2011, now Pat. No. 8,518,948.

(60) Provisional application No. 61/339,866, filed on Mar. 10, 2010.

(51) Int. Cl.
| | |
|---|---|
| C07D 401/12 | (2006.01) |
| C07D 213/72 | (2006.01) |
| A61K 31/444 | (2006.01) |
| C07D 213/75 | (2006.01) |
| C07D 401/14 | (2006.01) |
| C07D 409/12 | (2006.01) |
| C07D 417/12 | (2006.01) |

(52) U.S. Cl.
CPC ............ *C07D 213/72* (2013.01); *C07D 213/75* (2013.01); *C07D 401/12* (2013.01); *C07D 401/14* (2013.01); *C07D 409/12* (2013.01); *C07D 417/12* (2013.01)

(58) Field of Classification Search
None
See application file for complete search history.

(56) References Cited

U.S. PATENT DOCUMENTS 5,886,191 A   3/1999   Dominguez et al.

FOREIGN PATENT DOCUMENTS

| EP | 0254322 A1 | 1/1988 |
|---|---|---|
| EP | 1679309 A1 | 7/2006 |
| FR | 2878247 A1 | 5/2006 |
| WO | WO 01/62233 A2 | 8/2001 |
| WO | WO 02/074742 A2 | 9/2002 |
| WO | WO 02/081445 A1 | 10/2002 |
| WO | WO 02/094825 A1 | 11/2002 |
| WO | WO 02/100401 A1 | 12/2002 |
| WO | WO 02/102790 A1 | 12/2002 |
| WO | WO 2004/084824 A2 | 10/2004 |
| WO | WO 2005/003123 A1 | 1/2005 |
| WO | WO 2005/005438 A1 | 1/2005 |
| WO | WO 2005/012262 A1 | 2/2005 |
| WO | WO 2005/012298 A1 | 2/2005 |
| WO | WO 2005/026129 A1 | 3/2005 |
| WO | WO 2005/027902 A1 | 3/2005 |
| WO | WO 2005/103022 A1 | 11/2005 |
| WO | WO 2007/136790 A2 | 11/2007 |
| WO | WO 2007136790 A2 * | 11/2007 |
| WO | WO 2009/047359 A1 | 4/2009 |
| WO | WO 2009/140519 A1 | 11/2009 |
| WO | WO 2010/053861 A2 | 5/2010 |
| WO | WO 2010/101849 A1 | 9/2010 |

OTHER PUBLICATIONS

Blain et al., The Journal of Biological Chemistry, vol. 272, No. 41(10), pp. 25863-25872 (1997).*
LuValle et al., Frontiers in Bioscience 5, pp. 493-503 (May 2000).*
Traxler, Expert Opinion on Therapeutic Patents, 7(6), pp. 571-588, 1997.*
Ali A et al., Chembiochem 2009, 10, 2072-2080.
Bain J et al., Biochem J 2007, 408, 297-315.
Barboric M et al., Mol Cell 2001, 8, 327-337.
Baumli S et al., EMBO J 2008, 27, 1907-1918.
Brower V, Nat Biotechnol 2000, 18, 387-391.
"Design of Prodrugs", ed. H. Bundgaard, Elservier, 1985.
Cohen P et al., Nat Rev Drug Discov 2004, 3, 479-487.
Dai Y and Grant S, Current Opinion in Pharmacology 2003, 3, 362-370.
Eguchi T et al., Mol Cancer Ther 2009, 8, 1460-1472.
Falco GD et al., Oncogene 2002, 21, 7464-7470.
Feldmann and Maini, Nat Med 2003, 9, 1245-1250.
Filgueria De Azevedo W Jr, Biochem Biophys Res Commun 2002, 293(1), pp. 566-571.
Ghose AK et al., J Med Chem 2008,51, 5149-5171.
Hooper C et al., J Neurochem 2008, 104, 1433-1439.
Huang HC et al., Curr Drug Targets 2006, 7, 1389-1397.
Huwe a et al., Angew Chem Int Ed Engl 2003, 42, 2122-2138.
Jope RS et al., Curr Drug Targets 2006, 7, 1421-1434.
Jope RS et al., Neurochem Res 2007, 32, 577-595.
Juhaszova M et al., Circ Res 2009, 104, 1240-1252.
Karaman MW et al., Nat Biotechnol 2008, 26, 127-132.

(Continued)

*Primary Examiner* — Zinna Northington Davis
(74) *Attorney, Agent, or Firm* — Olson & Cepuritis, Ltd.

(57) ABSTRACT

Compounds of general Formula (I):

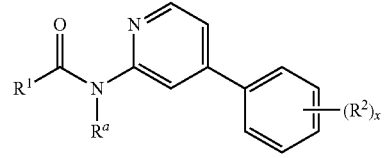

Formula (I)

wherein $R^1$, $R^2$, $R^3$, $R^a$, A, B and x are as defined herein are inhibitors of protein kinases in particular members of the cyclin-dependent kinase family and/or the glycogen synthase kinase 3 family and are useful in preventing and/or treating any type of pain, inflammatory disorders, cancer, immunological diseases, proliferative diseases, infectious diseases, cardiovascular diseases, metabolic disorders, renal diseases, neurologic and neuropsychiatric diseases and neurodegenerative diseases.

13 Claims, No Drawings

(56) References Cited

OTHER PUBLICATIONS

Knoeckaert M et al., Trend Pharmacol Sci 2002, 23, 417-425.
Krug M and Hilgeroth A, Mini Rev Med Chem 2008, 8, 1312-1327.
Lee et al., Europ J Neurosci 2004, 3375-3381.
Lee J et al., Diabetes Res Clin Pract 2007, 77, Suppl 1, S 49-S 57.
Leitch A, Haslett C and Rossi A, Br J Pharmacol 2009, 158, 1004-1016.
Liu H and Hermann CH, J Cell Physiol 2005, 203, 251-260.
Luo J et al., Cancer lett 2009, 273, 194-200.
MacAulay K et al., Expert Opin Ther Targets 2008, 12, 1265-174.
MacLachlan TK et al., J Cell Biochem, 1998, 71 467-478.
Mannig G et al., Science 2002, 298, 1912-1934.
Martinez A, Med Res Rev 2008, 28, 773-796.
Protective Groups in Organic chemistry, ed. MCOMIE JFW, Plenum Press, 1973.
Meijer L et al., Pharmacol Ther 1999, 82, 279-284.
Morgan DO, Ann Rev Cell Dev Biol 1997, 13, 161-291.
Nasmyth K, Science 1996, 274, 1643-1677.
O'Hare M et al., Pharmacol Ther 2002, 93, 135-143.
Obligado SH et al., Kidney Int 2008, 73, 684-690.
O'Brien WT et al., Biochem Soc Trans 2009, 37 (Pt 5), 1133-1138.
Rayasam GV et al., Br J Pharmacol 2009, 156, 885-898.
Sausville EA, Trends Molec Med 2002, 8, S32-S 37.
Wang D et al., J Virol 2001, 75, 7266-7279.
West MJ et al., Journal of Virol 2001, 75, 8524-8537.
Wyatt PG et al., J Med Chem 2008, 51, 4986-4999.
Zhang J et al., Nat Rev Cancer 2009, 9, 28-29.
Zhou M et al., J Virol 2004, 78, 13522-13533.

\* cited by examiner

INHIBITORS OF PROTEIN KINASES

CROSS REFERENCE TO RELATED APPLICATIONS

This application is a division of U.S. patent application Ser. No. 12/932,955, filed on Mar. 10, 2011 now U.S. Pat. No. 8,518,948, which claims benefit of U.S. Provisional Application. No. 61/339,866, filed Mar. 10, 2010, each of which is incorporated herein by reference in its entirety.

FIELD OF THE INVENTION

The present invention relates to inhibitors of protein kinases, in particular members of the cyclin-dependent kinase family and/or the glycogen synthase kinase 3 family, and therapeutic applications thereof. Furthermore, the invention relates to methods of preventing and/or treating any type of pain, inflammatory disorders, cancer, immunological diseases, proliferative diseases, infectious diseases, cardiovascular diseases, metabolic disorders, renal diseases, neurologic and neuropsychiatric diseases and neurodegenerative diseases comprising the administration of an effective amount of at least one inhibitor described herein.

BACKGROUND OF THE INVENTION

Cyclin-dependent protein kinases ("CDKs") constitute a family of well-conserved enzymes that play multiple roles within the cell, such as cell cycle regulation and transcriptional control (Nasmyth, K., Science 1996, 274, 1643-1677; Morgan, D. O., Ann. Rev. Cell Dev. Biol. 1997, 13, 261-291).

Some members of the family, such as CDK1, 2, 3, 4, and 6 regulate the transition between different phases of the cell cycle, such as the progression from a quiescent stage in G1 (the gap between mitosis and the onset of DNA replication for a new round of cell division) to S (the period of active DNA synthesis), or the progression from G2 to M phase, in which active mitosis and cell division occur. Other members of this family of proteins, including CDK7, 8, and 9 regulate key points in the transcription cycle, whereas CDK5 plays a role in neuronal and secretory cell function.

CDK complexes are formed through association of a regulatory cyclin subunit (e.g., cyclin A, B1, B2, D1, D2, D3, and F) and a catalytic kinase subunit (e.g. cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

CDK9 in association with its cyclin partners (cyclin T1, T2a, T2b, or K) constitutes the catalytic component of the positive transcription elongation factor b (P-TEFb) protein complex that functions during the elongation phase of transcription by phosphorylating the carboxyl-terminal domain (CTD) of the largest subunit of RNA polymerase II. P-TEFb acts in concert with positive transcription factors as well as negative regulatory factors of RNA transcription, thus overcoming a block of transcriptional elongation (Liu, H., and Herrmann, C. H., J. Cell Physiol. 2005, 203, 251-260). Flavopiridol analogues that selectively inhibit P-TEFb were described recently (Ali, A. et al., Chembiochem. 2009, 10, 2072-2080).

It is known that cell-cycle dysregulation, which is one of the cardinal characteristics of neoplastic cells, is closely associated with genetic alteration and deregulation of CDKs and their regulators, suggesting that inhibitors of CDKs may be useful as therapeutics for proliferative diseases, such as cancer. Thus, small molecule inhibitors targeting CDKs have been the focus of extensive interest in cancer therapy (Dai, Y., and Grant, S., Current Opinion in Pharmacology, 2003, 3, 362-370; Zhang, J. et al., Nat. Rev. Cancer 2009, 9, 28-39). The ability of inhibiting cell cycle progression suggests a general role for small molecule inhibitors of CDKs as therapeutics for proliferative diseases, such as cancer. Recently, inhibition of CDK9/cyclin T function was also linked to prevention of HIV replication and the discovery of new CDK biology thus continues to open up new therapeutic indications for CDK inhibitors (Sausville, E. A., Trends Molec. Med. 2002, 8, S32-S37), such as, for example, viral infections (WO 02/100401). Further investigations on that field were published by Ali, A. et al, (Chembiochem. 2009, 10, 2072-2080). CDK inhibitors could conceivably also be used to treat other conditions such as immunological diseases and neurodegenerative diseases, amongst others.

More than 50 pharmacological CDK inhibitors have been described, some of which have potent antitumor activity (Dai, Y., and Grant, S., Current Opinion in Pharmacology, 2003, 3, 362-370). Recently, molecular markers for prediction of sensitivity of tumor cells towards CDK inhibitors were described (Eguchi, T. et al., Mol. Cancer Ther. 2009, 8, 1460-1472). Contributions concerning the selectivity of protein kinase inhibitors was investigated and published by Bain, J. et al. (Biochem. J. 2007, 408, 297-315) and Karaman, M. W. et al. (Nat. Biotechnol. 2008, 26, 127-132). Furthermore, a comprehensive review about the known CDK inhibitors may be found in the literature (Huwe, A. et al., Angew. Chem. Int. Ed. Engl. 2003, 42, 2122-2138; Krug, M. and Hilgeroth, A. Mini. Rev. Med Chem 2008, 8, 1312-4327). The use of 2-anilino-4-phenylpyrimidine derivatives as cyclin-dependent kinase inhibitors for the treatment of e.g. cancer has been reported in WO 2005/012262. Furthermore, 2-pyridinylamino-4-thiazolyl-pyrimidine derivatives for the treatment of cancer etc. have been described in WO 2005/012298. The use of 4,5-dihydro-thiazolo, oxazolo and imidazolo[4,5-h]quinazolin-8-ylamines as protein kinase inhibitors is known from WO 2005/005438. Furthermore, indolinone derivatives and indirubin derivatives, which are useful as cyclin-dependent kinase inhibitors have been disclosed in WO 02/081445 and WO 02/074742. Additionally, MK inhibitors for various therapeutic applications have been described in WO2005/026129.

Known CDK inhibitors may be classified according to their ability to inhibit CDKs in general or according to their selectivity for a specific CDK. Flavopiridol, for example, acts as a "pan" CDK antagonist and is not particularly selective for a specific CDK (Dai, Y., and Grant, S., Current Opinion in Pharmacology, 2003, 3, 362-370). Purine-based CDK inhibitors, such as olomoucine, roscovitine, purvanolols and CGP74514A are known to exhibit a greater selectivity for CDKs 1, 2 and 5, but show no inhibitory activity against CDKs 4 and 6 (Dai, Y., and Grant, S., Current Opinion in Pharmacology, 2003, 3, 362-370). Furthermore, it has been demonstrated that purine-based CDK inhibitors such as roscovitine can exert anti-apoptotic effects in the nervous system (O'Hare, M. et al., Pharmacol Ther 2002, 93, 135-143) or prevent neuronal death in neurodegenerative diseases, such as Alzheimers's disease (Filgueira de Azevedo, W. Jr., Biochem Biophys Res Commun 2002, 297, 1154-1158; Knockaert, M. et al., Trends Pharmacol Sci 2002, 23, 417-425).

Given the tremendous potential of targeting CDKs for the therapy of conditions such as proliferative, immunological, infectious, cardiovascular and neurodegenerative diseases, the development of small molecules as selective inhibitors of particular CDKs constitutes a desirable goal.

Glycogen synthase kinase-3 (GSK3) was initially identified as an enzyme involved in the control of glycogen metabolism, in particular as a protein kinase that inactivates glycogen synthase. More recently, it has been shown to have key roles in regulating a diverse range of cellular functions by phosphorylating several target proteins, including transcription factors, metabolic enzymes, structural proteins and signaling proteins (Lee, J. et al., Diabetes Res Clin Pract. 2007, 77, Suppl 1:S49-57). Hence, GSK3 is regarded as a key enzyme regulating intracellular signal transduction pathways, thereby controlling cellular responses to extracellular and intracellular regulatory factors. Two isoforms of GSK3 have been described (GSK3-alpha and -beta) which are very similar to each other based on high sequence homology (86% overall and 97% in kinase domains) and biochemical characteristics. However their physiological functions may not be fully redundant as genetic inactivation leads to different phenotypes in mice (Lee, J. et al., Diabetes Res Clin Pract. 2007, 77, Suppl 1:549-57).

Based on the identification of cellular targets and genetic or pharmacologic modulation of GSK3 activity or expression, GSK3 appears to be involved in the molecular pathogenesis of several severe human diseases. For example, GSK3 inhibition has been suggested to exert therapeutic effects in human disorders including metabolic diseases, in particular diabetes (MacAulay, K. et al., Expert Opin Ther Targets. 2008, 12, 1265-1274; Rayasam, G. V. et al., Br J. Pharmacol. 2009, 156, 885-898; Lee, J. et al., Diabetes Res Clin Pract, 2007, 77, Suppl 1:S49-57), neurodegenerative diseases including Alzheimer's disease, Parkinson's disease, Amyotrophic lateral sclerosis and Huntington's disease (Hooper, C. et al., J. Neurochem. 2008, 104, 14334439; Martinez, A., Med Res Rev, 2008, 28, 773-796; Wada, A., Front Biosci. 2009, 14, 15584570; Huang, H. C. et al., Curr Drug Targets. 2006, 7, 1389-1397), parenchymal renal diseases (Obligado, S. H. et al., Kidney Int. 2008, 73, 684-690), neurologic and neuropsychiatric diseases including bipolar disorder (O'Brien, W. T. et al., Biochem Soc. Trans, 2009, 37, (Pt 5) 1133-4138; Jope, R. S. et al., Curr Drug Targets. 2006, 7, 1421-1434), cardiovascular diseases including cardiac infarction and stroke (Juhaszova, M. et al., Circ Res. 2009, 104, 12404252), proliferative diseases including cancer (Luo, J. et al., Cancer Lett. 2009, 273, 194-200) and inflammatory disorders including multiple sclerosis, arthritis and colitis (Jope, R. S. et al., Neurochem Res, 2007, 32, 577-595).

Several GSK3 small molecule inhibitors have been identified, including amino-pyrimidines, thiadiazolidindiones, maleiimides, indirubins, paullones and hymenialdisine (Cohen. P. et al., Nat Rev Drug Discov. 2004, 3, 479-487; Martinez, A., Med Res Rev. 2008, 28, 773-796). Recently, two disclosed GSK3 inhibitors have entered clinical development as disease-modifying drugs for the treatment of Alzheimer's disease. However, kinase selectivity of the presently known inhibitors seems limited and might be critical for further pharmaceutical development. Additionally, all the GSK3 inhibitors developed until now are inhibiting the two isoforms of GSK3, GSK3alpha and beta, with similar potency (Martinez A., Med Res Rev, 2008, 28, 773-796). Thus, the need for further improved inhibitors of GSK3 is strongly indicated.

The present invention provides novel small molecule inhibitors of cyclin-dependent kinases such as CDK9 and/or glycogen synthase kinase 3 family members such as GSK3-alpha and -beta. Suitably, said small molecule inhibitors show selectivity in inhibiting a particular CDK, in particular CDK9, and/or glycogen synthase kinase 3 family members.

Said small molecule inhibitors may have a therapeutic utility for the treatment of conditions such as proliferative, immunological, neurodegenerative, infectious and cardiovascular diseases. Furthermore, the small molecule inhibitors of the present invention have surprisingly been shown to exert a beneficial effect in the treatment of inflammatory diseases and of any type of pain.

Current treatments for inflammatory diseases and any type of pain are only partially effective, and many also cause debilitating or dangerous side effects. For example, many of the traditional analgesics used to treat severe pain induce debilitating side effects such as nausea, dizziness, constipation, respiratory depression, and cognitive dysfunction (Brower, V., Nat Biotechnol, 2000, 18, 387-391).

Current approaches for the treatment of inflammation and especially inflammatory pain aim at cytokine inhibition (e.g. IL1β) and suppression of pro-inflammatory TNFα. Current approved anticytokine/antiTNFα Rx treatments are based on chimeric antibodies such as Infliximab and Etanercept which reduce TNFα circulation in the bloodstream. TNFα is one of the most important inflammatory mediators inducing synthesis of important enzymes such as COX-2, MMP iNOS cPLa$_2$ and others. The main drawbacks of these "biologicals", however, reside in their immunogenic potential with attendant loss of efficacy and their kinetics that lead to a more or less digital all-or-nothing reduction of circulating TNF. The latter can result in severe immune suppressive side effects.

Thus, the usual outcome of such treatment is partial or unsatisfactory, and in some cases the adverse effects of these drugs outweigh their clinical usefulness.

In conclusion, there is a high unmet need for safe and effective methods of treatment of inflammatory diseases and pain treatment, in particular of chronic inflammatory and neuropathic pain.

New approaches like fragment-based screening techniques and structure based drug design or knowledge based prediction of ligand binding modes were described in the literature recently (Wyatt, P. G. et al., J Med Chem 2008, 51, 4986-4999; Chose, A, K. et al., J Med Chem 2008, 51, 5149-5171). A further insight into structural features of CDK9 was performed by the publication of the solved X-ray structure of the complex CDK9/cyclin T1 with flavopiridol (Baumli, S. et al., EMBO J 2008, 27, 1907-1918).

DEFINITIONS

Throughout the description and the claims the expression "alkyl", unless specifically limited, denotes a $C_{1-12}$ alkyl group, suitably a $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g. n-butyl iso-butyl, sec-butyl and tort-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$.

The expression "alkenyl", unless specifically limited, denotes a $C_{2-12}$ alkenyl group, suitably a $C_{2-6}$ alkenyl group, e.g. a $C_{2-4}$ alkenyl group, which contains at least one double bond at any desired location and which does not contain any triple bonds. Alkenyl groups may be straight chain or branched. Exemplary alkenyl groups including one double bond include propenyl and butenyl. Exemplary alkenyl groups including two double bonds include pentadienyl, e.g. (1E,3E)-pentadienyl.

The expression "alkynyl", unless specifically limited, denotes a $C_{2-12}$ alkynyl group, suitably a $C_{2-6}$ alkynyl group, e.g. a alkynyl group, which contains at least one triple bond at any desired location and may or may not also contain one or more double bonds. Alkynyl groups may be straight chain or branched. Exemplary alkynyl groups include propynyl and butynyl.

The expression "alkylene" denotes a chain of formula —$(CH_2)$— wherein n is an integer e.g. 1-5, unless specifically limited.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "cycloalkenyl", unless specifically limited, denotes a $C_{5-10}$ cycloalkenyl group (i.e. 5 to 10 ring carbon atoms), more suitably a $C_{5-8}$ cycloalkenyl group, e.g. a $C_{5-6}$ cycloalkenyl group. Exemplary cycloalkenyl groups include cyclopentenyl, cyclohexenyl, cycloheptenyl and cyclooctenyl. A most suitable number of ring carbon atoms is five to six.

The expression "carbocyclic" or "carbocycle", unless specifically limited, denotes any ring system in which all the ring atoms are carbon and which contains between three and twelve ring carbon atoms, suitably between three and ten carbon atoms and more suitably between three and eight carbon atoms. Carbocyclic groups may be saturated or partially unsaturated, but do not include aromatic rings or non-aromatic rings fused to aromatic rings. Examples of carbocyclic groups include monocyclic, bicyclic, and tricyclic ring systems, in particular monocyclic and bicyclic ring systems. Other carbocylcyl groups include bridged ring systems (e.g. bicyclo[2.2.1]heptenyl). A specific example of a carbocyclic group is a cycloalkyl group. A further example of a carbocyclic group is a cycloalkenyl group.

The expression "heterocyclic" or "heterocycle", unless specifically limited, refers to a carbocyclic group wherein one or more (e.g. 1, 2 or 3) ring atoms are replaced by heteroatoms selected from N, S and O. A specific example of a heterocyclic group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O (in particular N or O). Exemplary heterocyclic groups containing one hetero atom include pyrrolidine, tetrahydrofuran and piperidine, and exemplary heterocyclic groups containing two hetero atoms include morpholine and piperazine. A further specific example of a heterocyclic group is a cycloalkenyl group (e.g. a cyclohexenyl group) wherein one or more (e.g. 1, 2 or 3, particularly 1 or 2, especially 1) ring atoms are replaced by heteroatoms selected from N, S and O (in particular N or O). An example of such a group is dihydropyranyl (e.g. 3,4-dihydro-2H-pyran-2-yl-).

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings) but may also contain additional rings which are non-aromatic. An example of a typical aryl group with one aromatic ring is phenyl. An example of a typical aryl group with two aromatic rings is naphthyl. Phenyl fused to $C_{5-8}$ carbocyclic (suitably $C_{5-6}$ carbocyclic) (e.g. indane) is also an example of aryl.

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl, imidazol-4-yl); six membered rings (e.g. pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzthiazole quinazoline and purine. Phenyl fused to heterocyclic (e.g. benzo-1,3-dioxol-5-yl, 2,3-dihydro-benzo-1,4-dioxin-6-yl) is also an example of heteroaryl. Suitably the heteroatom or heteroatoms are members of the aromatic ring.

The aforementioned aryl and heteroaryl groups may, where appropriate, optionally be substituted by one or more (e.g. 1, 2 or 3, typically 1 or 2) monovalent or multivalent functional groups. Suitable substituent groups include alkyl, cycloalkyl, phenyl, pyridyl, furyl, carbocylic, heterocyclic, alkoxy, cycloalkoxy, phenyloxy, carbacyclicoxy, heterocyclicoxy, alkenyloxy, alkynyloxy, alkenyl, alkynyl, alkanoyl, alkoxyalkanoyl, alkoxyalkyl, nitro, —S-alkyl (e.g. methylthio), halo (e.g. fluoro, chloro, bromo and iodo), cyano, hydroxyl, —$SO_2$ alkyl, —$SO_2$ cycloalkyl, —$SO_2$ heterocyclic, —$CO_2H$, —$CO_2$ alkyl, —$NH_2$, —NHalkyl, —N(alkyl)$_2$ (e.g. dimethylamino), —CO—N(alkyl)$_2$ and —CO—NH(alkyl). Most typical substituent groups are selected from alkyl, alkoxy, halo, nitro and hydroxyl.

Examples of substituted aryl groups include 4-fluoro-phenyl, 3-fluoro-phenyl, pentafluoro-phenyl, 4-hydroxyphenyl-, 3-nitro-phenyl-, 4-(trifluoromethyl)-phenyl, 4-anilinyl-, 2-3-biphenylyl- and 4-biphenylyl-. Examples of substituted heteroaryl groups include N-methyl-2-pyrrolyl, 2-methyl-1-pyrrolyl, 3-methyl-2-pyrrolyl and 3-phenyl-1-pyrrolyl.

Examples of -alkylaryl include phenylmethyl-(i.e. benzyl) and phenylethyl, 2-phenyleth-1-yl, p-tolyl-methyl-, p-tolyl-ethyl-, m-tolyl-methyl-, m-tolyl-ethyl-, o-tolyl-methyl-, o-tolyl-ethyl-, 2-(4-ethyl-phenyl)-ethyl-yl-, 2,3-dimethyl-phenyl-methyl-2,4-dimethyl-phenyl-methyl-, 2,5-dimethyl-phenyl-methyl-, 2,6-dimethyl-phenyl-methyl-, 3,4-dimethyl-phenyl-methyl-, 3,5-dimethyl-phenyl-methyl-, 2,4,6-trimethyl-phenyl-methyl-, 2,3-dimethyl-phenyl-ethyl, 2,4-dimethyl-phenyl-ethyl-2,5-dimethyl-phenyl-ethyl-, 2,6-dimethyl-phenyl-ethyl-, 3,4-dimethyl-phenyl-ethyl, 3,5-dimethyl-phenyl-ethyl-, 2,4,6-trimethyl-phenyl-ethyl-, benzhydryl (i.e. diphenyl-methyl, diphenyl-ethyl), trityl (i.e. triphenyl-methyl), triphenyl-ethyl, cumyl (i.e. 1-methyl-1-phenylethyl), 2-ethyl-phenyl-methyl-3-ethyl-phenyl-methyl-, 4-ethyl-phenyl-methyl-, 2-ethyl-phenyl-ethyl-, 3-ethyl-phenyl-ethyl-, 4-ethyl-phenyl-ethyl-, 2-fluoro-benzyl, 1-methyl-2-fluoro-phen-6-yl-methyl-, 1-methyl-2-fluoro-phen-4-yl-methyl-, 1-methyl-2-fluoro-phen-6-yl-ethyl-, 1-methyl-2-fluoro-phen-4-yl-ethyl-, 1H-indenyl-methyl-, 2H-indenyl-methyl-, 1H-indenyl-ethyl-, 2H-indenyl-ethyl-, indanyl-methyl-, ethyl-, tetralinyl-methyl-, tetralinyl-ethyl-, fluorenyl-methyl-, fluorenyl-ethyl-, dihydronaphthalinyl-methyl dihydronaphthalinyl-ethyl-, or (4-cyclohexyl)-phenyl-methyl-, (4-cyclohexyl)-phenyl-ethyl-. A most typical-alkylaryl group is phenylmethyl-.

Examples of -alkylheteroaryl include pyridinylmethyl- (e.g. 2-pyridinylmethyl), N-methyl-pyrrol-2-methyl-, N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-4-pyridino-methyl-, 4-pyridino-ethyl-, 2-(thiazol-2-yl)-ethyl-, tetrahydroisochinolinyl-methyl-, tetrahydroisochinolinyl-ethyl-, 2-ethyl-indol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl, 4-methyl-pyridin-3-ethyl. A most typical -alkylheteroaryl group is pyridinylmethyl-.

The expression "-alkylcarbocyclic", unless specifically limited, denotes a carbocyclic residue which is connected via an alkylene moiety e.g. a $C_{1-4}$ alkylene moiety.

The expression "-alkylheterocyclic", unless specifically limited, denotes a heterocyclic residue which is connected via an alkylene moiety e.g. a $C_{2-4}$ alkylene moiety.

The expression "-alkylaryl", unless specifically limited, denotes an aryl residue which is connected via an alkylene moiety e.g. a $C_{1-4}$ alkylene moiety.

The expression "-alkylheteroaryl", unless specifically limited, denotes a heteroaryl residue which is connected via an alkylene moiety e.g. a $C_{1-4}$ alkylene moiety.

The term "halogen" or "halo" comprises fluorine (F), chlorine (Cl) and bromine (Br).

The term "amino" refers to the group —$NH_2$.

Stereoisomers:

All possible stereoisomers of the claimed compounds are included in the present invention.

Where the compounds according to this invention have at least one chiral centre, they may accordingly exist as enantiomers. Where the compounds possess two or more chiral centres, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-D-tartaric acid and/or (O-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts or solvates, whenever a compound is referred to in this context, a corresponding salt, solvate or polymorph is also intended, provided such is possible or appropriate under the circumstances.

Solvates

Some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Salts and solvates of the compounds of Formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulphuric, nitric, citric, tartaric, phosphoric, lactic, pyruvic, acetic, trifluoroacetic, triphenylacetic, sulphanilic, succinic, oxalic, fumaric, maleic, mandelic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, cinnamic, substituted cinnamic (for example phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) isethionic acids, perchloric, propionic, glycolic, hydroxyethanesulfonic, pamoic, cyclohexanesulfamic, salicylic, saccharinic and trifluoroacetic acid, particularly hydrochloric. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. 11. Bundgaard, Elsevier, 1985.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in the literature, fully incorporated herein by reference (Protective Groups in Organic Chemistry, ed. McOmie, J. F. W., Plenum Press, 1973; Greene, T. W. and Wuts, P. G. M., Protective Groups in Organic Synthesis, John Wiley & Sons, 1991). The protecting groups may be removed at a convenient subsequent stage using methods known from the art.

As used herein, the term "composition" is intended to encompass a product comprising the claimed compounds in the therapeutically effective amounts, as well as any product which results, directly or indirectly, from combinations of the claimed compounds.

SUMMARY OF THE INVENTION

The present invention is directed to inhibitors of cyclin-dependent kinases and/or glycogen synthase kinase 3 family members and to methods and compositions for treating and/or preventing any type of pain, inflammatory disorders, immunological diseases, proliferative diseases, infectious diseases, cardiovascular diseases, metabolic diseases, neuropsychiatric diseases, renal diseases and neurodegenerative diseases comprising: administering an effective amount of at least one inhibitor of a cyclin-dependent kinase (cdk, CDSK) and/or glycogen synthase kinase 3 to a subject in need thereof.

According to the invention, there is provided an inhibitor compound of general Formula (I);

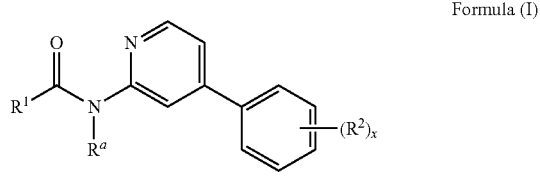

Formula (I)

or a pharmaceutically acceptable salt, solvate or polymorph thereof, including all tautomers and stereoisomers thereof.
Wherein:
$R^a$ is H or methyl;
$R^1$ is selected from the group consisting of:
carbocyclic or —$C_{1-6}$ alkyl-carbocyclic, wherein the carbocyclic group is cyclohexyl or cyclopentyl;
heterocyclic or —$C_{1-6}$ alkyl-heterocyclic group, wherein the heterocyclic group is piperidine, piperazine, morpholine or pyrrolidine;
aryl or —$C_{1-6}$ alkyl-aryl;
heteroaryl or —$C_{1-6}$ alkyl-heteroaryl, wherein the heteroaryl group is pyridine, thiazole or thiophene;
wherein any of the aforesaid carbocyclic, heterocyclic, aryl or heteroaryl groups may optionally be substituted by one or more groups independently selected from:
halo, OH, $NH_2$ and, for carbocyclic and heterocyclic groups, =O; or
$C_{1-4}$ alkyl, —O($C_{1-4}$alkyl), —NH($C_{1-4}$ alkyl), —NHC(O)($C_{1-4}$alkyl), —S($C_{1-4}$alkyl), —SO($C_{1-4}$ alkyl), —$SO_2$($C_{1-4}$alkyl) or —$SO_2$NH($C_{1-4}$alkyl) any of which may be further substituted with halo or OH; or
$R^3$, —$C_{1-4}$ alkyl-$R^3$, $OR^3$, $NHR^3$, —$NHC_{1-4}$ alkyl-$R^3$, —$OC_{1-4}$alkyl-$R^3$, $SR^3$, $SOR^3$ or $SO_2R^3$;
wherein $R^3$ is an aryl, heteroaryl, carbocyclic or heterocyclic group any of which may be substituted with one or more (e.g. one) halo, $C_{1-4}$alkyl, —O($C_{1-4}$ alkyl), $NH_2$, —NH($C_{1-4}$alkyl), —C(O)($C_{1-4}$alkyl) groups,
—NHC(O)$C_{1-4}$alkyl), any of which alkyl groups may be substituted with halo or OH;
each $R^2$ is independently halo, OH, $NH_2$; or
$C_{1-4}$alkyl, —O($C_{1-4}$alkyl), —NH($C_{1-4}$alkyl), —C(O)($C_{1-4}$alkyl), any of which may be further substituted with halo or OH; or
$R^4$, —$C_{1-4}$ alkyl-$R^4$, $OR^4$, $NHR^4$, —$NHC_{1-4}$alkyl-$R^4$, —$OC_{1-4}$alkyl-$R^4$, $SR^4$, $SOR^4$ or $SO_2R^4$;
wherein $R^4$ is an aryl, heteroaryl, carbocyclic or heterocyclic group any of which may be substituted with one or more (e.g. one) halo, OH, $C_{1-4}$alkyl, —O($C_{1-4}$alkyl), $NH_2$, —NH($C_{1-4}$ alkyl), —C(O)($C_{1-4}$alkyl), —NHC(O)($C_{1-4}$alkyl) groups, any of which alkyl groups may be substituted with halo or OH; and
x is 0-4.

Some compounds similar to those of general formula (I) are known from the prior art. For example, from EP 1 679 309 (Ono Pharmaceutical), which concerns anti-stress drugs as well as indications such as Parkinson's disease, schizophrenia, myocardial infarction. EP 1 679 309 discloses some compounds which are similar to compounds of the present invention; however, these compounds differ from the compounds of the present invention in that the exemplified compounds are all pyrimidines rather than pyridine derivatives.

WO 2004/084824 (Merck) concerns biaryl substituted 6-membered heterocycles as sodium channel blockers. Indications include chronic and neuropathic pain and other conditions including CNS disorders. WO 2004/084824 discloses compounds which differ from the compounds of the present invention in that all of the cyclic components are directly linked.

WO 2002/094825 (Banyu Pharmaceutical) concerns NPY agonists and indications include circulatory diseases, central diseases, metabolic diseases, sexual and reproductive dysfunction, digestive diseases, respiratory diseases etc. The compounds disclosed in this document differ from those of the present invention in that WO 2002/094825 concerns compounds in which $R^1$ (as defined by the present application) is a three ring system comprising a piperidine ring linked to a terminal bicyclic ring via a spiro ring junction.

WO 2005/103022 (Transtech Pharma) concerns substituted thiazole and pyrimidine derivatives as melancortin receptor modulators. Indications include cancer include cardiovascular diseases. WO 2005/103022 discloses some compounds which are similar to compounds of the present invention; however, these compounds differ from the compounds of the present invention as they are thiazole or pyrimidine derivatives rather than pyridine derivatives.

FR 2878247 (Galderma Research & Development) concerns novel compounds that modulate peroxisome proliferator-activated receptor type of subtype gamma receptors and use thereof in cosmetic or pharmaceutical compositions. The indications are mostly skin disorders but also include disorders related to lipid metabolism, such as obesity, and inflammatory conditions, such as arthritis, and cancer. The examples disclosed by FR 2878247 which are most similar to the compounds of the present application differ from the compounds of the present invention in that the substituents are in a different configuration.

WO 2001/62233 (F Hoffmann La Roche) concerns adenosine receptor modulators. Indications include inter alia Alzheimer's, Parkinson's, schizophrenia and pain. WO 2001/62233 discloses some compounds which are similar to compounds of the present invention; however, these compounds do not have an $R^1$ substituent similar to that of the present invention.

U.S. Pat. No. 5,886,191 relates to amidinoindole and amidinoazole analogue compounds which are said to have anticoagulant activity and to be useful for treating thromboembolic disorders.

WO 2005/003123 relates to compounds of the formula:

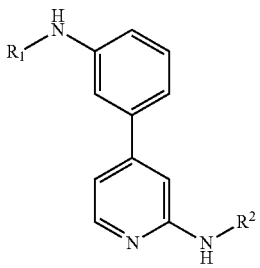

The compounds area said to be JNK specific inhibitors for use in the treatment of conditions such as cancer, Alzheimer's disease, stroke, Parkinson's disease, ALS and Huntington's disease.

WO 2009/140519 relates to compounds which modulate the activity of the TPRA1 channel and are useful in treating injuries caused by chemical warfare agents.

WO 2002/102790 relates to N-formyl hydroxylamine compounds as PDF inhibitors which are useful in treating infection.

EP 0254322 relates to compounds of the formula:

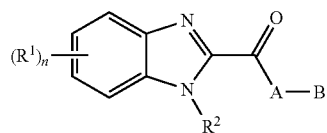

where A can be NH and B can be pyridyl optionally substituted with phenyl. The compounds are said to have cardiotonic properties and to be of use in the treatment of conditions such as congestive heart failure, arrhythmia, angina pectoris and hypertension.

WO 2010/053861 relates to amide compounds which are said to be useful for the treatment of conditions including pain, cognitive disorders and mood impairment.

Our earlier application WO 2009/047359 relates to inhibitors of cyclin-dependent kinases. These compounds are similar to the compounds of the present invention except that they are pyrimidines rather than pyridines. This modification from pyrimidine to pyridine for the core moiety opens new features in the profile of these compounds, especially in respect to their solubility, transport, metabolism and further details of characterisation.

In certain compounds of the present invention $R^a$ is H.

In suitable compounds of the invention, x is 0 to 3 and compounds in which x is 2 are particularly suitable.

The positions of the $R^2$ ring substituents are referred to as follows:

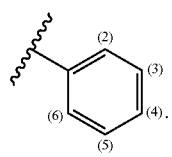

When x is greater than 1, the $R^2$ substituents may be the same or different.

In suitable compounds of general formula (I), $R^2$ is halo, $C_{1-4}$ alkyl, $C_{1-4}$ haloalkyl, $C_{1-4}$ alkoxy or $C_{1-4}$haloalkoxy.

Particularly suitable $R^2$ groups include fluoro or methyl or methoxy, either of which is optionally substituted with 1 to 3 halo, especially fluoro, moieties.

In some examples of compounds of general formula (I), there are two $R^2$ groups, one of which is halo and the other of which is methoxy or halomethoxy. Typically, the methoxy or halomethoxy group is at the 2-position and the halo group is at the 4- or 5-position. Thus specific examples of the phenyl substituted with $R^2$ substituents include 4-fluoro-2-methoxyphenyl and 5-fluoro-2-methoxyphenyl.

In suitable compounds of the present invention, the group $R^1$ is: $C_5$ or $C_6$ carbocyclic, $C_5$ or $C_6$ heterocyclic, —$C_{1-3}$alkyl-phenyl, —$C_{1-3}$alkyl($C_5$ or $C_6$ heteroaryl), —$C_{1-3}$ alkyl($C_5$ or $C_6$ carbocyclic), —$C_{1-3}$alkyl($C_s$ or $C_6$ heterocyclic), phenyl or $C_s$ or $C_6$ heteroaryl, wherein any of the aforesaid cyclic groups may optionally be substituted as described above.

Thus, suitably, $R^1$ is cyclohexyl, cyclopentyl, —$C_{1-3}$alkyl (cyclohexyl), —$C_{1-3}$alkyl(cyclopentyl); or $R^1$ is piperidine, piperazine, morpholine and pyrrolidine, —$C_{1-3}$alkyl(piperidine), —$C_{1-3}$ alkyl(piperazine), —$C_{1-3}$ alkyl(morpholine), —$C_{1-3}$ alkyl(pyrrolidine); or $R^1$ is phenyl or —$C_{1-3}$alkyl-phenyl; or $R^1$ is pyridine, thiazole, thiophene, —$C_{1-3}$ alkyl (pyridine), —$C_{1-3}$ alkyl(thiazole) or —$C_{1-3}$ alkyl(thiophene), wherein any of the aforesaid cyclic groups may optionally be substituted as described above.

When $R^1$ is a —$C_{1-3}$alkyl(carbocyclic), —$C_{1-3}$alkyl(heterocyclic), —$C_{1-3}$ alkyl(aryl) or —$C_{1-3}$ alkyl(heteroaryl) group, particularly suitable —$C_{1-3}$ alkyl linker moieties include:

—$CH_2$—;
—$CH(CH_3)$—;
—$CH_2CH(CH_3)$—;
—$CH(CH_3)CH_2$—; and
—$CH_2CH_2$—.

When carbocyclic, heterocyclic, aryl or heteroaryl groups of $R^1$ are substituted, suitable substituents include one or more groups chosen from:

halo, OH, $NH_2$ and, for carbocyclic and heterocyclic groups, =O; or $C_{1-4}$ alkyl, —O($C_{1-4}$ alkyl), —NH($C_{1-4}$ alkyl), —NHC(O) ($C_{1-4}$ alkyl), any of which may be further substituted with halo or OH; or $R^3$, —$C_{1-4}$ alkyl-$R^3$, $OR^3$, $NHR^3$, —$NHC_{1-4}$ alkyl-$R^3$, —$OC_{1-4}$alkyl-$R^3$;

wherein $R^3$ is an aryl, heteroaryl, carbocyclic or heterocyclic group any of which may be substituted with one or more halo, OH, $NH_2$ or $C_{1-4}$ alkyl or —O($C_{1-4}$alkyl) groups, either of which alkyl groups may be substituted with halo.

More suitable substituents for the carbocyclic, heterocyclic, aryl or heteroaryl groups of $R^1$ include one or more groups chosen from $NH_2$, methyl, ethyl, methoxy, ethoxy, chloro, fluoro, trifluoromethyl, trifluoromethoxy, =O (for carbocyclic and heterocyclic groups), NHC(O)Me, $R^3$, $NHR^3$, and $NHCH_2R^3$, wherein $R^3$ is as defined above.

Particularly suitable $R^3$ groups include cyclic groups with five or six ring atoms. Examples of such $R^3$ groups include piperidine, 4-methylpiperidine, piperazine, 4-methylpiperazine, thienyl, for example thien-2-yl, thiazolyl, for example thiazol-2-yl, pyridinyl, for example pyridin-2-yl, pyridine-3-yl or pyridine-4-yl, and phenyl.

When $R^3$ represents aryl, heteroaryl, carbocyclic or heterocyclic group it may, for example be unsubstituted or substituted by $C_{1-4}$alkyl (for example it may be unsubstituted).

When R⁴ represents aryl, heteroaryl, carbocyclic or heterocyclic group it may, for example be unsubstituted or substituted by $C_{1-4}$alkyl (for example it may be unsubstituted).

Suitable compounds of Formula (I) include:
1. N-(4-(4-Fluoro-2-methoxyphenyl)pyridin-2-yl)cyclohexanecarboxamide;
2. 2-Cyclohexyl-N-(4-(4-fluoro-2-methoxyphenyl)pyridin-2-yl)acetamide;
3. N-(4-(4-Fluoro-2-methoxyphenyl)pyridin-2-yl)piperidine-4-carboxamide;
4. 4-Amino-N-(4-(4-fluoro-2-methoxyphenyl)pyridin-2-yl)cyclohexane-carboxamide;
5. N-(4-(4-Fluoro-2-methoxyphenyl)pyridin-2-yl)-5-oxopyrrolidine-3-carboxamide;
6. N-(4-(4-Fluoro-2-methoxyphenyl)pyridin-2-yl)-2-(4-methoxyphenyl)-acetamide;
7. N-(4-(4-Fluoro-2-methoxyphenyl)pyridin-2-yl)-2-phenylacetamide;
8. N-(4-(4-Fluoro-2-methoxyphenyl)pyridin-2-yl)-2-(pyridin-4-yl)acetamide;
9. N-(4-(4-Fluoro-2-methoxyphenyl)pyridin-2-yl)-2-(thiophen-2-yl)acetamide;
10. (2S)—N-(4-(5-Fluoro-2-methoxyphenyl)pyridin-2-yl)-2-phenylpropanamide;
11. (2S)—N-(4-(4-Fluoro-2-methoxyphenyl)pyridin-2-yl)-2-(4-methoxyphenyl)-propanamide;
12, 13. Isomers of N-(4-(4-Fluoro-2-methoxyphenyl)pyridin-2-yl)-2-(pyridin-3-yl)propanamide;
14. N-(4-(4-Fluoro-2-methoxyphenyl)pyridin-2-yl)-2-(6-methoxypyridin-3-yl)acetamide;
15, 16. Isomers of N-(4-(4-Fluoro-2-methoxyphenyl)pyridin-2-yl)-2-(pyridin-4-yl)propanamide;
17, 18. Isomers of (2R)—N-(4-(5-Fluoro-2-methoxyphenyl)pyridin-2-yl)-2-(thiophen-2-yl)propanamide
19. 2-(2-Chloropyridin-4-yl)-N-(4-(4-fluoro-2-methoxyphenyl)pyridin-2-yl)acetamide;
20. N-(4-(4-Fluoro-2-methoxyphenyl)pyridin-2-yl)-2-(4-(4-methylpiperazin-1-yl)phenyl)acetamide;
21. N-(4-(4-Fluoro-2-methoxyphenyl)pyridin-2-yl)-3-(pyridin-4-yl)butanamide;
22. N-(4-(4-Fluoro-2-methoxyphenyl)pyridin-2-yl)-2-((pyridin-4-yl)methyl)-propanamide;
23. N-(4-(4-Fluoro-2-methoxyphenyl)pyridin-2-yl)-3-(pyridin-3-yl)butanamide;
24. N-(4-(4-Fluoro-2-methoxyphenyl)pyridin-2-yl)-2-((pyridin-3-yl)methyl)-propanamide;
25, 26. trans-3-Acetamido-N-(4-(4-fluoro-2-methoxyphenyl)-pyridin-2-yl)cyclohexanecarboxamide;
27. N-(4-(4-Fluoro-2-methoxyphenyl)pyridin-2-yl)-2-(4-(4-methylpiperazin-1-yl)phenyl)propanamide;
28. 2-(4-(4-Methylpiperazin-1-yl)benzyl)-N-(4-(4-fluoro-2-methoxyphenyl)-pyridin-2-yl)propanamide;
29. N-(4-(4-Fluoro-2-methoxyphenyl)pyridin-2-yl)-3-(4-(4-methylpiperazin-1-yl)phenyl)butanamide;
30. N-(4-(4-Fluoro-2-methoxyphenyl)pyridin-2-yl)-4-(pyridin-2-ylamino)-cis-cyclohexanecarboxamide;
31. N-(4-(4-Fluoro-2-methoxyphenyl)pyridin-2-yl)-2-(2-(4-methylpiperazin-1-yl)pyridin-4-yl)acetamide;
32. cis-N-(4-(4-Fluoro-2-methoxyphenyl)pyridin-2-yl)-4-(pyridin-4-ylamino)-cyclohexanecarboxamide;
33. cis-3-Acetamido-N-(4-(4-fluoro-2-methoxyphenyl)pyridin-2-yl)cyclo-hexanecarboxamide;
34. (1R,3S)-3-Acetamido-N-(4-(4-fluoro-2-methoxyphenyl)pyridin-2-yl)cyclopentanecarboxamide;
35. cis-N-(4-(4-Fluoro-2-methoxyphenyl)pyridin-2-yl)-4-(thiazol-2-ylamino)-cyclohexanecarboxamide;
36. cis-N-(4-(4-Fluoro-2-methoxyphenyl)pyridin-2-yl)-4-(phenylamino)-cyclohexanecarboxamide;
37. (1R,3S)-3-(Benzylamino)-N-(4-(4-fluoro-2-methoxyphenyl)pyridin-2-yl)cyclopentanecarboxamide;
38. cis-4-(Benzylamino)-N-(4-(4-fluoro-2-methoxyphenyl)pyridin-2-yl)cyclo-hexanecarboxamide;
39. (1R,3S)—N-(4-(4-Fluoro-2-methoxyphenyl)pyridin-2-yl)-3-(phenylamino)-cyclopentanecarboxamide;
40. (1R,3S)-3-Acetamido-N-(4-(4-fluoro-2-methoxyphenyl)pyridin-2-yl)cyclohexanecarboxamide;

or their pharmaceutically acceptable salts, solvates or polymorphs, including all tautomers and stereoisomers.

Another suitable compound of Formula (I) is:
(1S,3R)-3-Acetamido-N-(4-(4-fluoro-2-methoxyphenyl)pyridin-2-yl)cyclopentanecarboxamide; and its pharmaceutically acceptable salts, solvates or polymorphs, including all tautomers and stereoisomers.

Compounds of formula (I) may be synthesized from compounds of formula (II):

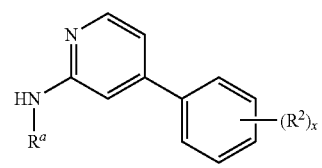

(II)

wherein $R^a$ and $R^2$ and x are as defined for formula (I); by reaction with a compound of formula (III):

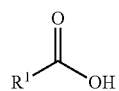

(III)

wherein $R^1$ is as defined for general formula (I).

The reaction may be carried out using a HATU coupling method as described in Method A below.

Compounds of formula (III) are well known and are either readily available or may be prepared by methods well known to those of skill in the art.

Compounds of formula (II) may be prepared by the reaction of a compound of formula (IV):

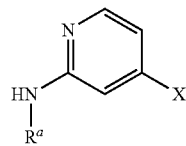

(IV)

wherein $R^a$ and $R^2$ are as defined for formula (I) and X is a leaving group, particularly chlorine;
with a compound of formula (V):

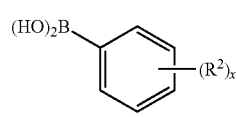

(V)

wherein $R^2$ and x are as defined for formula (I).

The reaction may be carried out as described in the general methods below.

Compounds of formulae (IV) and (V) are well known and are either readily available or may be prepared by methods well known to those of skill in the art.

An alternative method for the preparation of compounds of formula (I) is by the reaction of a compound of formula (VI):

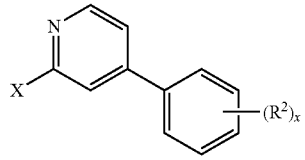
(VI)

wherein $R^2$ and x are as defined for Formula (I) and X is a leaving group, particularly chlorine; with a compound of formula (VII):

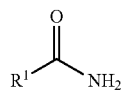
(VII)

wherein $R^1$ is as defined in formula (I).

The reaction may be carried out using a Buchwald type reaction as described in Method B below.

Compounds of formula (VII) are well known and are either readily available or may be prepared by methods well known to those of skill in the art.

Compounds of formula (VI) may be prepared by reacting 4-bromo-2-chloropyridine with a compound of formula (V) as defined above under the reaction conditions described in the general methods section below. Compounds of formula (V) and 4-bromo-2-chloropyridine are readily available starting materials.

Alternatively, a compound of formula (I) may be prepared from a protected compound of formula (I). For example, a compound of formula (I) in which $R^1$ has a free primary or secondary amine group (for example when $R^1$ is piperidin-4-yl) may be prepared by deprotecting a suitably protected compound. An example of a suitable amine protecting group is BOC and in the case when $R^1$ is piperidin-4-yl, the protected $R^1$ group is:

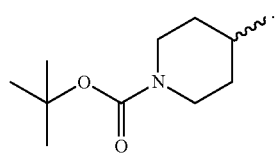

Deprotection of an amine is described in Method C below.

Compounds of formula (I) may also be prepared from other compounds of formula (I). An example of this is the conversion of a compound of formula (I) wherein $R^1$ is a cyclic group substituted with $NH_2$ to a compound of formula (I) wherein $R^1$ is a cyclic group substituted with $NHR^3$, wherein $R^3$ is as defined for formula (I). The reaction may be carried out using a Chan-Lam type coupling reaction as described in Method D below.

Therefore, in a further aspect of the invention, there is provided a process for the preparation of a compound of formula (I) comprising:

a. reacting a compound of formula (II):

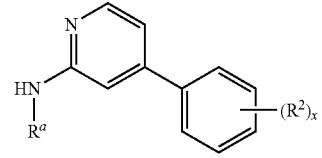
(II)

wherein $R^a$, $R^2$ and x are as defined for formula (I);
with a compound of formula (III):

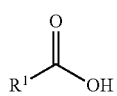
(III)

wherein $R^1$ is as defined for general formula (I) using a HATU coupling method; or b. reacting a compound of formula (VI):

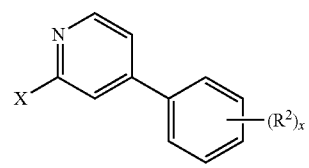
(VI)

wherein $R^2$ and x are as defined for Formula (I) and X is a leaving group, particularly chlorine; with a compound of formula (VII):

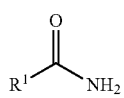
(VII)

wherein $R^1$ is as defined in formula (I);
using a Buchwald type reaction; or c. deprotecting a protected compound of formula (I); or d. conversion of a compound of formula (I) to another compound of formula (I).

Compounds of formulae (II) and (VI) form further aspects of the invention.

As already described above, Compounds of formula (I) are inhibitors of kinases which are related to the cyclin-dependent kinase family on a molecular level and therefore commonly grouped to the CMGC class of kinases comprising the CDK family, MAP-kinase family, GSK3 family and CDK-like kinase family (Manning G. et al., Science 2002, 298, 1912-1934).

In particular, compounds of formula (I) inhibit kinases of the CDK family and/or the GSK3 family and/or the CDK-like kinase family. Based on sequence homology, the CDK family can be commonly regarded as consisting of the kinases designated as CDK1/CDC2, CDK2, CDK3, CDK4, CDK5, CDK6, CDK7, CDK8, CDK9, CDK10, CDK11/CDC2L6, CCRK, CrkRS/Crk7/CDK12, CHED/CDC2L5/CDK13, PITSLRE A, PITSLRE B, PCTK1 (PCTAIRE protein kinase 1), PCTK2 (PCTAIRE protein kinase 2), PCTK3 (PCTAIRE protein kinase 3), PFTK1 (PFTAIRE protein kinase 1) and PFTK2 (PFTAIRE protein kinase 2). The GSK3 kinase family comprises CDKL1 (cyclin-dependent kinase-like 1)/KKIALRE, CDKL2 (cyclin-dependent kinase-like 2)/KKIAMRE, CDKL3 (cyclin-dependent kinase-like 3)/NKIAMRE, CDKL4, CDKL5, GSK3alpha, GSK3beta, MOK, ICK and MAK. The CDK-like kinase family comprises DYRK1A, DYRK1B, DYRK2, DYRK3, DYRK4, PRP4, HIPK1, HIPK2, HIPK3, HIPK4, CLK1, CLK2, CLK3, CLK4, MSSK1, SRPK1 and SRPK2.

It is advantageous for a compound to be a selective inhibitor of one or more CDKs and/or glycogen synthase kinase 3 family members without having a substantial inhibitory effect on other enzymes or proteins. In particular, it is advantageous for compounds to display an increased selectivity for a particular CDK. "Increased selectivity" as used herein means that the inhibitory compound is at least 10-100 times more selective for a particular kinase selected from the group of CDKs and/or the glycogen synthase kinase 3 family as recited herein, supra. It is preferred that the inhibitory compound is 20-90 times more selective for a particular kinase and it is particularly preferred that the inhibitory compound is 30-80 times more selective for a particular kinase.

The compounds of formula (I) display an increased selectivity for CDK9 over other kinases.

As used herein, the term "inhibiting" or "inhibition" refers to the ability of a compound to downregulate, decrease, reduce, suppress, inactivate, or inhibit at least partially the cellular function of a cyclin-dependent kinase, i.e. its activity or the expression of the cyclin-dependent kinase.

Furthermore, the term "cyclin-dependent kinase inhibitor" or "glycogen synthase kinase 3 family inhibitor" refers to any compound or group of compounds that is capable of downregulating, decreasing, suppressing or otherwise regulating the amount and/or activity of a cyclin-dependent kinase family member or glycogen synthase kinase 3 family member. Inhibition of said kinases can be achieved by any of a variety of mechanisms known in the art, including, but not limited to binding directly to the kinase polypeptide, denaturing or otherwise inactivating the kinase, or inhibiting the expression of the gene (e.g., transcription to mRNA, translation to a nascent polypeptide, and/or final polypeptide modifications to a mature protein), which encodes the kinase. Furthermore, a kinase inhibitor may also interfere with expression, modification, regulation or activation of a molecule acting downstream of a CDK in a CDK-dependent pathway. Generally, kinase inhibitors may be proteins, polypeptides, nucleic acids, small molecules, or other chemical moieties. Specifically, kinase inhibitors also include monoclonal or polyclonal antibodies directed against cyclin-dependent kinases.

Therapeutic Use

The compounds of Formula (I) are inhibitors of cyclin-dependent kinases and/or the glycogen synthase kinase 3 family. Thus, they are expected to have the ability to arrest, or to recover control of the cell cycle in abnormally dividing cells. Consequently, the compounds according to Formula (I) will prove useful in treating and/or preventing proliferative disorders such as cancers.

In a further aspect of the invention, therefore, there is provided a compound of general Formula (I) for use in medicine, particularly in the treatment of diseases and conditions mediated by the activity of cyclin dependent kinases, especially CDK9.

There is further provided the use of a compound of general Formula (I) in the preparation of an agent for the treatment of diseases and conditions mediated by the activity of cyclin dependent kinases, especially CDK9.

Furthermore, the invention provides a method for the treatment of diseases and conditions mediated by the activity of cyclin dependent kinases, especially CDK9, the method comprising administering to a subject in need of such treatment an effective amount of a compound of general Formula (I).

It is known that CDKs and GSK3 family members play a role in apoptosis, proliferation, differentiation and transcription and therefore, the compounds according to Formula (I) may also be useful in the treatment of diseases other than proliferative diseases, such as infectious diseases, immunological diseases, neurodegenerative diseases, inflammatory disorders, metabolic disorders, renal diseases, neurologic and neuropsychiatric diseases, cardiovascular diseases and pain.

Importantly, the compounds according to Formula (I) also display an anti-inflammatory effect, which is unexpected due to their high selectivity for CDK9 and/or GSK3.

Pain

Neuropathic Pain:

The discovery that inhibition of a cyclin-dependent kinase is involved in mediating a hypoalgesic effect was unexpected.

Thus, the invention relates to a compound of formula (I) for use in the treatment of pain.

Furthermore the invention relates to the use of a compound of formula (I) in the preparation of a medicament for the treatment of pain.

The invention also relates to a method for the treatment of pain, the method comprising administering to a subject in need of such treatment an effective amount of an inhibitor of cyclin-dependent kinase according to Formula (I).

In particular, the compounds of Formula (I) may be used for the treatment of chronic, neuropathic and/or inflammatory pain.

The term "pain" as used herein generally relates to any type of pain and broadly encompasses types of pain such as acute pain, chronic pain, inflammatory and neuropathic pain. In a preferred embodiment of the present invention, "pain" comprises neuropathic pain and associated conditions. The pain may be chronic, allodynia (the perception of pain from a normally innocuous stimulus), hyperalgesia (an exaggerated response to any given pain stimulus) and an expansion of the receptive field (i.e. the area that is "painful" when a stimulus is applied), phantom pain or inflammatory pain.

Acute pain types comprise, but are not limited to pain associated with tissue damage, postoperative pain, pain after trauma, pain caused by burns, pain caused by local or systemic infection, visceral pain associated with diseases comprising: pancreatits, intestinal cystitis, dysmenorrhea, Irritable bowel syndrome, Crohn's disease, ureteral colic and myocardial infarction.

Furthermore, the term "pain" comprises pain associated with CNS disorders comprising: multiple sclerosis, spinal cord injury, traumatic brain injury, Parkinson's disease and stroke.

In a preferred embodiment, "pain" relates to chronic pain types comprising headache (for example migraine disorders, episodic and chronic tension-type headache, tension-type like headache, cluster headache, and chronic paroxysmal hemicrania), low back pain, cancer pain, osteoarthritis pain and neuropathic pain, but is not limited thereto.

Inflammatory pain (pain in response to tissue injury and the resulting inflammatory process) as defined herein relates to inflammatory pain associated with diseases comprising connective tissue diseases, rheumatoid arthritis, systemic lupus erythematosus, multiple sclerosis and arthritis, but is not limited thereto.

Neuropathic pain (pain resulting from damage to the peripheral nerves or to the central nervous system itself) includes conditions comprising, but not limited to metabolic neuropathies (e.g., diabetic neuropathy), post-herpetic neuralgia, trigeminal neuralgia, cranial neuralgia, post-stroke neuropathic pain, multiple sclerosis-associated neuropathic pain, HIV/AIDS-associated neuropathic pain, cancer-associated neuropathic pain, carpal tunnel-associated neuropathic pain, spinal cord injury-associated neuropathic pain, complex regional pain syndrome, fibromyalgia-associated neuropathic pain, reflex sympathetic dystrophy, phantom limb syndrome or peripheral nerve or spinal cord trauma, nerve transection including surgery, limb amputation and stump pain, pain caused by the side effects of anti-cancer and anti-AIDS therapies, post-surgical neuropathic pain, neuropathy-associated pain such as in idiopathic or post-traumatic neuropathy and mononeuritis, and neuropathic pain caused by connective tissue disease such as rheumatoid arthritis, Wallenberg's syndrome, systemic lupus erythematosus, multiple sclerosis, or polyarteritis nodosa. The neuropathy can be classified as radiculopathy, mononeuropathy, mononeuropathy multiplex, polyneuropathy or plexopathy.

The term "allodynia" denotes pain arising from stimuli which are not normally painful. Allodynic pain may occur other than in the area stimulated.

The term "hyperalgesia" denotes an increased sensitivity to a painful stimulus.

The term "hypoalgesia" denotes a decreased sensitivity to a painful stimulus.

The role of CDK9 in the development of pain could be based on the following mechanism of action, although it must be stressed that the effectiveness of the invention does not depend upon the correct identification of the mechanism. Both cyclin T1 and CDK9 stimulate the basal promoter activity of TNFα. TNFα is a pro-inflammatory cytokine and pain mediator that controls expression of inflammatory genetic networks. For mediation of cellular TNF receptor responses, several inducible transcription factors have been shown to be crucial. TNFα triggers its recruitment to cytokine genes while transcription factors interact with the p-TEFb complex for stimulation of gene transcription (Barboric, M. et al., Mol Cell, 2001, 8, 327-337). Additionally, it has been shown that CDK9 is a binding partner of TRAF2, a member of the TNFα receptor complex (MacLachlan, T. K. et al., J Cell Biochem. 1998, 71, 467-478), while GP130, a subunit of the pro-inflammatory IL6 receptor complex has recently been identified as another potential binding partner of CDK9 (Falco, G. D. et al., Oncogene. 2002, 21, 7464-7470). As a key player in TNFα-mediated expression of several genes (e.g. cytokines as pain mediators), CDK9 can thus be considered as a central target for the treatment of any type of pain, such as inflammatory pain.

For the treatment of neuropathic pain, pharmacological action has to take place beyond the blood-brain-barrier (BBB) in the central nervous system (CNS). Microglial cells as the principal immune cells in the CNS, for example, release, upon activation, a variety of noxious factors such as cytokines (TNFα, IL1β, IL6) and other pro-inflammatory molecules (Huwe 2003). Microglia are activated by stimulation of TNFα receptor or Toll-like leading to transcriptional activation of the cytokines described above. Microglial contribution has been discussed as instrumental in chronic CNS diseases and may contribute to pain perception.

Recently it has been shown that inducible transcription factors regulate expression of Cyclooxygenase-2 (COX-2) via Interleukin 1β (IL1β) in the spinal cord (Lee et al. 2004). As the major contributor to elevation of spinal prostaglandin E2, the pain mediator COX-2 is already known as a target for a variety of anti-nociceptive/anti-inflammatory drugs. In contrast to COX-2, inhibition of CDK9 action would lead to suppression of a variety of pain mediators instead of just a single one. Thus, anti-nociceptive action of CDK9 inhibitors may be superior compared to, e.g. COX-2 inhibitors.

Inflammatory Diseases

Surprisingly, it could be shown that the CDK inhibiting compounds according to Formula (I) as disclosed herein exert an anti-inflammatory effect in in vitro and in vivo inflammatory assays.

Thus, in a further aspect of the invention, there is provided a compound of Formula (I) for use in the treatment of inflammatory diseases.

There is also provided the use of a compound of formula (I) in the preparation of a medicament for the treatment of inflammatory diseases.

Furthermore, the invention provides a method of treating inflammatory diseases comprising administering to a subject in need of such treatment an effective amount of a compound of Formula (I).

It is particularly surprising that even compounds of Formula (I) displaying an increased selectivity for CDK9 over other CDKs exert anti-inflammatory effects. This finding teaches against the recently consolidated believe that a pleiotropic action on several CDK family members is a desirable feature of CDK inhibitors used to treat inflammatory disorders (Leitch, A., Haslett, C. and Rossi, A., Br J. Pharmacol. 2009, 158, 1004-1016). In contrast to the previously proposed view that pan-selectivity of CDK inhibitors is beneficial for achieving therapeutic success in inflammatory disorders and that single-hit therapies are expected to prove ineffectual, our results with compounds of Formula (I) displaying an increased selectivity for CDK9 over other CDKs surprisingly shows that the preferred inhibition of CDK9 is able to mediate strong anti-inflammatory effects, including transcriptional inhibition of pro-inflammatory mediators and anti-proliferative and/or pro-apoptotic effects on immunologically relevant cell types.

The role of CDK9 in the development of inflammatory diseases could be based on the following mechanism of action: inflammatory diseases such as rheumatoid arthritis (RA); atherosclerosis; asthma; inflammatory bowel disease, systemic lupus erythematosus and several other autoimmune diseases are mediated by tumor necrosis factor α (TNFα), a key regulator of inflammatory and tissue obstructive pathways in said diseases. It is known that the TNFα signal is mediated via several transducers and results in transcriptional regulation of response genes. Several transcription factors have been shown to bind and recruit CDK9 to inducible promoters, where it catalyzes the phosphorylation of the CTD of RNA Pol II (West, M. J. et al., Journal of Virology 2001, 75, 8524-8537). Resulting hyperphosphorylation of the RNA Pol II CTD leads to transcriptional induction of pro-inflammatory cytokines such as IL-1B, 1L-6 and IL-8 that are also known as being regulated by TNFα.

Several studies showed that TNFα is a 'master regulator' of an autologous signaling cascade that regulates pro-inflammatory cytokine expression. To interrupt this pro-inflammatory cascade, specific antibodies (Abs) can be used successfully to block the TNFα signal. Anti-TNFα treatment of RA with Abs has already proven its therapeutic efficacy in several clinical studies and FDA approved drugs such as Infliximab and Etanercept have entered the market (Feldmann and Maini, Nat-Med, 2003, 9, 1245-1250). However, disadvantages of Ab based therapies include their immunogenic potential, attendant loss of efficacy during progressive treatment and high treatment costs. Additionally, the Ab kinetics permits a more or less all-or-nothing reduction of circulating TNFα. As a result, physiologic functions of the immune response are also suppressed (Laufer, S. et al., Inflammation and Rheumatic Diseases, 2003, Thieme, 104-105).

Therapeutic interventions into the TNFα-mediated signaling cascade with kinase inhibitors aiming at targets such as p38 MAPK or IKK have shown severe adverse effects—in most cases due to a lack of specificity against the respective target.

In contrast thereto, CDK specific inhibitors according to Formula (I) as presented herein may intervene at the very bottom end of the TNFα signaling pathways reducing the interaction with physiological functions. Additionally, said compounds will allow interruption of the autologous TNFα mediated inflammatory network by avoidance of adverse effects via superior specificity. Therefore, treatment with CDK specific inhibitors of Formula (I) constitutes a promising strategy for the treatment of inflammatory and autoimmune diseases.

Thus, the compounds according to Formula (I) as presented herein may be used for the treatment of inflammatory diseases.

The term "inflammatory diseases" as used herein relates to diseases triggered by cellular or non-cellular mediators of the immune system or tissues causing the inflammation of body tissues and subsequently producing an acute or chronic inflammatory condition.

Examples for such inflammatory diseases are hypersensitivity reactions of type I-IV, for example, but not limited to hypersensitivity diseases of the lung including asthma, atopic diseases, allergic rhinitis or conjunctivitis, angioedema of the lids, hereditary angioedema, antireceptor hypersensitivity reactions and autoimmune diseases, Hashimoto's thyroiditis, systemic lupus erythematosus, Goodpasture's syndrome, pemphigus, myasthenia gravis, Grave's and Raynaud's disease, type B insulin-resistant diabetes, rheumatoid arthritis, psoriasis, Crohn's disease, scleroderma, mixed connective tissue disease, polymyositis, sarcoidosis, Wegener's granulomatosis, glomerulonephritis, acute or chronic host versus graft reactions.

Furthermore, the term "inflammatory diseases" includes but is not limited to abdominal cavity inflammation, dermatitis, gastrointestinal inflammation (including inflammatory bowel disease, ulcerative colitis), fibrosis, ocular and orbital inflammation, dry eye disease and severe dry eye disease resulting from Sjörgen's syndrome, mastitis, otitis, mouth inflammation, musculoskeletal system inflammation (including gout, osteoarthritis), inflammatory diseases of the central nervous system (including multiple sclerosis, bacterial meningitis, meningitis), genitourinary tract inflammation (including prostatitis, glomerulonephritis), cardiovascular inflammation (including atherosclerosis, heart failure), respiratory tract inflammation (including chronic bronchitis, chronic obstructive pulmonary disease), thyroiditis, diabetes mellitus, osteitis, myositis, multiple organ failure (including sepsis), polymyositis and psoriatic arthritis.

Immunological Diseases

The compounds according to Formula (I) are also useful in the treatment and/or prevention of immunological diseases, such as, for example, autoimmune diseases.

Accordingly, the present invention provides a compound of formula (I) for use in the treatment of immunological diseases, for example autoimmune diseases.

Furthermore, there is provided the use of a compound of formula (I) in the preparation of a medicament for the treatment of immunological diseases, for example autoimmune diseases.

The invention also provides a method for the treatment of immunological diseases, for example autoimmune diseases, comprising administering to a subject in need of such treatment an effective amount of a compound Formula (I).

The term "immunological diseases" as used herein relates to diseases including but not limited to allergy, asthma, graft-versus-host disease, immune deficiencies and autoimmune diseases.

Specifically, immunological diseases include diabetes, rheumatic diseases, AIDS, chronic granulomatosis disease, rejection of transplanted organs and tissues, rhinitis, chronic obstructive pulmonary diseases, osteoporosis, ulcerative colitis, Crohn's disease, sinusitis, lupus erythematosus, psoriasis, multiple sclerosis, myasthenia gravis, alopecia, recurrent infections, atopic dermatitis, eczema and severe anaphylactic reactions, but are not limited thereto.

Furthermore, "immunological diseases" also include allergies such as contact allergies, food allergies or drug allergies.

Proliferative Diseases

The compounds of Formula (I) are inhibitors of cyclin-dependent kinases, which represent key molecules involved in regulation of the cell-cycle. Cell-cycle disregulation is one of the cardinal characteristics of neoplastic cells. Thus, said compounds are expected to prove useful in arresting or recovering control of the cell-cycle in abnormally dividing cells. It is thus expected that the compounds according to Formula (I) are useful in the treatment and/or prevention of proliferative diseases such as cancer.

Accordingly, the invention provides a compound of formula (I) for use in the treatment of proliferative diseases.

There is also provided the use of a compound of formula (I) in the preparation of a medicament for the treatment of proliferative diseases.

In addition, the invention relates to a method for the treatment of proliferative diseases comprising administering to a subject in need of such treatment an effective amount of a compound Formula (I).

As used herein, the term "proliferative disease" relates to cancer disorders, including, but not limited to benign neoplasms, dysplasias, hyperplasias as well as neoplasms showing metastatic growth or any other transformations.

The term "cancer" includes but is not limited to benign and malign neoplasia like carcinoma, sarcoma, carcinosarcoma, cancers of the blood-forming tissues, tumors of nerve tissues including the brain and cancer of skin cells.

Examples of cancers which may be treated include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas (e.g. exocrine pancreatic carcinoma), stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronicmyelogenous leukemias, myelodysplastic syndrome, or promyelocytic leukemia; thyroid follicular cancer; a tumour of mesenchymal origin, for example fibrosarcoma or habdomyosarcoma; a tumor of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; Kaposi's sarcoma, astrocytoma, basal cell carcinoma, small intestine cancer, small intestinal tumors, gastrointestinal tumors, glioblastomas, liposarcoma, germ cell tumor, head and neck tumors (tumors of the ear, nose and throat area), cancer of the mouth, throat, larynx, and the esophagus, cancer of the bone and its supportive and connective tissues like malignant or benign bone tumour, e.g. malignant osteogenic sarcoma, benign osteoma, cartilage tumors; like malignant chondrosarcoma or benign chondroma, osteosarcomas; tumors of the urinary bladder and the internal and external organs and structures of the urogenital system of male and female, soft tissue tumors, soft tissue sarcoma, Wilm's tumor or cancers of the endocrine and exocrine glands like e.g. thyroid, parathyroid, pituitary, adrenal glands, salivary glands.

Infectious Diseases

Furthermore, the invention relates to a compound of formula (I) for use in the treatment of infectious diseases.

In another aspect, there is provided the use of a compound of formula (I) in the manufacture of a medicament for the treatment of infectious diseases.

The invention further provides a method of treating infectious diseases comprising administering to a subject in need of such treatment an effective amount of a compound of Formula (I).

It is known that certain host cell CDKs are involved in viral replication, i.e. CDK2, CDK7, CDK8 and CDK9 (Wang, D. et al., J. Virol. 2001, 75, 7266-7279). Specifically, the role of CDK9 kinase activity in regulation of HIV-1 transcription elongation and histone methylation has been described (Zhou, M. et al., J. Virol 2004, 78, 13522-13533).

In a preferred embodiment, the invention thus relates to a method of treating and/or preventing infectious diseases comprising administering an effective amount of at least one inhibitor of a cyclin-dependent kinase according to Formula (I), wherein said compound displays an increased selectivity for CDK9 than for other CDKs.

The term "infectious diseases" as used herein comprises infections caused by pathogens such as viruses, bacteria, fungi and/or parasites.

Virus-induced infectious diseases include diseases caused by infection with retroviruses, human endogenous retroviruses, hepadnaviruses, herpesviruses, flaviviruses, adenoviruses, togaviruses and poxviruses. Specifically, infectious diseases are caused by viruses comprising, but not limited to viruses such as HIV-1, HIV-2, HTLV-I and HTLV-II, hepadnaviruses such as HBV, herpesviruses such as Herpes simplex virus I (HSV I), herpes simplex virus 11 (HSV II), Epstein-Barr virus (EBV), varicella zoster virus (VZV), human cytomegalovirus (HCMV) or human herpesvirus 8 (HHV-8), flaviviruses such as HCV, West nile or Yellow Fever virus, human papilloma virus, poxviruses, Sindbis virus or adenoviruses. Examples of infectious diseases include, but are not limited to AIDS, borreliosis, botulism, diarrhea, BSE (Bovine Spongiform Encephalopathy), chikungunya, cholera, CJD (Creutzfeldt-Jakob Disease), conjunctivitis, cytomegalovirus infection, dengue/dengue Fever, encephalitis, eastern equine encephalitis, western equine encephalitis, Epstein-Barr Virus Infection, *Escherichia coli* Infection, foodborne infection, foot and mouth disease, fungal dermatitis, gastroenteritis, *Helicobacter pylori* Infection, Hepatitis (HCV, HBV), Herpes Zoster (Shingles), HIV Infection, Influenza, malaria, measles, meningitis, meningoencephalitis, molluscum contagiosum, mosquito-borne Diseases, Parvovirus Infection, plague, PCP (*Pneumocystis carinii* Pneumonia), polio, primary gastroenteritis, Q Fever, Rabies, Respiratory Syncytial Virus (RSV) Infection, rheumatic fever, rhinitis, Rift Valley Fever, Rotavirus Infection, salmonellosis, *salmonella enteritidis*, scabies, shigellosis, smallpox, streptococcal infection, tetanus, Toxic Shock Syndrome, tuberculosis, ulcers (peptic ulcer disease), hemorrhagic fever, variola, warts, West Nile Virus Infection (West Nile Encephalitis), whooping cough, yellow fever.

Cardiovascular Diseases

In another aspect, the invention relates to a compound of formula (I) for use in the treatment of cardiovascular diseases.

The invention also relates to the use of a compound of formula (I) in the manufacture of a medicament for the treatment of cardiovascular diseases.

Furthermore, the invention relates to the treatment of cardiovascular diseases comprising administering to a subject in need of such treatment an effective amount of at least one inhibitor of a compound of Formula (I).

It has been reported that the field of cardiovascular diseases constitutes a possible clinical application for CDK inhibitors (Meijer, L. et al., Pharmacol Ther 1999, 82, 279-284). Furthermore, it is known that inhibition of the cyclin T/CDK9 complex and more specifically, inhibition of CDK9 may play a beneficial role in the treatment of cardiovascular diseases such as heart failure (WO2005/027902).

Thus, the compounds of formula (I), which display increased selectivity for CDK9 over other CDKs, are of particular use in the treatment of cardiovascular diseases.

The term "cardiovascular diseases" includes but is not limited to disorders of the heart and the vascular system like congestive heart failure, myocardial infarction, ischemic diseases of the heart, such as stable angina, unstable angina and asymptomatic ischemia, all kinds of atrial and ventricular arrhythmias, hypertensive vascular diseases, peripheral vascular diseases, coronary heart disease and atherosclerosis. Furthermore, as used herein, the term includes, but is not limited to adult congenital heart disease, aneurysm, angina pectoris, angioneurotic edema, aortic valve stenosis, aortic aneurysm, aortic regurgitation, arrhythmogenic right ventricular dysplasia, arteriovenous malformations, atrial fibrillation, Behcet syndrome, bradycardia, cardiomegaly, cardiomyopathies such as congestive, hypertrophic and restrictive cardiomyopathy, carotid stenosis, cerebral hemorrhage, Churg-Strauss syndrome, cholesterol embolism, bacterial endocarditis, fibromuscular dysplasia, congestive heart failure, heart valve diseases such as incompetent valves or stenosed valves, heart attack, epidural or subdural hematoma, von Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, mitral valve prolapse, long QT syndrome mitral valve prolapse, myocardial ischemia, myocarditis, disorders of the pericardium, pericarditis, peripheral vascular diseases, phlebitis, polyarteritis nodosa, pulmonary atresia, Raynaud disease, restenosis, rheumatic heart disease, Sneddon syndrome, stenosis, superior vena cava syndrome, syndrome X, tachycardia, hereditary hemorrhagic telangiectasia, telangiectasis, temporal arteritis, thromboangiitis obliterans, thrombosis, thromboembolism, varicose veins, vascular diseases, vasculitis, vasospasm, ventricular fibrillation, Williams syndrome, peripheral vascular disease, varicose veins and leg ulcers, deep vein thrombosis and Wolff-Parkinson-White syndrome.

Furthermore, the term cardiovascular diseases includes diseases resulting from congenital defects, genetic defects, environmental influences (i.e., dietary influences, lifestyle, stress, etc.), and other defects or influences.

Neurodegenerative Diseases

CDK inhibitors have been described to exert neuroprotective effects. Specifically, it has been reported that CDK inhibitors prevent neuronal death in neurodegenerative diseases such as Alzheimer's disease (Filgueira de Azevedo, W. Jr., Biochem Biophys Res Commun 2002, 297, 1154-1158; Knockaert, M. et al., Trends Pharmacol Sci 2002, 23, 417-425; Meijer, L. et al., Pharmacol Ther 1999, 82, 279-284).

Thus, the compounds according to Formula (I), which are CDK inhibitors, are expected to provide beneficial effects in the therapeutic management of neurodegenerative diseases.

Accordingly, the invention relates to a compound of formula (I) for use in the treatment of neurodegenerative diseases.

Further, the invention provides the use of a compound of formula (I) in the manufacture of a medicament for the treatment of neurodegenerative diseases.

The invention also provides a method of treating neurodegenerative diseases comprising administering to a patient in need of such treatment an effective amount of a compound Formula (I).

The term "neurodegenerative diseases" as used herein includes disorders of the central nervous system as well as disorders of the peripheral nervous system, including, but not limited to brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease, dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, Korsakoff's psychosis and AIDS-related dementia.

Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be neurodegenerative disorders.

Specifically, the present invention relates to a method for treating the above-referenced types of pain and associated conditions and inflammatory disorders, immunological diseases, proliferative diseases, infectious diseases, cardiovascular diseases and neurodegenerative diseases, wherein the term "treating" comprises the prevention, amelioration or treating of pain and associated conditions and inflammatory disorders, immunological diseases, proliferative diseases, infectious diseases, cardiovascular diseases and neurodegenerative diseases.

When used to treat one or more of the conditions specified above, the compound of general formula (I) may be used in combination with one or more other compound of formula (I) or with one or more additional agents for the treatment of pain, inflammatory disorders, immunological diseases, proliferative diseases, infectious diseases, cardiovascular diseases and neurodegenerative diseases. Such agents are well known to those of skill in the art.

Pharmaceutical Compositions

In yet another aspect of the invention there is provided a pharmaceutical composition comprising a compound of Formula (I) as active ingredient together with at least one pharmaceutically acceptable (i.e. non-toxic) carrier, excipient and/or diluent.

Furthermore, the invention also comprises compositions combining at least two inhibitors of CDK and/or pharmaceutically acceptable salts thereof. Said at least two inhibitors may inhibit the same cyclin-dependent kinase or may also inhibit different types of cylin-dependent kinases, e.g. one inhibitor in the composition may inhibit CDK9 while the other inhibitor is capable of inhibiting CDK2, for example.

Having regard to pain treatment, an individual pain medication often provides only partially effective pain alleviation because it interferes with just one pain-transducing pathway out of many. Thus, compounds of Formula (I) may be administered in combination with a pain-reducing (analgesic) agent that acts at a different point in the pain perception process.

An "analgesic agent" comprises a molecule or combination of molecules that causes a reduction in pain perception. An analgesic agent employs a mechanism of action other than inhibition of CDK.

One class of analgesics, such as nonsteroidal anti-inflammatory drugs (NSAIDs), down-regulates the chemical messengers of the stimuli that are detected by the nociceptors and another class of drugs, such as opioids, alters the processing of nociceptive information in the CNS. Other analgesics are local anesthetics, anticonvulsants and antidepressants such as tricyclic antidepressants. Administering one or more classes of drug in addition to CDK inhibitors can provide more effective amelioration of pain.

Preferred NSAIDs for use in the methods and compositions of the present invention are aspirin, acetaminophen, ibuprofen, and indomethacin. Furthermore, cyclooxygenase-2 (COX-2) inhibitors, such as specific COX-2 inhibitors (e.g. celecoxib, COX189, and rofecoxib) may also be used as an analgesic agent in the methods or compositions of the present invention.

Preferred tricyclic antidepressants are selected from the group consisting of Clomipramine, Amoxapine, Nortriptyline, Amitriptyline, Imipramine, Desipramine, Doxepin, Trimipramine, Protriptylin, and Imipramine pamoate.

Furthermore, the use of anticonvulsants (e.g. gabapentin), GABAB agonists (e.g. L-baclofen), opioids, vanniloid receptor antagonists and cannabinoid (CB) receptor agonists, e.g. CBI receptor agonists as analgesic is also preferred in the methods and compositions in the present invention.

In preparing cyclin-dependent kinase inhibitor compositions of this invention, one can follow the standard recommendations of well-known pharmaceutical sources such as Remington: The Science and Practice of Pharmacy, $19^{th}$ ed. (Mack Publishing, 1995).

The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, wherein said preparations in addition to typical vehicles and/or diluents contain at least one inhibitor according to the present invention and/or a pharmaceutical acceptable salt thereof as active ingredient.

The pharmaceutical compositions according to the present invention containing at least one compound of formula (I) and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like.

Moreover, suitable binders, lubricants, disintegrating agents and coloring agents may also be incorporated into the tablet or capsule. Powders and tablets may contain about 5 to about 95% by weight of a cyclin-dependent kinase inhibitor according to the Formula (I) as recited herein or analogues thereof or the respective pharmaceutical active salt as active ingredient.

Suitable binders include without limitation, starch, gelatin, natural sugars such as glucose or betalactose, corn sweeteners, natural and synthetic gums such as acacia, tragacanth or sodium oleate, sodium alginate, carboxymethylcellulose, polyethylene glycol and waxes. Among suitable lubricants there may be mentioned boric acid, sodium stearate, magnesium stearate, sodium benzoate, sodium acetate, sodium chloride, and the like.

Suitable disintegrants include starch, methylcellulose, agar, bentonite, xanthan gum, guar gum, and the like.

Sweetening and flavoring agents as well as preservatives may also be included, where appropriate. The disintegrants, diluents, lubricants, binders etc. are discussed in more detail below.

Soluble polymers as targetable drug carriers can include polyvinylpyrrolidone, pyran copolymer, polyhydroxypropylmethacrylamidephenol, polyhydroxyethylaspartamidephenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Moreover, the pharmaceutical compositions of the present invention may be formulated in sustained release form to provide the rate controlled release of any one or more of the components or active ingredients to optimise the therapeutic effect (s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration.

Aerosol preparations suitable for inhalation may include solutions and solids in powder form, which may be present in combination with a pharmaceutically acceptable carrier such as an inert, compressed gas, e.g. nitrogen.

For preparing suppositories, a low melting wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermal. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methylcellulose, polyvinyl alcohols, or denatured gelatins or starch for holding or containing compositions comprising the active ingredient(s). Capsules with hard shells are typically made of blended or relatively high gel strength gelatins from bones or pork skin. The capsule itself may contain small amounts of dyes, opaquing agents, plasticisers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix.

Powders for constitution comprise powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75% by weight, and more suitably from about 30 to about 60% by weight.

The term disintegrants refers to materials added to the composition to support disintegration and release of the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium-croscaramellose, alginates such as alginic acid and sodium alginate, clays such as bentonites, and effervescent mixtures. The amount of disintegrant in the composition may range from about 2 to about 20% by weight of the composition, more suitably from about 5 to about 10% by weight.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20% by weight of the composition, suitably from about 3 to about 10% by weight, and more suitably from about 3 to about 6% by weight.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D, L-leucine. Lubricants are usually added at the very last step before compression, since they must be present at the surface of the granules. The amount of lubricant in the composition may range from about 0.2 to about 5% by weight of the composition, suitably from about 0.5 to about 2% by weight, and more suitably from about 0.3 to about 1.5% by weight of the composition.

Glidents are materials that prevent baking of the components of the pharmaceutical composition together and improve the flow characteristics of granulate so that flow is smooth and uniform. Suitable glidents include silicon dioxide and talc.

The amount of glident in the composition may range from about 0.1 to about 5% by weight of the final composition, suitably from about 0.5 to about 2% by weight.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5% by weight of the composition, suitably from about 0.1 to about 1% by weight.

The present invention relates to the administration of compositions containing as active ingredient a cyclin-dependent kinase inhibitor to a subject in need thereof for the treatment of any type of pain, inflammatory disorders, immunological diseases, proliferative diseases, cardiovascular diseases or neurodegenerative diseases.

"A subject in need thereof" comprises an animal, suitably a mammal, and most suitably a human, expected to experience any type of pain, inflammatory disorders, immunological diseases, proliferative diseases, cardiovascular diseases or neurodegenerative diseases in the near future or which has ongoing experience of said conditions. For example, such animal or human may have an ongoing condition that is causing pain currently and is likely to continue to cause pain, or the animal or human has been, is or will be enduring a procedure or event that usually has painful consequences. Chronic painful conditions such as diabetic neuropathic hyperalgesia and collagen vascular diseases are examples of the first type; dental work, particularly in an area of inflammation or nerve damage, and toxin exposure (including exposure to chemotherapeutic agents) are examples of the latter type.

In order to achieve the desired therapeutic effect, the respective cyclin-dependent kinase inhibitor has to be administered in a therapeutically effective amount.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician, and includes alleviation of the symptoms of the disease being treated. In the context of the present invention, a therapeutically effective amount comprises, e.g., an amount that reduces pain, in particular inflammatory or neuropathic pain. Specifically, a therapeutically effective amount denotes an amount which exerts a hypoalgesic effect in the subject to be treated.

Such effective amount will vary from subject to subject depending on the subject's normal sensitivity to, e.g., pain, its height, weight, age, and health, the source of the pain, the mode of administering the inhibitor of CDKs, the particular inhibitor administered, and other factors. As a result, it is advisable to empirically determine an effective amount for a particular subject under a particular set of circumstances.

EXAMPLES

General Methods for the Preparation of the Compounds

Analytical Methods

NMR spectra were performed on a Bruker AM 400 spectrometer or on a Varian 400 MHz Mercury Plus spectrometer. The following abbreviations are used: s (singlet), d (doublet), dd (doublet of doublet), t (triplet), and m (multiplet). ESI-MS: Mass spectra were taken with an MDS Sciex API 365 mass spectrometer equipped with an Ionspray™ interface (MDS Sciex, Thorn Hill, ON, Canada). The instrument settings, data acquisition and processing were controlled by the Applied Biosystems (Foster City, Calif., USA) Analyst™ software for Windows NT™. 50-100 scans were performed by the positive ionization Q1 scan mode to accumulate the peaks. Sample solutions were diluted with 50% MeOH in 0.5% formic acid to reach concentrations about 10 µg/ml. Each sample solution was introduced directly by a microsyringe (1 ml) through an infusion pump (Havard Apperatus 22, Havard Instruments, Holliston, Mass., USA) and fused silica capillary tubing at a rate of 20 ul/min. Thin layer chromatography (TLC) was done using Macherey Nagel Polygram® SIL G/UV$_{245}$. Visualisation was accomplished by means of UV light at 254 nm, followed by dyeing with potassium permanganate or ninhydrin. Solvents were distilled prior to use. All commercially available reagents were used without further purification. The pH-7 buffer solution used in the workup procedures was prepared by dissolving potassium dihydrogen phosphate (85.0 g) and sodium hydroxide (14.5 g) in water (1 l). Analytical HPLC was performed using a Merck-Hitachi device: AcN-water (flow rate: 1 ml min$^{-1}$), column: LiChrosphere 5 um RP18e, 125×4.0 mm (Merck), pump: L-7100 Merck-Hitachi was used. Gradient A was used for the detection of the purified compounds in the examples. Characterisation of gradient A: starting from AcN-water (5/95) at t=0 min to AcN-water (50/50) within 15 min, to AcN-water (95/5) after additional 5 min, remaining for additional 3 min at AcN-water (95/5). Several methods for preparative purification were used, the appropriate method was noted in the experimental data.

General Abbreviations

AcN Acetonitrile

ATP Adenosine-5'-triphosphate

Boc tert.-Butyloxycarbonyl

CHCl$_3$ Chloroform cone. concentrated
Cs$_2$CO$_3$ Cesium carbonate
DCM Dichloromethane
DIPEA Diisopropylethylamine
DEA Diethylamine
DMSO Dimethylsulfoxide
ESI-MS Electrospray Mass Spectroscopy
EtOH Ethanol
HATU 2-(1H-7-Azabenzotriazol-1-yl)-1,1,3,3-tetramethyl-uronium-hexafluoro-phosphate
HCl hydrochloric acid
HPLC High Performance Liquid Chromatography
IPA Isopropyl alcohol
MeOH methanol
MHz Megahertz
min minutes
mp Melting point
NMR Nuclear magnetic resonance
rt Retention time
UV ultraviolet
THF Tetrahydrofuran
TFA Trifluoroacetic acid
TLC Thin Layer Chromatography
xantphos 4,5-Bis(diphenylphosphino)-9,9-dimethyxanthene General Approach for the Preparation of Examples, Preparation of the Starting Materials, and General Methods General Approach for the Preparation of Examples The here described examples were synthesized by HATU coupling starting from compound I with the appropriate carboxylic acid (according to Method A) or by Buchwald type reaction starting from compounds of type II with the appropriate amide (according to Method B).

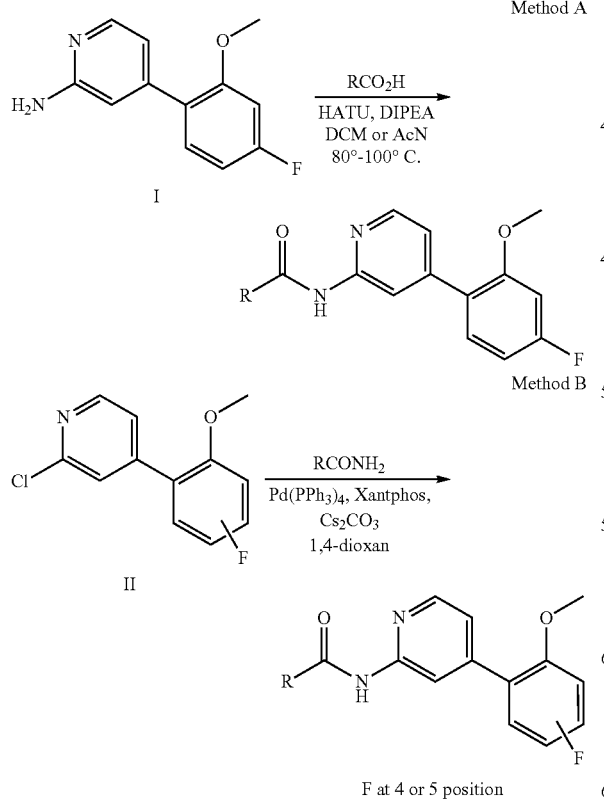

Preparation of the Starting Materials

Preparation of 4-(4-fluoro-2-methoxyphenyl)pyridin-2-amine (I)

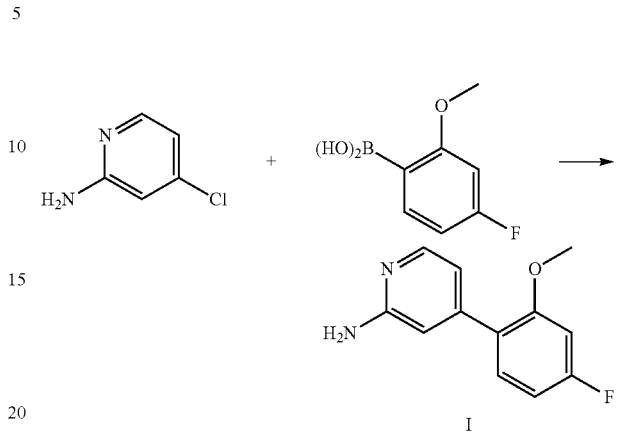

2-Amino-4-chloro-pyridine (5.00 g, 38.9 mmol) and 4-fluoro-2-methoxyphenylboronic acid (9.26 g, 54.4 mmol) were taken in 1,2-dimethoxy ethane (100 ml). An aqueous solution of sodium carbonate (80 ml, 2 M) was added and argon gas was purged for 30 min. Bis-(triphenyl phosphine) palladium (II) chloride (Pd(PPh$_3$)$_2$Cl$_2$) (272 mg, 0.39 mmol) was added to the reaction mixture and again purged with argon gas for 20 min. The reaction mixture was slowly heated to 85° C.-90° C. with stirring and maintained for 8 h. On completion of reaction, the reaction mixture was cooled to room temperature and the insoluble solid residue filtered. The filtrate was concentrated until 1,2-dimethoxy ethane was fully evaporated. Excess iced-water was added to precipitate the product which was filtered, washed with copious amount of water, and dried under vacuo at 60° C. Again this solid crude product was washed with ethyl acetate in petroleum ether (10%) and dried to afford 20 g (88%) of compound I.

Preparation of 2-chloro-4-(4-fluoro-2-methoxyphenyl)pyridine, general procedure for the preparation of pyridines for method B

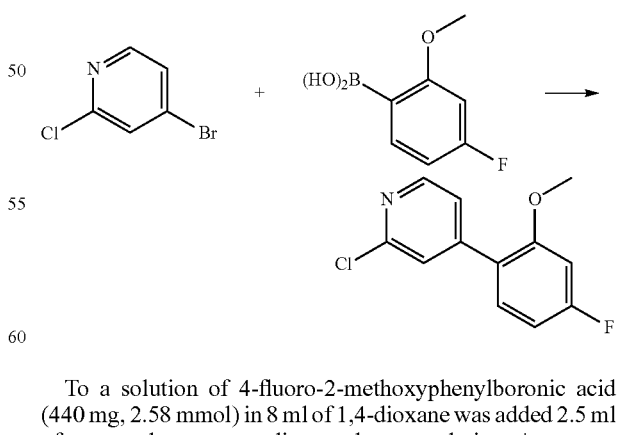

To a solution of 4-fluoro-2-methoxyphenylboronic acid (440 mg, 2.58 mmol) in 8 ml of 1,4-dioxane was added 2.5 ml of saturated aqueous sodium carbonate solution. Argon gas was purged for 30 min at room temperature. 4-Bromo-2-chloropyridine (500 mg, 2.58 mmol) and tetrakis(triphenylphosphine)palladium (0) (150 mg, 0.129 mmol) were added to reaction mixture simultaneously and argon gas was bubbled for another 40 min. The reaction mixture was heated to reflux for 16 h, TLC confirms completion of reaction and the mixture was concentrated under reduced pressure. The residue was partitioned between DCM and water. The organic layer was separated, washed with brine, water, dried (Na₂SO₄) and concentrated. The obtained crude residue was purified through silica gel column chromatography eluting with 15% ethyl acetate in DCM to provide 2-chloro-4-(4-fluoro-2-methoxyphenyl)pyridine (450 mg, 73.3%).

Preparation of
2-chloro-4-(5-fluoro-2-methoxyphenyl)pyridine

Compound 2-chloro-4-(5-fluoro-2-methoxyphenyl)pyridine was synthesized starting from 5-fluoro-2-methoxyphenylboronic acid according to the procedure given above in a yield of 66.4%.

General Methods

Method A: (via HATU Coupling)

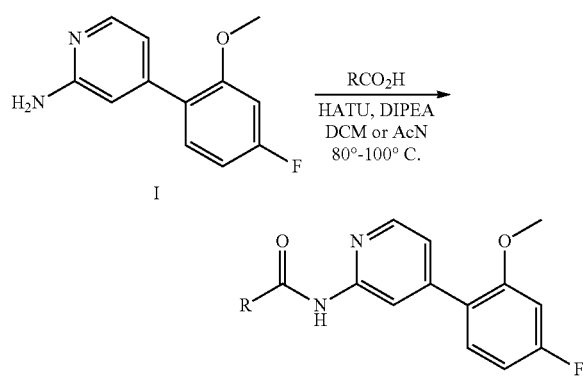

DIPEA (2 eq.) was added to a solution of an carboxylic acid RCOOH (1 eq.) in DCM or AcN and stirred for 15-20 min in a sealed tube. HATU (1 eq.) was added and the mixture was purged with argon for 10 min. The reaction mass was stirred at room temperature till a clear solution ensued. Amine I (1 eq.) was added, the mixture purged again for 10 min and then heated at 80-100° C. in sealed tube for 2-18 h. The reaction mixture was cooled, quenched with pH-7 buffer solution. The organic layer was separated and the aqueous layer extracted with DCM. The combined organic layers were washed successively with water and brine, dried (Na₂SO₄) and concentrated in vacuo to a crude residue. The residue was subjected to either preparative TLC/HPLC to isolate the pure compound.

Method B: (Via Buchwald Type Reaction on Amides)

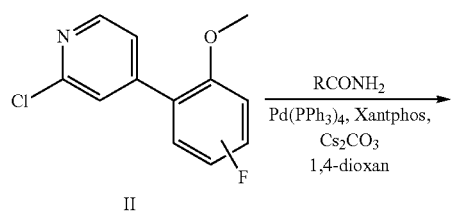

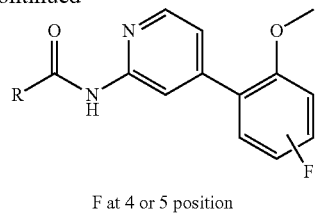

F at 4 or 5 position

Tetrakis(triphenylphosphine)palladium (0) (5 mol %) was added to a mixture of amide RCONH₂ (1 eq.) and the appropriate 4- or 5-fluorinated compound of type II (1 eq.) in dry 1,4-dioxane in a dry sealed tube and purged with argon for 15 min. Cesium carbonate (2 eq.) and Xantphos (10 mol %) were added and the whole mass purged again with argon for 15 min and sealed. The reaction mixture was then heated at 120° C. for 3-6 h, before cooling to room temperature. It was then poured into an excess of water and extracted with ethyl acetate. The organic layer was washed with water, brine, dried (Na₂SO₄) and concentrated to dryness in vacuo. The residue so obtained was subjected to preparative TLC/HPLC to afford the pure compounds.

Method C: (Via Deprotection Under Acid Conditions by Means of TFA)

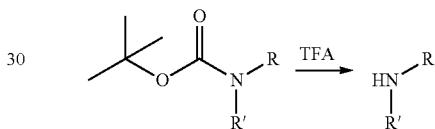

To a solution of the Boc-protected compound (0.1 mmol) in a small amount of DCM was added a mixture of TFA/DCM (4 ml, 1:1). This solution was stirred for 2 h at room temperature before the solvents were removed under reduced pressure. The resulted residue was purified by preparative TLC/HPLC.

Method D: (Via Chan-Lam Coupling)

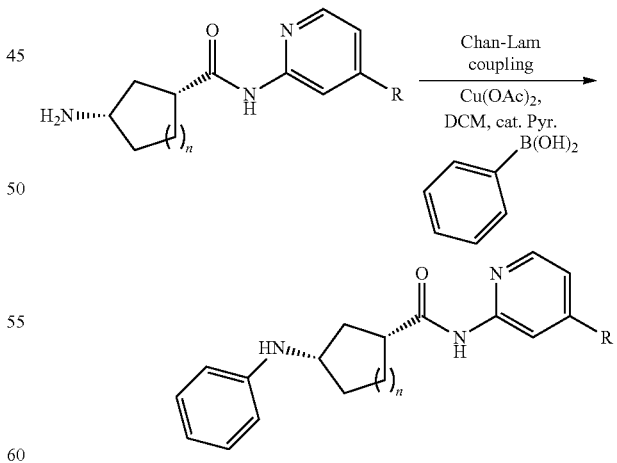

Phenyl boronic acid (900 mg, 4.10 mmol), copper acetate (746 mg, 4.10 mmol) and pyridine (0.4 ml, 4.10 mmol) were added to a solution of the amino compound (2.73 mmol) in DCM (10 ml) at room temperature. The reaction mixture was stirred for 24 h at room temperature. The reaction mixture was filtered, the filtrate was diluted with DCM (50 ml), then the organic layers were washed with water (25 ml) and brain solution (25 ml) and the combined organic layers dried over $Na_2SO_4$ and concentrated. The crude product purified by column chromatography to afford the desired product.

Synthesis of the Examples

Example 1

N-(4-(4-Fluoro-2-methoxyphenyl)pyridin-2-yl)cyclohexanecarboxamide

Preparation of the Starting Material Cyclohexanecarboxamide. Aqueous ammonia was added to solution of cyclohexanecarbonyl chloride (500 mg, 3.41 mmol) in $CHCl_3$ (10 ml). After completion of reaction, the reaction mixture was diluted with $CHCl_3$ (2×30 ml). The organic layer was washed with saturated sodium bicarbonate solution, brine and dried over anhydrous sodium sulfate. The organic layer was concentrated under vacuum, crude compound was washed with hexane (2×8 ml) and dried to afford 200 mg (46.1%) of cyclohexanecarboxamide.

Preparation of Example 1. Example 1 was synthesized according to Method B starting from the above described cyclohexanecarboxamide (75.0 mg, 0.53 mmol), $Cs_2CO_3$ (262 mg, 0.79 mmol), 2-chloro-4-(4-fluoro-2-methoxyphenyl)pyridine (100 mg, 0.42 mmol), xantphos (25 mg, 80 μmol) and Tetrakis(triphenylphosphine)palladium (0) (24 mg, 40 mmol) in 1,4-dioxane (5 ml) at 120-125° C. for 3 h in a sealed tube, and was purified after usual workup by column chromatography using ethyl acetate (5%) in petroleum ether to afford the product in a yield of 51.7%, followed by conversation to the HCl-salt by dissolving the above obtained compound (65.0 mg, 0.17 mmol) in DCM (5 ml) and addition of 1.2 eq. of ethereal HCl (0.20 ml, 0.20 mmol) at 0° C. for 30 min. The reaction mixture was triturated with diethyl ether and DCM to obtain 33 mg of the HCl-salt (50%). $^1$H-NMR (free base, 400 MHz, DMSO-$d_6$): δ=10.38 (s, 1H), 8.28 (d, 1H), 8.20 (s, 1H), 7.38 (t, 1H), 7.18 (d, 1H), 7.08 (d, 1H), 6.88 (t, 1H), 3.82 (s, 3H), 1.82-1.60 (m, 5H), 1.44-1.18 (m, 5H), $^1$H-NMR (HCl-salt, 400 MHz, DMSO-$d_6$): δ=11.08 (s, br., 1H), 8.32 (d, 1H), 8.09 (s, 1H), 7.45 (t, 1H), 7.36 (d, 1H), 7.12 (dd, 1H), 6.94 (dt, 1H), 3.84 (s, 3H), 1.86-1.82 (d, 2H), 1.76-1.73 (d, 2H), 1.66-1.63 (d, 1H), 1.42-1.36 (m, 2H), 1.28-1.20 (m, 3H), HPLC (λ=214 nm, [A]): rt 15.3 min (100%), mp: decomposes at 92° C., melts compl. at 129° C.

Example 2

2-Cyclohexyl-N-(4-(4-fluoro-2-methoxyphenyl)pyridin-2-yl)acetamide

Preparation of the Starting Material 2-Cyclohexylacetamide. Aqueous ammonia was added to solution of 2-cyclohexylacetyl chloride (500 mg, 3.11 mmol) in $CHCl_3$ (10 ml). After completion of reaction, the reaction mixture was diluted with $CHCl_3$ (2×30 ml). The organic layer was washed with saturated sodium bicarbonate solution, brine and dried over anhydrous sodium sulfate. The organic layer was concentrated under vacuum, crude compound was washed with hexane (2×8 ml) and dried to afford 400 mg (87.8%) of 2-cyclohexylacetamide.

Preparation of Example 2. Example 2 was synthesized according to Method B starting from the above described 2-cyclohexylacetamide (75.0 mg, 0.59 mmol), $Cs_2CO_3$ (262 mg, 0.79 mmol), 2-chloro-4-(4-fluoro-2-methoxyphenyl)pyridine (111 mg, 0.47 mmol), xantphos (27 mg, 47 μmol) and Tetrakis(triphenylphosphine)palladium (0) (27 mg, 23 μmol) in 1,4-dioxane (5 ml), and was purified after usual workup by column chromatography using ethyl acetate (5%) in petroleum ether to afford the product in a yield of 49.5%, followed by conversation to the HCl-salt by dissolving the above obtained compound (65.0 mg, 0.16 mmol) in DCM (5 ml) and addition of 1.2 eq. of ethereal HCl (0.19 ml, 0.19 mmol) at 0° C. for 30 min. The reaction mixture was triturated with diethyl ether, DCM and dried in vacuo to give 30 mg of the HCl-salt (46.1%). $^1$H-NMR (free base, 400 MHz, DMSO-$d_6$): δ=10.38 (s, 1H), 8.22 (d, 1H), 8.18 (s, 1H), 7.36 (t, 1H), 7.18 (d, 1H), 7.06 (dd, 1H), 6.92 (dt, 1H), 3.82 (s, 3H), 2.24 (d, 2H), 1.82-1.62 (m, 6H), 1.38-0.92 (m, 6H), $^1$H-NMR (HCl-salt, 400 MHz, DMSO-$d_6$): δ=10.96 (s, br., 1H), 8.31 (d, 1H), 8.11 (s, 1H), 7.43 (t, 1H), 7.31 (d, 1H), 7.09 (dd, 1H), 6.94 (dt, 1H), 3.83 (s, 3H), 2.32 (d, 2H), 1.71-1.64 (m, 6H), 1.20-0.96 (m, 5H), HPLC (λ=214 nm, [A]): rt 16.9 min (100%), mp: decomposes at 109° C., melts compl. at 137° C.

Example 3

N-(4-Fluoro-2-methoxyphenyl)pyridin-2-yl)piperidine-4-carboxamide

Step A: Preparation of tert-butyl 4-Carbamoylpiperidine-1-carboxylate. To a solution of isonipecotamide (500 mg, 3.90 mmol) in a mixture of 5% aqueous sodium carbonate (7 ml) and 1,4-dioxane (3 ml) was added Boc-anhydride (1.30 ml, 5.85 mmol) and stirred for 5 h at room temperature. The pH was adjusted to 5-6 with acetic acid and volatiles were evaporated under vacuo. The residue was triturated with n-pentane and diethyl ether to yield 740 mg (82.4%) of tert-butyl 4-carbamoylpiperidine-1-carboxylate as a white solid.

Step B: The Boc-protected precursor of Example 3 tert-butyl 4-(4-(4-fluoro-2-methoxyphenyl)pyridin-2-ylcarbamoyl)piperidine-1-carboxylate was synthesized according to Method B starting from the above obtained compound tert-butyl 4-carbamoylpiperidine-1-carboxylate (100 mg, 0.44 mmol), 2-chloro-4-(4-fluoro-2-methoxy-phenyl)pyridine (94 mg, 0.4 mmol), $Cs_2CO_3$ (184 mg, 0.56 mmol), xantphos (13 mg, 23 mol) and Tetrakis(triphenylphosphine)palladium (0) (9 mg, 8 μmol) in 1,4-dioxane (10 ml) at 125° C. for 3 h, and was purified after usual workup by column chromatography using DCM, petroleum ether, MeOH to afford the product in a yield of 23.5% as colorless oil. $^1$H-NMR (400 MHz, $CDCl_3$): δ=8.34 (s, 1H), 8.25 (d, 1H), 8.00 (s, 1H), 7.70-7.65 (m, 1H), 7.48-7.42 (m, 1H), 7.35-7.32 (m, 1H), 7.22 (d, 1H), 6.76-6.70 (m, 2H), 4.17 (s, 2H), 3.83 (s, 3H), 2.82 (t, 2H), 2.45-2.40 (m, 1H), 1.93-1.90 (m, 2H), 1.79-1.70 (m, 2H), 1.46 (s, 9H), 0.88-0.86 (m, 4H), MS (m/z): 430.2 (M+H).

Preparation of Example 3 . Example 3 was synthesized according to Method C starting from the above obtained tert-butyl 4-(4-(4-fluoro-2-methoxyphenyl)pyridin-2-ylcarbamoyl)piperidine-1-carboxylat (130 mg, 0.30 mmol), TFA (0.05 ml, 0.61 mmol) in DCM at 0° C. warmed up to room temperature and was stirred for 16 h. The reaction mixture was triturated with n-pentane to give the compound as a colorless oil in a yield of 80.2%, followed by conversation to the HCl-salt by dissolving the above obtained compound (50.0 mg, 0.15 mmol) in DCM (5 ml) and addition of 2.2 eq. of ethereal HCl at 0° C. for 1 h. The reaction mixture was triturated with diethyl ether to afford 45 mg of the HCl-salt (74%) as a colorless solid. $^1$H-NMR (free base, 400 MHz, DMSO-$d_6$): δ=8.35 (s, 1H), 8.24 (d, 1H), 7.89 (s, 1H), 7.35-7.20 (m, 2H), 6.75-6.70 (m, 2H), 3.83 (s, 3H), 3.18 (d, 2H), 2.72-2.66 (m, 2H), 2.41 (t, 1H), 1.96-1.93 (m, 2H), 1.77-1.72

(m, 2H), $^1$H-NMR (HCl-salt, 400 MHz, DMSO-d$_6$): δ=8.34 (d, 1H), 7.83 (d, 1H), 7.62 (s, 1H), 7.06 (d, 1H), 6.92 (t, 1H), 3.94 (s, 3H), 3.53-3.50 (m, 2H), 3.18-3.12 (m, 2H), 2.98 (s, 1H), 2.26-2.22 (m, 2H), 2.09-2.06 (m, 2H), HPLC (λ=214 nm, [A]): rt 9.7 min (97.5%), mp: decomposes at 260° C., completely melts at 280° C.

Example 4 cis-4-Amino-N-(4-(4-fluoro-2-methoxyphenyl)pyridin-2-yl)cyclohexane-carboxamide

Step A: Preparation of cis-4-[[(1,1-Dimethylethoxy)carbonyl]amino]-cyclohexanecarboxylic acid. Boc-anhydride (2.30 ml, 4.19 mmol) was added to a solution of cis-4-amino cyclohexyl carboxylic acid (1.00 g, 6.99 mmol) in aqueous solution of sodium carbonate (6 ml, 5% w/w) in dioxane (14 ml) at 0° C. The reaction mixture was allowed to warm up to room temperature and stirred for 18 h. The reaction mixture was acidified to pH-4 using citric acid. The compound was extracted with ethyl acetate (3×30 ml) and washed with brine (15 ml). The combined organic layers were dried over anhydrous sodium sulfate and filtered. The solvent was evaporated and dried to afford 1.2 g (71.8%) of cis-4-[[(1,1-dimethylethoxy)carbonyl]amino]-cyclohexanecarboxylic acid.

Step B: Preparation of cis-tert-Butyl-4-carbamoylcyclohexylcarbamate. Pivaloyl chloride (0.36 ml, 2.96 mmol) was added to a solution of cis-4-[[(1,1-dimethylethoxy)carbonyl]amino]-cyclohexanecarboxylic acid (600 mg, 2.47 mmol) in CHCl$_3$ (10 ml), triethylamine (0.7 ml) at 0° C. and stirred for 1 h. Then aqueous ammonia was added to the reaction mixture and stirred for 1 h. After completion of reaction, the reaction mixture was diluted with CHCl$_3$ (2×25 ml). The organic layer was washed with saturated sodium bicarbonate solution, brine and dried over anhydrous sodium sulfate. The organic layer was concentrated under vacuum, the crude compound was washed with hexane (2×6 ml) and dried to afford 500 mg (91.8%) of cis-tert-butyl-4-carbamoylcyclohexylcarbamate as white color solid.

Step C: The Boc-protected precursor of Example 4 cis-tert-butyl 4-(4-(4-fluoro-2-methoxyphenyl)pyridin-2-ylcarbamoyl)cyclohexylcarbamate was synthesized according to Method B starting from the above obtained compound cis-tert-butyl-4-carbamoylcyclohexylcarbamate (400 mg, 1.65 mmol), 2-chloro-4-(4-fluoro-2-methoxyphenyl)pyridine (310 mg, 1.32 mmol), Cs$_2$CO$_3$ (810 mg, 2.47 mmol), xanthphos (76.0 mg, 0.13 mmol) and Tetrakis(triphenylphosphine) palladium (0) (76 mg, 66 μmol) in 1,4-dioxane (15 ml) at reflux for 18 h, and was purified after usual workup by column chromatography using neutral alumina and ethyl acetate (25%) in petroleum ether to afford the product cis-tert-butyl 4-(4-(4-fluoro-2-methoxyphenyl)pyridin-2-ylcarbamoyl)cyclohexylcarbamate in a yield of 27% (200 mg). $^1$H-NMR (400 MHz, CDCl$_3$): δ=10.29 (s, 1H), 8.30 (s, 1H), 8.20 (s, 1H), 7.37 (t, 1H), 7.17 (d, 1H), 7.09 (d, 1H), 6.91 (t, 1H), 6.82 (s, 1H), 3.81 (s, 3H), 3.51 (s, 1H), 1.80-1.84 (m, 2H), 1.65-1.69 (m, 2H), 1.52-1.56 (m, 4H), 1.38 (s, 9H), MS (m/z): 444.2 (M+H$^+$). Example 4 was synthesized according to Method C starting from the above obtained compound cis-tert-butyl 4-(4-(4-fluoro-2-methoxyphenyl)pyridin-2-ylcarbamoyl)cyclohexylcarbamate (100 mg, 0.23 mmol) in a mixture of TFA/DCM (1:1, 5 ml) at 0° C. for 3 h. The volatiles were evaporated and crude product was washed with diethyl ether to afford the product in a yield of 82%, followed by conversation to the HCl-salt by dissolving the above obtained compound (60.0 mg, 0.17 mmol) in DCM (5 ml) and addition of 2.2 eq. of ethereal HCl at 0° C. for 1 h. The volatiles were evaporated, the residue triturated with diethyl ether (2×3 ml), filtered and dried to afford 40 mg of the HCl-salt in a yield of 66% as an off white solid. $^1$H-NMR (free base, 400 MHz, DMSO-d): δ=10.33 (s, 1H), 8.28 (d, 1H), 8.19 (s, 1H), 7.37 (t, 1H), 7.17 (d, 1H), 7.08 (d, 1H), 6.92 (t, 1H), 3.80 (s, 3H), 3.06 (s, 1H), 1.85-1.89 (m, 2H), 1.57-1.61 (m, 6H), $^1$H-NMR (HCl-salt, 400 MHz, DMSO-d$_6$): δ=10.96 (s, 1H), 8.33 (s, 1H), 8.19 (d, 1H), 8.08-8.01 (m, 2H), 7.44-7.31 (m, 2H), 7.14-7.10 (m, 1H), 6.95-6.92 (m, 1H), 3.83 (s, 3H), 3.20 (s, 2H), 2.50 (s, 1H), 1.96 (s, 1H), 1.80-1.60 (m, 6H), HPLC (λ=214 nm, [A]): rt 8.3 min (100%), mp: decomposes at 220° C., completely melts at 240° C.

Example 5

N-(4-(4-Fluoro-2-methoxyphenyl)pyridin-2-yl)-5-oxopyrrolidine-3-carboxamide

Example 5 was synthesized according to Method A starting from the commercially available compound 5-oxopyrrolidine-3-carboxylic acid (150 mg, 1.17 mmol), 2-chloro-4-(4-fluoro-2-methoxyphenyl)pyridine (230 mg, 1.06 mmol), HATU (660 mg, 1.75 mmol) and D1PEA (1.2 ml, 2.3 mmol) in DCM (20 ml) in a sealed tube at 90° C. for 18 h, and was purified after usual workup by trituration with n-pentane/diethyl ether to afford the product in a yield of 15.5%, followed by conversation to the HCl-salt by dissolving the above obtained compound (50.0 mg, 0.15 mmol) in DCM/THF (1:1, 10 ml) and addition of 1.2 eq. of ethereal HCl (0.18 ml, 0.18 mmol, 1 M) at 0° C. for 1 h. The reaction mixture was triturated with n-pentane and diethyl ether to yield 40 mg of the HCl-salt (72.8%) as a white solid. $^1$H-NMR (free base, 400 MHz, DMSO-d$_6$): δ=10.68 (s, 1H), 8.33 (d, 1H), 8.16 (s, 1H), 7.64 (s, 1H), 7.38 (t, 1H), 7.22 (s, 1H), 7.09 (dd, 1H), 6.93 (td, 1H), 3.81 (s, 3H), 3.49 (d, 2H), 2.36-2.40 (m, 3H), $^1$H-NMR (HCl-salt, 400 MHz, DMSO-d$_6$): δ=10.90 (s, br., 1H), 8.33 (d, 1H), 8.16 (s, 1H), 7.64 (s, 1H), 7.41 (t, 1H), 7.28 (s, 1H), 7.10 (dd, 1H), 6.93 (td, 1H), 3.82 (s, 3H), 3.49 (t, 2H), 3.34 (d, 1H), 2.40 (d, 2H), HPLC (λ=214 nm, [A]): rt 9.6 min (98.9%), mp: melting range: 240-243° C.

Example 6

N-(4-(4-Fluoro-2-methoxyphenyl)pyridin-2-yl)-2-(4-methoxyphenyl)-acetamide

Preparation of the Starting Material 2-(4-Methoxyphenyl) Acetamide. A solution of 2-(4-methoxyphenyl)acetic acid (500 mg, 3.00 mmol) in DCM (30 ml) was added thionyl chloride (0.4 ml, 4.5 mmol) at 0° C. The reaction mixture was allowed to warm up to room temperature and continued to stirred overnight. Then aqueous ammonia (2 ml) was added to the reaction mixture. The white solid forming was filtered and dried under vacuum to obtained 350 mg (70%) of 2-(4-methoxyphenyl)acetamide as a white solid.

Preparation of Example 6. Example 6 was synthesized according to Method B starting from the above described 2-(4-methoxyphenyl)acetamide (100 mg, 0.62 mmol), 2-chloro-4-(4-fluoro-2-methoxyphenyl)pyridine (114 mg, 0.48 mmol), Cs$_2$CO$_3$ (299 mg, 0.90 mmol), xanthphos (28 mg, 40 μmol) and Tetrakis(triphenylphosphine)palladium (0) (28 mg, 40 μmol) in 1,4-dioxane (10 ml) in a sealed tube at 120° C. for 4 h, and was purified after usual workup by preparative TLC with MeOH (5%) in petroleum ether to afford the product in a yield of 27.1%, followed by conversation to the HCl-salt by dissolving the above obtained compound (60.0 mg, 165 mmol) in DCM (4 ml) and addition of 1.0 eq. of ethereal HCl (0.165 ml, 0.165 mmol) at 0° C. for 1 h. The reaction mixture was triturated with diethyl ether and DCM to obtain 55 mg of the HCl-salt in a yield of 91%. $^1$H-NMR (free base, 400 MHz, DMSO-ds): δ=8.35 (s, 1H), 8.20 (d, 1H), 7.87 (s, 1H), 7.32 (t, 1H), 7.24 (s, 1H), 7.17 (d, 1H), 6.92 (d, 2H), 6.75-6.69 (m, 2H), 3.82 (s, 6H), 3.70 (s, 2H), $^1$H-NMR (HCl-salt, 400 MHz, DMSO-d$_6$): δ=10.79 (s, 1H), 8.29 (d, 1H), 8.11 (s, 1H), 7.36 (t, 1H), 7.25-7.20 (m, 3H), 7.06 (dd, 1H), 6.90-6.85 (m, 3H), 3.78 (s, 3H), 3.70 (s, 3H), 3.64 (s, 2H), HPLC (λ=214 nm, [A]): rt 15 min (100%), mp: decomposes at 122° C., melts compl. at 205° C.

Example 7

N-(4-(4-Fluoro-2-methoxyphenyl)pyridin-2-yl)-2-phenylacetamide

Preparation of the Starting Material 2-Phenylacetamide.

Thionyl chloride (0.53 ml, 7.34 mmol) was added to a solution of phenyl acetic acid (0.50 g, 3.67 mmol) in CHCl$_3$ (20 ml) at 0° C. The reaction mixture was slowly heated at 70° C. for 3 h. After completion of reaction, the volatiles were evaporated and the reaction mixture was diluted with CHCl$_3$ (5 ml). Then the reaction mixture was quenched with aqueous ammonia and stirred for 10 min at room temperature. The reaction mixture was diluted with CHCl$_3$ (2×25 ml). The organic layer was separated, washed with saturated sodium bicarbonate solution, brine, dried over anhydrous sodium sulfate and filtered. The organic layer was concentrated under vacuum, the crude compound was washed with hexane (2×6 ml) and dried to afford 0.5 g (91.8%) of 2-phenylacetamide as white color solid.

Preparation of Example 7. Example 7 was synthesized according to Method B starting from the above described 2-phenylacetamide (200 mg, 1.48 mmol), 2-chloro-4-(4-fluoro-2-methoxyphenyl)pyridine (280 mg, 1.18 mmol), Cs$_2$CO$_3$ (730 mg, 2.22 mmol), xanthphos (68.0 mg, 0.11 mmol) and Tetrakis(triphenylphosphine)palladium (0) (68 mg, 50 μmol) in 1,4-dioxane (15 ml) at 125° C. for 5 h, and was purified after usual workup by column chromatography using ethyl acetate (13%) in petroleum ether to afford the product as colorless solid in a yield of 22%, followed by conversation to the HCl-salt by dissolving the above obtained compound (75.0 mg, 0.22 mmol) in DCM (5 ml) and addition of 1.2 eq. of ethereal HCl at 0° C. for 1 h. The reaction mixture was evaporated in vacuo, triturated with diethyl ether and dried in vacuo to give 60 mg of the HCl-salt (73%) as a white solid. $^1$H-NMR (free base, 400 MHz, DMSO-d$_6$): δ=10.71 (s, 1H), 8.32 (d, 1H), 8.17 (s, 1H), 7.37-7.29 (m, 5H), 7.26-7.22 (m, 1H), 7.19 (dd, 1H), 7.02 (dd, 1H), 6.89 (dt, 1H), 3.78 (s, 3H), 3.72 (s, 2H), $^1$H-NMR (HCl-salt, 400 MHz, DMSO-d$_6$): δ=11.17 (s, 1H), 8.33 (d, 1H), 8.12 (s, 1H), 7.42-7.22 (m, 7H), 7.10 (dd, 1H), 6.91 (dt, 1H), 3.81 (s, 3H), 3.77 (s, 2H), HPLC (λ=214 nm, [A]): rt 15 min (100%), mp: 193-197° C.

Example 8

N-(4-(4-Fluoro-2-methoxyphenyl)pyridin-2-yl)-2-(pyridin-4-yl)acetamide

Example 8 was synthesized according to Method B starting from the commercially available compound 2-(pyridin-4-yl)acetamide (100 mg, 0.73 mmol), Cs$_2$CO$_3$ (344 mg, 1.05 mmol), 2-chloro-4-(4-fluoro-2-methoxyphenyl)pyridine (156 mg, 0.66 mmol), xanthphos (38 mg, 90 μmol) and Tetrakis(triphenylphosphine)palladium (0) (33 mg, 40 μmol) in 1,4-dioxane (5 ml) at 120-125° C. for 3 h in a sealed tube, and was purified after usual workup by column chromatography using MeOH (5%) in CHCl$_3$ to afford the product in a yield of 44.4%, followed by conversation to the HCl-salt by dissolving the above obtained compound (50.0 mg, 0.15 mmol) in DCM (5 ml) and addition of 2.2 eq. of ethereal HCl at 0° C. for 30 min. The reaction mixture was triturated with diethyl ether and DCM to obtain 48 mg of the HCl-salt (78.2%) as a light orange solid. $^1$H-NMR (free base, 400 MHz, DMSO-d$_6$): δ=10.86 (s, 1H), 8.51 (d, 1H), 8.33 (d, 1H), 8.16 (s, 1H), 7.38-7.32 (m, 3H), 7.22 (dd, 1H), 7.07 (dd, 1H), 6.89 (dt, 1H), 3.80 (s, 2H), 3.79 (s, 3H), $^1$H-NMR (HCl-salt, 400 MHz, DMSO-d$_6$): δ=11.36 (s, br., 1H), 8.85 (s, 2H), 8.35 (d, 1H), 8.14 (s, 1H), 8.05 (s, 1H), 7.39-7.30 (m, 2H), 7.08 (d, 1H), 6.95-6.93 (m, 1H), 4.23 (s, 2H), 3.80 (s, 3H), HPLC (λ=214 nm, [A]): rt 9.2 min (98.9%), mp: decomposes at 170° C., completely melts at 190° C.

Example 9

N-(4-(4-Fluoro-2-methoxyphenyl)pyridin-2-yl)-2-(thiophen-2-yl)acetamide

Example 9 was synthesized according to Method B starting from the commercially available compound 2-(thiophen-2-yl)acetamide (100 mg, 0.71 mmol), 4-chloro-6-(4-fluoro-2-methoxyphenyl)pyridine (152 mg, 0.64 mmol), Cs$_2$CO$_3$ (297 mg, 0.90 mmol), xanthphos (22 mg, 40 μmol) and Tetrakis(triphenylphosphine)palladium (0) (15 mg, 10 μmol) in 1,4-dioxane (10 ml) at 125° C. for 4 h, and was purified after usual workup by column chromatography using neutral alumina, MeOH in DCM to afford the product in a yield of 20.5%, followed by conversation to the HCl-salt by dissolving the above obtained compound (50.0 mg, 0.15 mmol) in DCM (2 ml) and addition of 1.2 eq. of ethereal HCl at 0° C. for 1 h. The reaction mixture was triturated with diethyl ether to obtain the HCl-salt in a yield of 59% as an off white solid. $^1$H-NMR (free base, 400 MHz, CDCl$_3$): δ=8.35 (s, 1H), 8.21 (d, 1H), 8.04 (s, 1H), 7.34-7.28 (m, 2H), 7.20 (d, 1H), 7.04-7.02 (m, 2H), 6.76-6.70 (m, 2H), 3.97 (s, 2H), 3.83 (s, 3H), $^1$H-NMR (HCl-salt, 400 MHz, CD$_3$OD): δ=8.32 (d, 1H), 7.79-7.74 (m, 2H), 7.62 (t, 1H), 7.36 (d, 1H), 7.07-7.02 (m, 2H), 7.00 (t, 1H), 6.94-6.90 (m, 1H), 4.13 (s, 2H), 3.94 (s, 3H), HPLC (λ=214 nm, [A]): rt 15.3 min (97%), mp: 216-221° C.

Example 10

(2S)—N-(4-(5-Fluoro-2-methoxyphenyl)pyridin-2-yl)-2-phenylpropanamide

Example 10 was synthesized according to Method B starting from the commercially available compound (S)-2-phenylpropanamide (100 mg, 0.67 mmol), 2-chloro-4-(4-fluoro-2-methoxyphenyl)pyridine (145 mg, 0.61 mmol), Cs$_2$CO$_3$ (281 mg, 0.85 mmol), xanthphos (21 mg, 40 μmol) and Tetrakis(triphenylphosphine)palladium (0) (14 mg, 10 μmol) in 1,4-dioxane (10 ml) at 125° C. for 5 h, and was purified after usual workup by column chromatography using neutral alumina, MeOH in DCM to afford the product in a yield of 17.9%, followed by conversation to the HCl-salt by dissolving the above obtained compound (80.0 mg, 0.23 mmol) in DCM (4 ml) and addition of 1.2 eq. of ethereal HCl (0.22 ml, 0.27 mmol) at 0° C. for 1 h. The reaction mixture was triturated with diethyl ether to obtain the HCl-salt in a yield of 62.5% as an off white solid. $^1$H-NMR (free base, 400 MHz, CDCl$_3$): δ=8.38 (s, 1H), 8.19 (d, 1H), 7.78 (s, 1H), 7.39-7.25 (m, 5H), 7.19-7.18 (m, 1H), 7.12-7.02 (m, 2H), 6.93-6.89 (m, 1H), 3.80 (s, 3H), 3.75 (q, 1H), 1.60 (d, 3H), $^1$H NMR (HCl-salt, 400 MHz, CD$_3$OD): δ=8.33 (d, 1H), 7.76-7.73 (m, 2H), 7.43-7.20 (m, 7H), 4.00 (q, 1H), 3.88 (s, 3H), 1.57 (d, 3H), HPLC (λ=214 nm, [A]): rt 17.2 min (98.2%), mp: decomposes at 80° C., completely melts at 160° C.

Example 11

(2S)—N-(4-(4-Fluoro-2-methoxyphenyl)pyridin-2-yl)-2-(4-methoxyphenyl)-propanamide Step A: Preparation of (S)-4-Benzyl-3-(2-(4-methoxyphenyl)acetyl)oxazolidin-2-one. n-Butyllithium (15.4 ml, 24.7 mmol, 1.6 M) was added to a solution of (S)-4-benzyl oxazolidinone (4.00 g, 22.5 mmol) in dry THF (100 ml) at −78° C. and stirred for 30 min. Then p-methoxyphenyl acetyl chloride (6.50 ml, 29.3 mmol) in THF (50 ml) was added to the reaction mixture at −78° C. The reaction mixture was allowed to warm up to room temperature and stirred overnight. It was then quenched with saturated ammonium chloride solution (50 ml) and extracted with ethyl acetate (3×50 ml). The crude compound was purified by column chromatography over silica gel (60-120 mesh) using ethyl acetate (7%) in petroleum ether as eluent to afford 6.0 g (82.5%) of (S)-4-benzyl-3-(2-(4-methoxyphenyl)acetyl)oxazolidin-2-one as an off-white color solid.

Step B: Preparation of (S)-3-((R)-2-(4-Methoxyphenyl)propanoyl)-4-benzyloxazolidin-2-one. A solution of (S)-4-benzyl-3-(2-(4-methoxyphenyl)acetyl)oxazolidin-2-one (1.00 g, 3.07 mmol) in dry THF (10 ml) was added to lithium diisopropyl amide (400 mg, 3.69 mmol, 0.1 M) at −78° C. The reaction mixture was stirred for 2 h. Iodomethane (2.00 g, 14.1 mmol) was added to the reaction mixture and warmed to −20° C. and stirred for another 2 h. The reaction mixture was quenched with saturated ammonium chloride solution (20 ml) and extracted with ethyl acetate (3×25 ml). The combined organic layers was dried over anhydrous sodium sulfate, filtered and concentrated. The crude compound was purified by column chromatography over silica gel (60-120 mesh) using ethyl acetate (10%) in petroleum ether as eluent to afford 350 mg (33.8%) of (S)-3-((R)-2-(4-methoxyphenyl)propanoyl)-4-benzyloxazolidin-2-one as light yellow solid.

Step C: Preparation of (R)-2-(4-Methoxyphenyl)propanoic acid. A solution of (S)-3-((R)-2-(4-methoxyphenyl)propanoyl)-4-benzyloxazolidin-2-one (1.50 g, 4.42 mmol) in THF (20 ml) was added to a mixture of lithium hydroxide (750 mg, 17.6 mmol) and hydrogen peroxide (0.9 ml, 26.5 mmol, 30% in water). The reaction mixture was stirred at room temperature for 3 h. Then the solvent was evaporated, the residue was acidified with diluted HCl (10 ml) and extracted with DCM (3×50 ml). The combined organic layers was dried over anhydrous sodium sulfate, filtered and concentrated under reduced pressure. The crude compound was purified by column chromatography over silica gel (60-120 mesh) using ethyl acetate (20%) in petroleum ether as eluent to afford 600 mg (76%) of (R)-2-(4-methoxyphenyl)propanoic acid as colorless liquid.

Step D: Preparation of (R)-2-(4-Methoxyphenyl)propanamide. To a solution of (R)-2-(4-methoxyphenyl)propanoic acid (400 mg, 2.22 mmol) in DCM (10 ml) was added thionyl chloride (0.42 ml, 5.55 mmol) at room temperature and stirred overnight. The volatiles were evaporated and the residue was added to aqueous ammonia (5 ml) slowly. A white solid precipitated was filtered and dried to afford 250 mg (62.5%) of (R)-2-(4-methoxyphenyl)propanamide as a white solid.

Preparation of Example 11. Example 11 was synthesized according to Method B starting from the above described (R)-2-(4-methoxyphenyl)propanamide (150 mg, 0.83 mmol), 2-chloro-4-(4-fluoro-2-methoxyphenyl)pyridine (158 mg, 0.68 mmol), Cs$_2$CO$_3$ (409 mg, 1.24 mmol), xanthphos (35 mg, 60 μmol) and Tetrakis(triphenylphosphine)palladium (0) (38 mg, 30 μmol) in DCM (10 ml) in a sealed tube for 4 h at 125° C., and was purified after usual workup by column chromatography using MeOH (3%) in CHCl$_3$ to afford the product in a yield of 38%, followed by conversation to the HCl-salt by dissolving the above obtained compound (60.0 mg, 0.15 mmol) in DCM (2 ml) and addition of 1.0 eq. of ethereal HCl at 0° C. for 1 h. The reaction mixture was triturated with diethyl ether and 58 mg of the HCl-salt were obtained (88%) as an off white solid. $^1$H-NMR (free base, 400 MHz, DMSO-d$_6$): δ=10.62 (s, 1H), 8.25 (d, 1H), 8.18 (s, 1H), 7.38-7.30 (m, 3H), 7.19 (d, 1H), 7.08 (dd, 1H), 6.92 (d, 3H), 4.03 (q, 1H), 3.82 (s, 3H), 3.70 (s, 3H), 1.53 (d, 3H), $^1$H-NMR (HCl-salt, 400 MHz, DMSO-d$_6$): δ=11.06 (s, 1H), 8.34 (d, 1H), 8.10 (s, 1H), 7.38 (t, 1H), 7.32-7.24 (m, 3H), 7.08 (d, 1H), 6.92 (d, 3H), 4.03 (q, 1H), 3.82 (s, 3H), 3.70 (s, 3H), 1.53 (d, 3H), HPLC (λ=214 nm, [A]): rt 16.3 min (100%), mp: 210° C.

Example 12 and 13

Isomers of N-(4-(4-Fluoro-2-methoxyphenyl)pyridin-2-yl)-2-(pyridin-3-yl)propanamide Preparation of the Starting Material 2-(Pyridin-3-yl)propanamide. Thionyl chloride (0.64 ml, 8.86 mmol) was added to a solution of 2-(pyridin-3-yl)propanoic acid (0.67 g, 4.43 mmol) in CHCl$_3$ (30 ml) at 0° C. The reaction mixture was slowly heated at 70° C. for 3 h. After completion of reaction, the volatiles were evaporated and the reaction mixture was diluted with CHCl$_3$ (5 ml). Then the reaction mixture was quenched with aqueous ammonia and stirred for 10 min at room temperature. The reaction mixture was diluted with CHCl$_3$ (2×35 ml). The organic layer was separated, washed with saturated sodium bicarbonate solution, brine, dried over anhydrous sodium sulfate and filtered. The organic layer was concentrated under vacuum, the crude compound was washed with hexane (2×50 ml) and dried to afford 0.43 g (65%) of 2-(pyridin-3-yl)propanamide as white color solid.

Preparation of Example 12 and 13. Example 12 and 13 were synthesized according to Method B starting from the above described 2-(pyridin-3-yl)propanamide (100 mg, 0.66 mmol), Cs$_2$CO$_3$ (311 mg, 0.95 mmol), 2-chloro-4-(4-fluoro-2-methoxyphenyl)pyridine (140 mg, 0.59 mmol), xantphos (38 mg, 90 mol) and Tetrakis(triphenylphosphine)palladium (0) (33 mg, 40 μmol) in 1,4-dioxane (5 ml) at 120-125° C. for 3 h in a sealed tube, and was purified after usual workup by column chromatography with MeOH (2-3%) in CHCl$_3$ followed by preparative chiral HPLC (CHIRALPAC 1C (250× 4.6 mm, 5), Mobile phase: Hexane/EtOH/DEA:70/30/0.1) in a yield of 25.6% (Exam. 12) and 27.7% (Exam. 13), followed by conversation to the HCl-salt by dissolving (Exam. 12: 60.0 mg, 0.16 mmol, Exam. 13: 65.0 mg, 0.17 mmol) in DCM (5 ml each) and addition of 2.2 eq. of ethereal HCl at 0° C. for 30 min. The reaction mixtures were triturated with diethyl ether and DCM to obtain 60 mg each the HCl-salt in a yield of 76.2% as a violet solid (Exam. 12) and 74.2% as an off white solid (Exam. 13). $^1$H-NMR (free base, both isomers, 400 MHz, DMSO-d$_6$): δ=10.78 (s, 1H), 8.59 (s, 1H), 8.42 (d, 1H), 8.26 (d, 1H), 8.16 (s, 1H), 7.78 (d, 1H), 7.36-7.30 (m, 2H), 7.18 (d, 1H), 7.04 (d, 1H), 6.88 (t, 1H), 4.04 (q, 1H), 3.78 (s, 3H), 1.46 (d, 3H), $^1$H-NMR (HCl-salt, both isomers, 400 MHz, DMSO-d$_6$): δ=11.00 (s, 1H), 8.92 (d, 1H), 8.82 (s, 1H), 8.56 (s, br., 1H), 8.32 (d, 1H), 8.14 (s, 1H), 8.04-7.98 (m, 1H), 7.40-7.22 (m, 2H), 7.08 (d, 1H), 6.92 (t, 1H), 4.36 (q, 1H), 3.82 (s, 3H), 1.58 (d, 3H), HPLC (λ=214 nm, [A]): rt 9.8 min (99.1%), Exam. 12: chiral purity: 99.58%, Exam. 13: mp: decomposes at 50° C., melts compl. at 170° C., chiral purity: 99.19%.

Example 14

N-(4-(4-Fluoro-2-methoxyphenyl)pyridin-3-yl)acetamide

Step A: Preparation of (6-Methoxypyridin-3-yl)methanol. Lithium aluminum hydride (0.40 g, 10.8 mmol) was added to a solution of methyl 6-methoxy nicotinate (1.50 g, 8.97 mmol) in THF (30 ml) at −10° C. in portions. The reaction mixture was slowly allowed to warm up to room temperature and stirred for 1 h. After completion of reaction, the reaction mixture was quenched with saturated sodium sulfate (10 ml) and filtered. The filtrate was concentrated and diluted with $CHCl_3$ (2×25 ml). The organic layer was washed with saturated sodium bicarbonate solution, brine and dried over anhydrous sodium sulfate. The organic layer was filtered and concentrated under vacuum to afford 1.1 g of a colorless liquid of (6-methoxypyridin-3-yl)methanol.

Step B: Preparation of 5-(Chloromethyl)-2-methoxypyridine. Thionyl chloride (0.23 ml, 3.23 mmol) was added to a solution of (6-methoxypyridin-3-yl)methanol (1.10 g, 8.41 mmol) in DCM at 0° C. and the reaction mixture was stirred for 2 h at room temperature. After completion of reaction, the volatiles were evaporated and the reaction mixture was basified with saturated sodium bicarbonate solution. The compound was extracted with DCM (2×30 ml) and washed with brine (15 ml). The organic layer was dried over anhydrous sodium sulfate, filtered, concentrated and dried to afford 1.1 g (88%) of 5-(chloromethyl)-2-methoxypyridine as a colorless liquid. This compound was directly taken to the next step.

Step C: Preparation of 2-(6-Methoxypyridin-3-yl)acetonitrile. Sodium cyanide (1.25 g, 25.4 mmol) was added to a solution of 5-(chloromethyl)-2-methoxypyridine (1.00 g, 6.34 mmol) in DMSO (10 ml) and stirred for 18 h at room temperature. After completion of reaction, the reaction mixture was diluted with brine and the compound was extracted with DCM (3×35 ml). The combined organic layers were dried over anhydrous sodium sulfate, filtered and evaporated. The crude compound was purified by column chromatography using 100-200 silica gel, 10% ethyl acetate in petroleum ether as eluent to afford 0.6 g (63.8%) of 2-(6-methoxypyridin-3-yl)acetonitrile as white color solid.

Step D: Preparation of 2-(6-Methoxypyridin-3-yl)acetamide. The compound 2-(6-methoxypyridin-3-yl)acetonitrile (0.60 g, 4.05 mmol) in poly phosphoric acid (6 g) was stirred at 95° C. for 1 h. The reaction mixture was neutralized with saturated sodium bicarbonate solution and the compound was extracted with DCM (3×20 ml). The combined organic layers were washed with brine (15 ml), dried over anhydrous sodium sulfate, filtered and concentrated under vacuo. The crude compound was washed with ether (2×5 ml) to afford 350 mg (52.2%) of 2-(6-methoxypyridin-3-yl)acetamide as white color solid.

Preparation of Example 14. Example 14 was synthesized according to Method B starting from the above described 2-(6-methoxypyridin-3-yl)acetamide (250 mg, 1.50 mmol), 2-chloro-4-(4-fluoro-2-methoxyphenyl)pyridine (280 mg, 1.20 mmol), $Cs_2CO_3$ (740 mg, 2.25 mmol), xanthphos (69.0 mg, 0.12 mmol) and Tetrakis(triphenylphosphine)palladium (0) (69 mg, 60 mmol) in 1,4-dioxane (15 ml) at 125° C. for 3 h, and was purified after usual workup by column chromatography using neutral alumina, MeOH (5%) in $CHCl_3$ in a yield of 20%, followed by conversation to the HCl-salt by dissolving the above obtained compound (50.0 mg, 0.13 mmol) in DCM (5 ml) and addition of 2.2 eq. of ethereal HCl. The volatiles were evaporated, the residue triturated with ether (2×3 ml), filtered and dried to afford 45 mg of the HCl-salt (83%) as colorless solid. $^1$H-NMR (free base, 400 MHz, DMSO-d$_6$): δ=10.78 (s, 1H), 8.35 (d, 1H), 8.19 (s, 1H), 8.11 (s, 1H), 7.72 (d, 1H), 7.38 (t, 1H), 7.21 (d, 1H), 7.07 (d, 1H), 6.91 (t, 1H), 6.79 (d, 1H), 3.84 (s, 3H), 3.81 (s, 3H), 3.68 (s, 2H), $^1$H-NMR (HCl-salt, 400 MHz, DMSO-d$_6$): δ=8.32 (d, 1H), 8.11 (s, 2H), 7.71-7.69 (m, 1H), 7.43-7.39 (m, 3H), 7.11-7.08 (m, 1H), 6.94-6.91 (m, 1H), 6.82-6.80 (m, 1H), 3.83 (s, 3H), 3.81 (s, 3H), 3.76 (s, 2H), HPLC (λ=214 nm, [A]): rt 14.1 min (92.8%), mp: melting range: 174-178° C.

Example 15 and 16

Isomers of N-(4-(4-Fluoro-2-methoxyphenyl)pyridin-2-yl)-2-(pyridin-4-yl)propanamide Step A: Preparation of Ethyl 2-(pyridin-4-yl)acetate. Thionyl chloride (1.70 ml, 23.0 mmol) was added to a solution of pyridin-4-yl-acetic acid hydrochloride (2.00 g, 11.5 mmol) in EtOH (30 ml) at 0° C. The reaction mixture was heated to reflux for 18 h, then the temperature of the reaction mixture was brought down to room temperature and the volatiles were evaporated in vacuo. The crude reaction mixture was basified with aqueous sodium bicarbonate solution, extracted with ethyl acetate (2×50 ml), washed with water, brine and dried over anhydrous sodium sulfate. After filtration the organic solvent was evaporated and dried to afford 1.50 g (86.2%) of ethyl 2-(pyridin-4-yl)acetate as pale yellow liquid. This was taken as such for the next step.

Step B: Preparation of Ethyl 2-(pyridin-4-yl)propanoate. A solution of ethyl 2-(pyridin-4-yl)acetate (1.00 g, 6.06 mmol) in THF (10 ml) was added dropwise to a suspension of sodium hydride (0.24 g, 6.06 mmol, 60%) in THF (10 ml) at −50° C. under an atmosphere of nitrogen. The reaction mixture was stirred for 1 h. Methyl iodide (2.10 ml, 33.6 mmol) in THF (10 ml) was added slowly at −50° C. over a period of 15 min, then the reaction mixture was warmed up to −10° C. and continued to stir for another 4 h. The reaction mixture was quenched with aqueous ammonium chloride and extracted with ethyl acetate (2×50 ml). The combined organic extracts were washed with brine (50 ml), dried over anhydrous sodium sulfate, filtered and concentrated under vacuo. The crude was washed with diethyl ether (10 ml) to get 550 mg (50.7%) of ethyl 2-(pyridin-4-yl)propanoate as a colorless liquid.

Step C: Preparation of 2-(Pyridin-4-yl)propanamide. Methanolic ammonia (20 ml) was added to ethyl 2-(pyridin-4-yl)propanoate (140 mg, 0.78 mmol) in a steel bomb. The reaction mixture was heated to 70° C. for 18 h, then the temperature of the reaction was brought down to room temperature and the volatiles were evaporated. The reaction mixture was washed with n-pentane to afford 45 mg (38.8%) of 2-(pyridin-4-yl)propanamide as an orange color solid.

Preparation of Example 15 and 16. Example 15 and 16 were synthesized according to Method B starting from the above described 2-(pyridin-4-yl)propanamide (0.36 g, 2.40 mmol), 2-chloro-4-(4-fluoro-2-methoxyphenyl)pyridine (0.56 g, 2.40 mmol), $Cs_2CO_3$ (1.10 g, 3.45 mmol), xanthphos (0.12 g, 0.22 mmol) and Tetrakis(triphenylphosphine)palladium (0) (0.110 g, 0.096 mmol) in 1,4-dioxane (20 ml) at 120° C. for 4 h, and was purified after usual workup by column chromatography by using neutral alumina, MeOH (1-2%) in DCM, yield: 0.46 g (55.5%) as pale yellow color solid, then preparative chiral HPLC (CHIRALPAC 1C (250×4.6 mm, 5μ), Mobile phase: Hexane/EtOH/DEA:70/30/0.1) in a yield of 5.9% (Exam. 15) and 7.9% (Exam. 16). $^1$H-NMR (free base, 400 MHz, DMSO-$d_6$): δ=10.81 (s, 1H), 8.50 (d, 2H), 8.29 (d, 1H), 8.17 (s, 1H), 7.39-7.33 (m, 3H), 7.19 (dd, 1H), 7.07 (dd, 1H), 6.90 (t, 1H), 4.06 (q, 1H), 3.79 (s, 3H), 1.42 (d, 3H), HPLC (λ=214 nm, [A]): rt 9.8 min (100% (Exam. 13), 99.3% (Exam. 16)), mp: melting range: 49-51° C., chiral purity: 96.68%, [α]D=+171° (Exam. 15), melting range: 96-102° C., chiral purity: 97.26%, [α]D=−151° (Exam. 16).

Example 17 and 18

Isomers of N-(4-(5-Fluoro-2-methoxyphenyl)pyridin-2-yl)-2-(thiophen-2-yl)propanamide Step A: Preparation of Methyl 2-(thiophen-2-yl)acetate. Thionyl chloride (10.20 ml, 140.7 mmol) was added to a solution of thiophen-2-yl-acetic acid (10.0 g, 70.3 mmol) in MeOH (100 ml) at 0° C. The reaction mixture was heated to reflux for 18 h, the volatiles were evaporated and the crude reaction mixture was basified with aqueous sodium bicarbonate solution, extracted with DCM, washed with brine and dried over anhydrous sodium sulfate. After filtration the organic solvent was evaporated and dried to afford 10.75 g (98%) of methyl 2-(thiophen-2-yl)acetate as color less liquid.

Step B: Preparation of Methyl 2-(thiophen-2-yl)propanoate. A solution of methyl 2-(thiophen-2-yl)acetate (4.90 g, 31.4 mmol) in THF (25 ml) was added dropwise to a suspension of sodium hydride (1.20 g, 31.4 mmol, 60%) in THF (25 ml) at −50° C. under an atmosphere of nitrogen. After the reaction mixture was stirred for 1 h, methyl iodide was added (1.76 ml, 28.2 mmol) as solution in THF (25 ml) slowly at −50° C. over a period of 15 min. The reaction mixture was warmed up to −30° C. and continued to stir for another 2 h. It was quenched with aqueous ammonium chloride, extracted with DCM (2×30 ml) and washed with brine (30 ml). The organic layer was dried over anhydrous sodium sulfate, filtered and concentrated under vacuo. The crude was purified by column chromatography over silica gel (100-200 mesh) using ethyl acetate (5%) in petroleum ether as eluent to get 2.2 g (41.7%) of methyl 2-(thiophen-2-yl)propanoate as a colorless liquid.

Step C: Preparation of 2-(Thiophen-2-yl)propanamide. Methanolic ammonia (10 ml) was added to methyl 2-(thiophen-2-yl)propanoate (200 mg, 1.17 mmol) in sealed tube, the reaction mixture was heated to 70° C. for 18 h. The volatiles were evaporated and the residue was washed with n-pentane to afford 130 mg (71.3%) of 2-(thiophen-2-yl) propanamide as brown color solid.

Preparation of Example 17 and 18

Example 17 and 18 were synthesized according to Method B starting from the above described 2-(thiophen-2-yl)propanamide (400 mg, 2.58 mmol), 2-chloro-4-(5-fluoro-2-methoxyphenyl)pyridine (0.61 g, 2.58 mmol), Cs$_2$CO$_3$ (1.20 g, 3.71 mmol), xanthphos (0.13 g, 0.23 mmol) and Tetrakis (triphenylphosphine)palladium (0) (0.14 g, 0.13 mmol) in 1,4-dioxane (20 ml) at reflux for 6 h, and was purified after usual workup by column chromatography by using neutral alumina, DCM, yield: 0.3 g (32.6%) as pale yellow color solid, then preparative chiral HPLC (CHIRALPAC 1C (250× 30 mm, 5μ), Hexane/IPA/DEA:85/15/0.1) a yield of 10.5% (Exam. 17) and 5.6% (Exam. 18), followed by conversation to the HCl-salt by dissolving the above obtained compound (30.0 mg each, 0.08 mmol) in DCM (2 ml) and addition of 1.2 eq. of ethereal HCl (0.1 ml, 0.1 mmol, 1 M) at 0° C. for 1 h. The reaction mixture was triturated with n-pentane and diethyl ether to obtain the HCl-salt in a yield of 60.5% as a pale brown solid (Exam. 17) and 62% as a light yellow solid (Exam. 18). $^1$H-NMR (free base, 400 MHz, DMSO-$d_6$): δ=10.82 (s, 1H), 8.34 (d, 1H), 8.20 (s, 1H), 7.39 (d, 1H), 7.29-7.15 (m, 4H), 7.04 (d, 1H), 6.96 (t, 1H), 4.36 (q, 1H), 3.76 (s, 3H), 1.45 (d, 3H), $^1$H-NMR (HCl-salt, 400 MHz, DMSO-$d_6$): δ=11.02 (s, 1H), 8.35 (d, 1H), 8.18 (s, 1H), 7.39 (d, 1H), 7.31-7.17 (m, 4H), 7.06 (s, 1H), 6.97 (t, 1H), 4.38 (q, 1H), 3.78 (s, 3H), 1.48 (d, 3H), HPLC (?=214 nm, [A]): rt 17.5 min (100%, both isomers), mp: melting range: 77-80° C., chiral purity: 98%, [α]$_D$=+14.83° (Exam. 17), 116° C., compound decomposes at 60° C. and completely melts at 116° C., chiral purity: 97.5%, [α]$_D$=−17.58° (Exam. 18).

Example 19

2-(2-Chloropyridin-4-yl)-N-(4-(4-fluoro-2-methoxyphenyl)pyridin-2-yl)acetamide

Example 19 was synthesized according to Method A starting from the commercially available compound 2-(2-chloropyridin-4-yl)acetic acid (150 mg, 0.88 mmol), 2-amino-4-(4-fluoro-2-methoxyphenyl)pyridine (153 mg, 0.70 mmol), DIPEA (0.23 ml, 1.32 mmol) and HATU (500 mg, 1.32 mmol) in DCM (10 ml) in a sealed tube at 90° C. for 16 h, and was purified after usual workup by preparative TLC with ethyl acetate (5%) in petroleum ether to afford the product in a yield of 46%, followed by conversation to the HCl-salt by dissolving the above obtained compound (40.0 mg, 102 μmol) in DCM (2 ml) and addition of 1.0 eq. of ethereal HCl (0.102 ml, 0.102 mmol, 1 M) at 0° C. for 1 h. The reaction mixture was triturated with diethyl ether and DCM to obtain the HCl-salt in a yield of 88% as an off white solid. $^1$H-NMR (free base, 400 MHz, DMSO-$d_6$): δ=10.87 (s, 1H), 8.32 (d, 2H), 8.14 (s, 1H), 7.49-7.36 (m, 3H), 7.21 (d, 1H), 7.08 (d, 1H), 6.87 (d, 1H), 3.85 (s, 2H), 3.83 (s, 3H), $^1$H-NMR (HCl-salt, 400 MHz, DMSO-$d_6$): δ=11.25 (s, 1H), 8.38 (d, 2H), 8.14 (s, 1H), 7.53 (s, 1H), 7.39 (d, 3H), 7.13 (d, 1H), 6.94 (d, 1H), 3.92 (s, 2H), 3.83 (s, 3H), HPLC (λ=214 nm, [A]): rt 14.6 min (100%), mp: 203° C.

Example 20

N-(4-(4-Fluoro-2-methoxyphenyl)pyridin-2-yl)-2-(4-(4-methylpiperazin-1-yl)phenyl)acetamide Step A: Preparation of 2-(4-(4-Methylpiperazin-1-yl)phenyl)acetic acid. 1-(4-(4-Methylpiperazin-1-yl)-phenyl)-ethanone (1.00 g, 4.52 mmol), sulphur (0.35 g, 10.9 mmol), morpholine (3.03 ml, 3.00 g, 34.5 mmol) and p-toluene sulphonic acid (0.08 g, 0.46 mmol) were heated at reflux for 4 h. The reaction mixture was cooled to room temperature and quenched with ice. The solid was filtered off and dried. The crude product was taken in 10% KOH in EtOH (35 ml) and refluxed overnight. The solvent was evaporated under reduced pressure, the residue was dissolved in water (15 ml) and washed with ethyl acetate (20 ml). The pH was adjusted to 2 using 2N HCl, concentrated and dried under reduced pressure to yield 2.6 g of the crude 2-(4-(4-methylpiperazin-1-yl)phenyl)acetic acid.

Step B: Preparation of Methyl 2-(4-(4-methylpiperazin-1-yl)phenyl)acetate. Thionyl chloride (0.32 g, 2.77 mmol) was added dropwise to a suspension of 2-(4-(4-methylpiperazin-1-yl)phenyl)acetic acid (2.60 g, 11.1 mmol) in MeOH (30 ml) at 0° C. and refluxed for 5 h. The reaction mixture was concentrated and the residue was dissolved in water, made alkaline with saturated sodium bicarbonate solution up to pH-8 and extracted with DCM. The organic layer was washed with brine, dried over anhydrous sodium sulfate, filtered and evaporated to dryness to get the crude compound. The crude was purified by column chromatography over neutral alumina using 4% MeOH in DCM as eluent to afford 250 mg of methyl 2-(4-(4-methylpiperazin-1-yl)phenyl)acetate as brown color solid.

Step C: Preparation of 2-(4-(4-Methylpiperazin-1-yl)phenyl)acetamide. Methyl 2-(4-(4-methylpiperazin-1-yl)phenyl)acetate (0.45 g, 1.81 mmol) in methanolic ammonia (15 ml) was heated at 100° C. in a pressure bomb overnight. Excess MeOH was concentrated under reduced pressure to give the crude compound. This was washed with n-pentane and dried in vacuo to afford 0.24 g (57%) of 2-(4-(4-methylpiperazin-1-yl)phenyl)acetamide as a brown color solid.

Preparation of Example 20. Example 20 was synthesized according to Method B starting from the above described 2-(4-(4-methylpiperazin-1-yl)phenyl)acetamide (100 mg, 0.43 mmol), $Cs_2CO_3$ (210 mg, 0.64 mmol), 2-chloro-4-(4-fluoro-2-methoxyphenyl)pyridine (122 mg, 0.52 mmol), xantphos (20 mg, 34 μmol) and Tetrakis(triphenylphosphine)palladium (0) (20 mg, 17 μmol) in dry 1,4-dioxane (3 ml) at 120-125° C. for 3 h in a sealed tube, and was purified after usual workup by column chromatography using ethyl acetate (5%) in petroleum ether to afford the product in a yield of 43%, followed by conversation to the HCl-salt by dissolving the above obtained compound (50.0 mg, 137 mmol) in dry DCM (5 ml) and addition of 1.2 eq. of ethereal HCl (0.16 ml, 0.16 mmol) at 0° C. for 30 min. The reaction mixture was triturated with ether and dried in an oven at 70° C. for 4 h to afford the HCl-salt in a yield of 76.9% as an off white solid. $^1$H-NMR (HCl-salt, 400 MHz, DMSO-$d_6$): δ=7.43-7.36 (m, 1H), 7.32-7.28 (m, 1H), 7.28-7.24 (m, 3H), 7.10 (d, 1H), 6.99-6.94 (m, 3H), 6.94-6.88 (m, 1H), 3.83-3.75 (m, 5H), 3.67 (s, 2H), 3.49-3.44 (m, 2H), 3.18-3.04 (m, 4H), 2.80 (d, 2H), HPLC (λ=214 nm, [A]): rt 10.4 min (100%), mp: 248° C.

Example 21

N-(4-(4-Fluoro-2-methoxyphenyl)pyridin-2-yl)-3-(pyridin-4-yl)butanamide

Step A: Preparation of (Z)-Ethyl 3-(pyridin-4-yl)but-2-enoate. Triethyl phosphino acetate (1.96 ml, 9.91 mmol) was added to a suspension of sodium hydride (0.40 g, 9.91 mmol, 60%) in dry THF (15 ml) at −10° C. and stirred for 10 min. 4-Acetyl pyridine (1.00 g, 8.26 mmol) was added dropwise at −10° C. and the reaction mixture was allowed to warm up to room temperature slowly. The reaction mixture was stirred for 1 h at room temperature and quenched with acetic acid (pH~4), diluted with water and extracted with DCM (3×45 ml). The combined organic layer was washed with brine, dried over anhydrous sodium sulfate, filtered and evaporated to dryness to afford the crude compound. Purification by column chromatography over neutral alumina using 10-15% ethyl acetate in petroleum ether as eluent afforded 900 mg (57.3%) of (Z)-ethyl 3-(pyridin-4-yl)but-2-enoate as light brown liquid.

Step B: Preparation of Ethyl 3-(pyridin-4-yl)butanoate. Palladium on carbon (70 mg, 10 wt. %) was added to a solution of (Z)-ethyl 3-(pyridin-4-yl)but-2-enoate (0.70 g, 3.66 mmol) in EtOH (10 ml) and hydrogenated under balloon pressure for 18 h. The reaction mixture was filtered through a pad of celite and washed with EtOH. The filtrate was concentrated under reduced pressure to afford 0.50 g (71.4%) of ethyl 3-(pyridin-4-yl)butanoate as light brown color liquid.

Step C: Preparation of 3-(Pyridin-4-yl)butanamide. A solution of ethyl 3-(pyridin-4-yl)butanoate (0.50 g, 2.59 mmol) in methanolic ammonia (10 ml) was heated to 100° C. in a pressure bomb for 48 h. The solvent was evaporated under reduced pressure to afford the crude compound, which was washed with n-pentane and dried under reduced pressure to afford 0.2 g (47%) of 3-(pyridin-4-yl)butanamide as an off-white solid.

Preparation of Example 21. Example 21 was synthesized according to Method B starting from the above described 3-(pyridin-4-yl)butanamide (150 mg, 0.91 mmol), $Cs_2CO_3$ (450 mg, 1.37 mmol), 2-chloro-4-(4-fluoro-2-methoxyphenyl)pyridine (0.19 g, 0.82 mmol), xantphos (42 mg, 70 μmol) and Tetrakis(triphenylphosphine)palladium (0) (42 mg, 40 mol) in dry 1,4-dioxane (5 ml) at 120-125° C. for 4 h in a sealed tube, and was purified after usual workup by column chromatography using ethyl acetate (10%) in petroleum ether to afford the product in a yield of 22.6%, followed by conversation to the HCl-salt by dissolving the above obtained compound (40.0 mg, 0.10 mmol) in acetone (5 ml) and addition of 1.2 eq. of ethereal HCl (0.12 ml, 0.12 mmol, 1 M) at 0° C. for 1 h. The reaction mixture was triturated with n-pentane and dried to afford the HCl-salt in a yield of 75.8% as an off white solid. $^1$H-NMR (HCl-salt, 400 MHz, DMSO-$d_6$): δ=8.83 (d, 2H), 8.26 (d, 1H), 8.10-8.04 (m, 3H), 7.40 (t, 1H), 7.31-7.28 (m, 1H), 7.12-7.08 (m, 1H), 6.92 (td, 1H), 3.80 (s, 3H), 3.63-3.54 (m, 1H), 3.04-2.96 (m, 2H), 1.33 (d, 3H), HPLC (λ=214 nm, [A]): rt 9.5 min (97.0%), mp: 233° C.

Example 22

N-(4-(4-Fluoro-2-methoxyphenyl)pyridin-2-yl)-2-((pyridin-4-yl)methyl)-propanamide Step A: Preparation of Diethyl 2-(1-(pyridin-4-yl)propan-2-yl)malonate. To a suspension of diethyl methyl malonate (2.41 g, 13.9 mmol) in DMF (50 ml) at 0° C. was added sodium hydride (1.66 g, 41.6 mmol, 60%), followed by adding the compound 4-chloromethylpyridine hydrochloride (2.50 g, 15.2 mmol) and stirred for 16 h at room temperature. The reaction mixture was quenched by acetic acid and the product was extracted with ethyl acetate. The combined ethyl acetate layer was washed with brine, dried over anhydrous sodium sulfate, filtered and concentrated under reduced pressure to afford 2.50 g (68.1%) of diethyl 2-(1-(pyridin-4-yl)propan-2-yl)malonate as pale brown oil.

Step B: Preparation of 2-((Pyridin-4-yl)methyl)propanoic acid. Compound diethyl 2-(1-(pyridin-4-yl)propan-2-yl)malonate (2.50 g, 9.43 mmol) was refluxed in conc. HCl (30 ml) for 16 h. The pH of the reaction mixture was adjusted to 6 by adding solid sodium bicarbonate and extracted with ethyl acetate. The combined ethyl acetate layer was washed with brine, dried over anhydrous sodium sulfate, filtered and concentrated in vacuum to afford 1.20 g (76.9%) of 2-((pyridin-4-yl)methyl)propanoic acid as an off-white solid.

Step C: Preparation of 2-((Pyridin-4-yl)methyl)propanamide. Oxalyl chloride (154 mg, 1.21 mmol) was added to a stirred solution of 2-((pyridin-4-yl)methyl)propanoic acid (100 mg, 0.61 mmol) in DCM (5 ml) at 0° C. under an atmosphere of nitrogen and stirred for 1.5 h at room temperature. The reaction mixture was concentrated under reduced pressure to give the crude acid chloride. Aqueous ammonia (5 ml) was added to the above acid chloride solution at 0° C. and stirred for 30 min. The reaction mixture was extracted with ethyl acetate. The combined ethyl acetate layer was washed with water followed by brine, dried over anhydrous sodium sulfate, filtered and concentrated in vacuum to afford 92.0 mg (92.9%) of 2-((pyridin-4-yl)methyl)propanamide as a pale brown solid.

Preparation of Example 22. Example 22 was synthesized according to Method B starting from the above described 2-((pyridin-4-yl)methyl)propanamide (170 mg, 1.04 mmol), 2-chloro-4-(4-fluoro-2-methoxyphenyl)pyridine (223 mg, 942 μmol), $Cs_2CO_3$ (929 mg, 2.82 mmol), xantphos (33 mg, 57 μmol) and Tetrakis(triphenylphosphine)palladium (0) (22 mg, 19 μmol) in 1,4-dioxane (10 ml) at 120-125° C. for 16 h in a sealed tube, and was purified after usual workup by column chromatography using ethyl acetate (5%) in petroleum ether to afford the product in a yield of 22.4%, followed by conversation to the HCl-salt by dissolving the above obtained compound (50.0 mg, 137 μmol) in DCM (5 ml) and addition of 1.2 eq. of ethereal HCl (0.16 ml, 0.16 mmol, 1 M) at 0° C. for 1 h. The reaction mixture was triturated with n-pentane and dried to afford the HCl-salt in a yield of 60.4% as an off white solid. $^1$H-NMR (HCl-salt, 400 MHz, DMSO-$d_6$): δ=8.82-8.80 (m, 2H), 8.30 (d, 1H), 8.16 (s, br., 1H), 7.98-7.92 (m, 2H), 7.41-7.37 (m, 1H), 7.26-7.22 (m, 1H), 7.10 (dd, 1H), 6.95-6.89 (m, 1H), 3.80 (s, 3H), 3.04-2.95 (m, 3H), 1.14 (d, 3H), HPLC (λ=214 nm, [A]): rt 9.7 min (100%), mp: 193° C.

Example 23

N-(4-(4-Fluoro-2-methoxyphenyl)yl)pyridin-3-yl) butanamide

Step A: Preparation of (E)-Ethyl 3-(pyridin-3-yl)but-2-enoate. Diethyl 2-oxopentyl-phosphonate (1.85 g, 8.26 mol) was added dropwise to a suspension of sodium hydride (0.50 g, 12.4 mmol, 60%) in dry THF (15 ml) followed by 3-acetyl pyridine (1.00 g, 8.26 mmol) at room temperature. The reaction mixture was stirred for 2 h at room temperature, quenched with acetic acid and was adjusted to pH-6. The reaction mixture was diluted with water and extracted with $CHCl_3$. The combined organic layer was washed with brine, dried over anhydrous sodium sulfate, filtered and evaporated to dryness to yield the crude compound. Purification by column chromatography by means of neutral alumina using 10-15% ethyl acetate in petroleum ether as eluent afforded 600 mg (40%) of (E)-ethyl 3-(pyridin-3-yl)but-2-enoate as colorless liquid.

Step B: Preparation of Ethyl 3-(pyridin-3-yl)butanoate. Palladium on carbon (600 mg, 10 wt. %) was added to a solution of (E)-ethyl 3-(pyridin-3-yl)but-2-enoate (0.60 g, 3.14 mmol) in EtOH (10 ml) and hydrogenated under balloon pressure for 3 h. The reaction mixture was filtered through a pad of celite and washed with EtOH. The filtrate was concentrated and dried under reduced pressure to afford 0.60 g (100%) of ethyl 3-(pyridin-3-yl)butanoate as colorless liquid.

Step C: Preparation of 3-(pyridin-3-yl)butanamide. A solution of ethyl 3-(pyridin-3-yl)butanoate (0.50 g, 2.59 mmol) in methanolic ammonia (10 ml) was heated to 100° C. in a pressure bomb overnight. The solvent was evaporated under reduced pressure, washed with n-pentane and dried under reduced pressure to afford 0.2 g (47%) of 3-(pyridin-3-yl) butanamide as pale brown solid.

Preparation of Example 23. Example 23 was synthesized according to Method B starting from the above described 3-(pyridin-3-yl)butanamide (80.0 mg, 0.49 mmol), $Cs_2CO_3$ (242 mg, 0.74 mmol), 2-chloro-4-(4-fluoro-2-methoxyphenyl)pyridine (0.14 g, 0.58 mmol), xantphos (22 mg, 40 μmol) and Tetrakis(triphenylphosphine)palladium (0) (22 mg, 20 μmol) in 1,4-dioxane (5 ml) at 120-125° C. for 3 h in a sealed tube, and was purified after usual workup by column chromatography using ethyl acetate (5%) in petroleum ether to afford the product in a yield of 30.9%, followed by conversation to the HCl-salt by dissolving the above obtained compound (50.0 mg, 137 μmol) in DCM (5 ml) and addition of 1.2 eq. of ethereal HCl (0.16 ml, 0.16 mmol, 1 M) at 0° C. for 30 min. The reaction mixture was triturated with ether, DCM and dried in vacuum to obtain the HCl-salt in a yield of 63.5% as an off white solid. $^1$H-NMR (HCl-salt, 400 MHz, DMSO-$d_6$): δ=8.92 (s, 1H), 8.78 (s, 1H), 8.57 (s, br., 1H), 8.30 (d, 1H), 8.09-8.00 (m, 2H), 7.42-7.35 (m, 1H), 7.31-7.26 (m, 1H), 7.10 (d, 1H), 6.95-6.89 (m, 1H), 3.81 (s, 3H), 3.57-3.52 (m, 1H), 2.96-2.86 (m, 2H), 1.35 (d, 3H), HPLC (λ=214 nm, [A]): rt 9.5 min (100%), mp: 200° C.

Example 24

N-(4-(4-Fluoro-2-methoxyphenyl)pyridin-2-yl)-2-((pyridin-3-yl)methyl)-propanamide Step A: Preparation of (Pyridin-3-yl)methanol. Sodium borohydride (883 mg, 23.6 mmol) was added in three portions to a mixture of pyridine-3-carboxaldehyde (2.50 g, 23.6 mmol) in 25 ml of MeOH at 0° C. and stirred for 8 h at room temperature. The reaction mixture was quenched by ice pieces and concentrated under reduced pressure. The residue was partitioned between water and ethyl acetate. The combined ethyl acetate layer was washed with brine, dried in anhydrous sodium sulfate, filtered and concentrated in vacuo to afford 2.20 g (86.3%) of (pyridin-3-yl)methanol as pale yellow oil.

Step B: Preparation of 3-(Chloromethyl)pyridine hydrochloride. Thionyl chloride (9.60 g, 80.6 mmol) was added dropwise to a stirred solution of (pyridin-3-yl)methanol (2.20 g, 20.1 mmol) in 30 ml of $CHCl_3$ at 0° C. and refluxed for 4 h. The reaction mixture was concentrated under reduced pressure to afford 2.10 g (63.6%) of 3-(chloromethyl)pyridine hydrochloride as a brown solid.

Step C: Preparation of Diethyl 2-(1-(pyridin-3-yl)propan-2-yl)malonate. To a suspension of diethyl methyl malonate (1.80 g, 10.2 mmol) in DMF (25 ml) at 0° C. was added sodium hydride (1.25 g, 31.0 mmol, 60%), followed by 3-(chloromethyl)pyridine hydrochloride (2.00 g, 12.2 mmol) and stirred for 8 h at room temperature. The reaction mixture was quenched with acetic acid and extracted with ethyl acetate. The combined ethyl acetate layers were washed with brine, dried over anhydrous sodium sulfate, filtered and concentrated in vacuo to afford 2.50 g (91.2%) of diethyl 2-(1-(pyridin-3-yl)propan-2-yl)malonate as pale brown oil.

Step D: Preparation of 2-((Pyridin-3-yl)methyl)propanoic acid. Diethyl 2-(1-(pyridin-3-yl)propan-2-yl)malonate (2.00 g, 7.55 mmol) was refluxed in conc. HCl (30 ml) for 16 h. The reaction mixture was neutralized using solid sodium bicarbonate (pH~7) and extracted with ethyl acetate. The combined ethyl acetate layer was washed with brine, dried over anhydrous sodium sulfate, filtered and concentrated in vacuo to afford 580 mg (46.4%) of 2-((pyridin-3-yl)methyl)propanoic acid as a brown semi solid.

Step E: Preparation of 2-((Pyridin-3-yl)methyl)propanamide. Oxalyl chloride (385 mg, 3.03 mmol) was added to a stirred solution of 2-((pyridin-3-yl)methyl)propanoic acid (250 mg, 1.52 mmol) in DCM (5 ml) at 0° C. under an atmosphere of nitrogen and stirred for 1.5 h at room temperature. The reaction mixture was concentrated under reduced pressure and the obtained residue was quenched by liquid ammonia (5 ml) at 0° C. and the product was extracted with ethyl acetate. The combined ethyl acetate layer was washed with water followed by brine, dried over anhydrous sodium sulfate, filtered and concentrated in vacuo to afford 90 mg (36.3%) of 2-((pyridin-3-yl)methyl)propanamide as a brown solid.

Preparation of Example 24. Example 24 was synthesized according to Method B starting from the above described 2-((pyridin-3-yl)methyl)propanamide (350 mg, 2.13 mmol), 2-chloro-4-(4-fluoro-2-methoxyphenyl)pyridine (460 mg, 1.94 mmol), $Cs_2CO_3$ (1.90 g, 5.82 mmol), xantphos (67 mg, 45 mol) and Tetrakis(triphenylphosphine)palladium (0) (45 mg, 38 mmol) in 1,4-dioxane (15 ml) at 120-125° C. for 16 h in a sealed tube, and was purified after usual workup by column chromatography using ethyl acetate (5%) in petroleum ether to afford the product in a yield of 25.8%, followed by conversation to the HCl-salt by dissolving the above obtained compound (50.0 mg, 137 mol) in acetone (5 ml) and addition of 1.2 eq. of ethereal HCl (0.13 ml, 0.16 mmol) at 0° C. for 1 h. The reaction mixture was triturated with n-pentane to obtain the HCl-salt in a yield of 73% as an off-white solid. $^1$H-NMR (HCl-salt, 400 MHz, DMSO-$d_6$): δ=8.85 (s, 1H), 8.76 (d, 1H), 8.46 (d, 1H), 8.29 (d, 1H), 8.15 (s, 1H), 8.00-7.96 (m, 1H), 7.42-7.37 (m, 1H), 7.27 (d, 1H), 7.09 (dd, 1H), 6.95-6.88 (m, 1H), 3.81 (s, 3H), 3.18-3.08 (m, 2H), 2.94-2.88 (m, 1H), 1.14 (d, 3H), HPLC (λ=214 nm, [A]): rt 9.7 min (100%).

Example 25 and Example 26 trans-3-Acetamido-N-(4-(4-fluoro-2-methoxyphenyl)-pyridin-2-yl)cyclohexanecarboxamide Step A: Preparation of trans-Methyl 3-aminocyclohexanecarboxylate. Thionyl chloride (0.6 ml) was added to a solution of trans-3-amino-cyclohexane carboxylic acid (0.5 g, 2.8 mmol) in MeOH (20 ml) at 0° C. The reaction mixture was heated to 65° C. and concentrated in vacuum. The resulting residue was partitioned between saturated sodium bicarbonate (10 ml) and extracted with ethyl acetate. The combined organic layer was washed with brine solution, dried over anhydrous sodium sulfate, filtered and concentrated under vacuum to afford 400 mg (90.9%) of trans-methyl 3-aminocyclohexanecarboxylate as colorless liquid.

Step B: Preparation of trans-Methyl 3-acetamidocyclohexanecarboxylate. Acetic anhydride (1.20 ml, 12.7 mmol) was added to a solution of trans-methyl 3-aminocyclohexanecarboxylate (0.40 g, 2.54 mmol) in pyridine (10 ml) at 0° C. The reaction mixture was warmed to room temperature and stirred for 1 h. The volatiles were removed in vacuum, the resulting residue was dissolved in DCM and washed with saturated sodium bicarbonate solution followed by brine solution (10 ml). After drying over anhydrous sodium sulfate and filtration the filtrate was concentrated under vacuum to afford 350 mg (69.0%) of trans-methyl 3-acetamidocyclohexanecarboxylate as a colorless liquid.

Step C: Preparation of trans-3-Acetamidocyclohexanecarboxamide. Methanolic ammonia (20 ml) was added to trans-methyl 3-acetamidocyclohexanecarboxylate (350 mg, 1.75 mmol), taken in a steel bomb and heated at 70° C. for 18 h. The reaction mixture was concentrated, washed with n-pentane and dried under reduced pressure to afford 200 mg (57.1%) of trans-3-acetamidocyclohexanecarboxamide as white color solid.

Preparation of Example 25 and 26

Example 25 and 26 were synthesized according to Method B starting from the above described trans-3-acetamidocyclohexanecarboxamide (200 mg, 1.08 mmol), 2-chloro-4-(4-fluoro-2-methoxyphenyl)pyridine (260 mg, 1.08 mmol), $Cs_2CO_3$ (500 mg, 1.56 mmol), xantphos (57 mg, 97 µmol) and Tetrakis(triphenylphosphine)palladium (0) (50 mg, 40 µmol) in 1,4-dioxane (15 ml) at 125° C. for 5 h in a sealed tube to afford both compounds as a mixture in a yield of 59.8%, purified in a first step by column chromatography over neutral alumina using 2% MeOH in DCM. Further purification by preparative HPLC (CHIRALPAK IA (20×250 mm, 5µ), Hexane/EtOH/DEA:90/10/0.1, λ=281 nm, flow rate: 19 ml min$^-$$_1$) has afford Example 25 in a yield of 24% and Example 26 in a yield of 14.4%, followed by conversation to the HCl-salt by dissolving the above obtained compound (Exam. 25: 110 mg, 0.28 mmol, Exam. 26: 80.0 mg, 0.21 mmol) in acetone (5 ml) and addition of 1.2 eq. of ethereal HCl (Exam. 25: 0.34 ml, 0.34 mmol, Exam. 26: 0.25 ml, 0.25 mmol, 1 M) at 0° C. for 1 h. The reaction mixtures were dissolved in water and lyophilized to obtain the HCl-salts in a yield of 61.2% as an off white solid (Example 25, chiral purity: 96%) and 40.7% as an off white solid (Example 26, chiral purity: 97%). $^1$H-NMR for Example 25 and 26 (HCl-salt, 400 MHz, DMSO-$d_6$): δ=8.30 (d, 1H), 8.14 (s, 1H), 7.60 (d, 1H), 7.40 (dd, 1H), 7.27-7.23 (m, 1H), 7.09 (dd, 1H), 6.91 (td, 1H), 3.98-3.92 (m, 1H), 3.82 (s, 3H), 2.84-2.75 (m, 1H), 1.84 (s, 3H), 1.80-1.63 (m, 3H), 1.59-1.48 (m, 5H), HPLC (λ=214 nm, [A]): rt 11.2 min (98.75% (Exam. 25), 99.15% (Exam. 26)), optical rotation: +10.5° (Example 25) and −7.4° (Example 26) (1% solution in MeOH), mp (Example 25): starting at 70° C. and completely melts at 160° C., (Example 26): starting at 80° C. and completely melts at 160° C.

Example 27

N-(4-(4-Fluoro-2-methoxyphenyl)pyridin-2-yl)-2-(4-(4-methylpiperazin-1-yl)phenyl)propanamide Step A: Preparation of Diethyl 2-methyl-2-(4-nitrophenyl)malonate. Diethyl methyl malonate (6.17 g, 35.4 mmol) was added to a stirred solution of sodium hydride (1.63 g, 42.5 mmol, 60%) in DMSO (50 ml) and stirred for 1 h at room temperature. 1-Fluoro-4-nitrobenzene (5.00 g, 35.4 mmol) was added dropwise to the reaction mixture and stirred for 6 h at room temperature. The reaction mixture was quenched with saturated ammonium chloride solution and extracted with diethyl ether. The separated organic layer was washed with brine solution, dried over anhydrous sodium sulfate, filtered and concentrated in vacuo to afford the crude product. Purified by column chromatography over silica gel (60-120 mesh) using 20% ethyl acetate in petroleum ether as eluent afford 8.20 g (78.8%) of diethyl 2-methyl-2-(4-nitrophenyl)malonate as an oil.

Step B: Preparation of Diethyl 2-(4-aminophenyl)-2-methylmalonate. Stannous chloride dihydrate (30.60 g, 135.6 mmol) was added to a solution of diethyl 2-methyl-2-(4-nitrophenyl)malonate (8.00 g, 27.1 mmol) in EtOH (100 ml) and stirred at reflux for 16 h. The reaction mixture was cooled to room temperature and concentrated under reduced pressure. The residue was taken in water and basified with triethyl amine to adjust a pH~8. The precipitated solid was filtered and washed with ethyl acetate. The separated organic layer from the filtrate was washed with water, brine solution, dried over anhydrous sodium sulfate, filtered and concentrated under reduced pressure to afford 6.0 g (83%) of diethyl 2-(4-aminophenyl)-2-methylmalonate as brown oil.

Step C: Preparation of Diethyl 2-methyl-2-(4-(piperazin-1-yl)phenyl)malonate. A suspension of diethyl 2-(4-aminophenyl)-2-methylmalonate (6.00 g, 22.6 mmol), Bis-(2-chloroethyl)amine. HCl (4.82 g, 27.2 mmol) in xylene (20 ml) was refluxed for 48 h. The reaction mixture was concentrated in vacuo and the residue was partitioned between saturated sodium bicarbonate solution and ethyl acetate. The separated organic layer was washed with water, brine solution, dried over anhydrous sodium sulfate, filtered and concentrated under reduced pressure to afford crude product. Purification by column chromatography over neutral alumina using 5% MeOH in CHCl$_3$ as eluent afford 4.80 g (63.5%) of diethyl 2-methyl-2-(4-(piperazin-1-yl)phenyl)malonate as brown oil.

Step D: Preparation of Diethyl 2-methyl-2-(4-(4-methylpiperazin-1-yl)phenyl)malonate. A mixture of formaldehyde (2 ml), formic acid (2 ml) and diethyl 2-methyl-2-(4-(piperazin-1-yl)phenyl)malonate (4.80 g, 14.4 mmol) was heated at reflux for 2 h and the reaction mixture was concentrated under reduced pressure. Saturated sodium bicarbonate solution was added and extracted with ethyl acetate. The organic layer was washed with water, brine solution, dried over anhydrous sodium sulfate, filtered and concentrated in vacuo to afford 3.50 g (70.0%) of diethyl 2-methyl-2-(4-(4-methylpiperazin-1-yl)phenyl)malonate as brown oily liquid.

Step E: Preparation of 2-(4-(4-methylpiperazin-1-yl)phenyl)propanoic acid. A solution of diethyl 2-(4-(4-methylpiperazin-1-yl)phenyl)malonate (3.50 g, 10.0 mmol) in conc. HCl (20 ml) was stirred for 18 h at reflux in a sealed tube. The reaction mixture was concentrated and co-distilled with toluene to afford (1.7 g, 70%) of 2-(4-(4-methylpiperazin-1-yl)phenyl)propanoic acid as dark brown solid.

Step F: Preparation of 2-(4-(4-Methylpiperazin-1-yl)phenyl)propanamide. A mixture of thionyl chloride (2 ml) and 2-(4-(4-methylpiperazin-1-yl)phenyl)propanoic acid (1.00 g, 4.03 mmol) was stirred for 1.5 h. The reaction mixture was concentrated under reduced pressure, the residue was taken in dry THF (10 ml), cooled to –78° C. and purged with ammonia gas until the solution becomes clear. The reaction mixture was slowly warmed to room temperature, the precipitate was filtered and washed with ethyl acetate. The filtrate was concentrated under reduced pressure to afford (0.5 g, 55%) of 2-(4-(4-methylpiperazin-1-yl)phenyl)propanamide as brownish white solid.

Preparation of Example 27. Example 27 was synthesized according to Method B starting from the above described 2-(4-(4-methylpiperazin-1-yl)phenyl)propanamide (200 mg, 0.81 mmol), 2-chloro-4-(4-fluoro-2-methoxyphenyl)pyridine (170 mg, 0.71 mmol), Cs$_2$CO$_3$ (0.53 g, 1.62 mmol), xantphos (42 mg, 70 μmol) and Tetrakis(triphenylphosphine) palladium (0) (37 mg, 30 μmol) in 1,4-dioxane (5 ml) at 120-125° C. for 3 h in a sealed tube, and was purified after usual workup by column chromatography to afford the product in a yield of 55.1%, followed by conversation to the HCl-salt by dissolving the above obtained compound (120 mg, 0.26 mmol) in acetone (3 ml) and addition of 2.2 eq. of ethereal HCl (0.60 ml, 0.58 mmol) at 0° C. for 30 min. The reaction mixture was triturated with n-pentane, dissolved in water and concentrated to dryness at 50° C. to obtain the HCl-salt in a yield of 64.5% as a pale yellow solid. $^1$H-NMR (HCl-salt, 400 MHz, DMSO-d$_6$): δ=11.80 (s, br., 1H), 11.00 (s, br., 1H), 8.32 (d, 1H), 8.16 (s, 1H), 7.49-7.40 (m, 2H), 7.34 (d, 2H), 7.13 (dd, 1H), 7.00-6.91 (m, 3H), 4.10-4.02 (m, 1H), 3.84 (s, 3H), 3.81-3.74 (m, 2H), 3.48-3.42 (m, 2H), 3.18-3.06 (m, 4H), 2.77 (d, 3H), 1.41 (d, 3H), HPLC (λ=214 nm, [A]): rt 11.1 min (93.7%), mp: starting at 102° C. and completely melts at 165° C.

Example 28

2-(4-(4-Methylpiperazin-1-yl)benzyl)-N-(4-(4-fluoro-2-methoxyphenyl)-pyridin-2-yl)propanamide Step A: Preparation of Diethyl 2-(4-nitrobenzyl)-2-methylmalonate. Diethyl methyl malonate (1.60 ml, 9.25 mmol) was added to a freshly prepared solution of sodium ethoxide solution [(sodium (212 mg, 9.25 mmol) in EtOH (20 ml)] and stirred for 1 h. 4-Nitrobenzyl bromide (2.00 g, 9.25 mmol) was added dropwise to the reaction mixture and stirred for 6 h at reflux. The reaction mixture was cooled to room temperature and concentrated. The residue was partitioned between water and CHCl$_3$. The separated organic layer was washed with water, brine solution, dried over anhydrous sodium sulfate, filtered and concentrated in vacuo to give the crude product. This was purified by column chromatography over silica gel (100-200 mesh) using 5% ethyl acetate in petroleum ether as eluent to afford 850 mg (29.7%) of diethyl 2-(4-nitrobenzyl)-2-methylmalonate as oily liquid.

Step B: Preparation of Diethyl 2-(4-aminobenzyl)-2-methylmalonate. Stannous chloride dihydrate (4.39 g, 19.4 mmol) was added to a solution of diethyl 2-(4-nitrobenzyl)-2-methylmalonate (3.00 g, 9.70 mmol) in EtOH (30 ml) and stirred at reflux for 3 h. Water and ethyl acetate were added and the solution was basified with triethyl amine adjusted an pH~9. The salts were filtered and washed with ethyl acetate. The organic layer was separated from the filtrate and washed with water, brine solution, dried over anhydrous sodium sulfate, filtered and concentrated under reduced pressure to afford 2.20 g (81.4%) of diethyl 2-(4-aminobenzyl)-2-methylmalonate as brown oil.

Step C: Preparation of Diethyl 2-(4-(piperazin-1-yl)benzyl)-2-methylmalonate. A solution of diethyl 2-(4-aminobenzyl)-2-methylmalonate (2.00 g, 7.17 mmol) and Bis-(2-chloroethyl)amine. HCl (1.90 g, 10.8 mmol) in xylene (10 ml) were heated at reflux for 48 h. The reaction mixture was concentrated and the residue was partitioned between saturated sodium bicarbonate solution and ethyl acetate. The separated organic layer was washed with water, brine solution, dried over anhydrous sodium sulfate, filtered and concentrated in vacuo to give the crude product. Purification by column chromatography over neutral alumina using 5% methanol in CHCl$_3$ as eluent afforded 1.90 g (76.3%) of diethyl 2-(4-(piperazin-1-yl)benzyl)-2-methylmalonate as brown oil.

Step D: Preparation of Diethyl 2-(4-(4-methylpiperazin-1-yl)benzyl)-2-methylmalonate. A mixture of diethyl 2-(4-(piperazin-1-yl)benzyl)-2-methylmalonate (500 mg, 1.43 mmol), formaldehyde (2 ml) and formic acid (2 ml) was heated at reflux for 2 h. The reaction mixture was concentrated and partitioned between saturated sodium bicarbonate solution and ethyl acetate. The organic layer was separated and washed with water, brine solution, dried over anhydrous sodium sulfate, filtered and concentrated to afford 400 mg (86.8%) of diethyl 2-(4-(4-methylpiperazin-1-yl)benzyl)-2-methylmalonate as brown oil.

Step E: Preparation of 2-(4-(4-Methylpiperazin-1-yl)benzyl)propanoic acid. A solution of diethyl 2-(4-(4-methylpiperazin-1-yl)benzyl)-2-methylmalonate (1.50 g, 4.29 mmol) in conc. HCl (10 ml) was stirred at 130-140° C. in a sealed tube for 18 h. The reaction mixture was concentrated and co-distilled with toluene to afford 700 mg (63.6%) of 2-(4-(4-methylpiperazin-1-yl)benzyl)propanoic acid as dark brown solid.

Step F: Preparation of 2-(4-(4-Methylpiperazin-1-yl)benzyl)propanamide. A mixture of thionyl chloride (2 ml) and 2-(4-(4-methylpiperazin-1-yl)benzyl)propanoic acid (500 mg, 1.91 mmol) was stirred for 1.5 h. The reaction mixture was concentrated at below 50° C. under reduced pressure. The residue was taken into dry THF (5 ml), cooled to –78° C. and purged with ammonia gas. The reaction mixture was slowly warmed to room temperature, the solid was filtered and washed with ethyl acetate. The filtrate was concentrated under reduced pressure to afford 300 mg (60.2%) of 2-(4-(4-methylpiperazin-1-yl)benzyl)propanamide as brownish white solid.

Preparation of Example 28. Example 28 was synthesized according to Method B starting from the above described 2-(4-(4-methylpiperazin-1-yl)benzyl)propanamide (200 mg, 0.77 mmol), 2-chloro-4-(4-fluoro-2-methoxyphenyl)pyridine (163 mg, 0.68 mmol), $Cs_2CO_3$ (378 mg, 1.14 mmol), xantphos (29 mg, 26 μmol) and Tetrakis(triphenylphosphine)palladium (0) (12 mg, 11 μmol) in 1,4-dioxane (5 ml) at 120-125° C. for 4 h in a sealed tube, and was purified after usual workup by column chromatography to afford the product in a yield of 35.3%, followed by conversation to the HCl-salt by dissolving the above obtained compound (125 mg, 0.27 mmol) in acetone (3 ml) and addition of 2.2 eq. of ethereal HCl (0.6 ml, 0.6 mmol, 1 M). The reaction mixture was triturated with n-pentane, dissolved in water and concentrated at 50° C. to afford the HCl-salt in a yield of 58.1% as a pale yellow solid. $^1$H-NMR (HCl-salt, 400 MHz, DMSO-$d_6$): δ=11.50 (s, br., 1H), 10.90 (s, br., 1H), 8.33 (d, 1H), 8.17 (s, 1H), 7.46 (t, 1H), 7.43-7.39 (m, 1H), 7.17-7.11 (m, 3H), 6.99-6.89 (m, 3H), 3.85 (s, 3H), 3.74 (d, 2H), 3.48-3.42 (m, 2H), 3.15-2.92 (m, 7H), 2.78 (d, 3H), 1.09 (d, 3H), HPLC (λ=214 nm, [A]): rt 11.4 min (98.5%), mp: starting at 160° C. and completely melts at 185° C.

Example 29

N-(4-(4-Fluoro-2-methoxyphenyl)pyridin-2-yl)-3-(4-(4-methylpiperazin-1-yl)phenyl)butanamide Step A: Preparation of 1-(4-(4-Methylpiperazin-1-yl)phenyl)ethanone. A solution of 4-fluoro acetophenone (5.0 g, 3.6 mmol) and N-methyl piperazine (20 ml, 4 vol %) was heated in a sealed tube at 120° C. for 16 h. The reaction mixture was cooled to room temperature and poured into ice water. The precipitated solid was filtered and dried in vacuo to afford 7.50 g (94.5%) of 1-(4-(4-methylpiperazin-1-yl)phenyl)ethanone as solid.

Step B: Preparation of (Z)-Ethyl 2-cyano-3-(4-(4-methylpiperazin-1-yl)phenyl)but-2-enoate. Ethyl cyano acetate (3.12 g, 27.6 mmol), ammonium acetate (123 mg, 1.76 mmol), acetic acid (0.2 ml, 3.5 mmol) were added successively to a stirred solution of 1-(4-(4-methylpiperazin-1-yl)phenyl)ethanone (5.0 g, 23 mmol) in benzene (25 ml) and stirred for 36 h at 135-140° C. The reaction mixture was poured into water and extracted with ethyl acetate. The combined organic layer was washed with brine, dried over anhydrous sodium sulfate, filtered and concentrated under reduced pressure to give the crude product. This was purified by column chromatography using 2% methanol in $CHCl_3$ as eluent to afford (Z)-ethyl 2-cyano-3-(4-(4-methylpiperazin-1-yl)phenyl)but-2-enoate as yellow liquid 2.30 g (32.4%).

Step C: Preparation of Methyl 2-cyano-3-(4-(4-methylpiperazin-1-yl)phenyl)butanoate. (Z)-ethyl 2-cyano-3-(4-(4-methylpiperazin-1-yl)phenyl)but-2-enoate (700 mg, 2.30 mmol) was added to a stirred mixture of Mg metal (2.10 g, 89.4 mmol) in methanol (20 ml) at 0° C. and stirred for 2 h at room temperature (reaction was activated by Mg metal, so exothermic). Then the reaction mixture was quenched with 6N HCl (20 ml) up to a clear solution was obtained. The reaction mixture was washed with ethyl acetate (2×20 ml), basified with saturated sodium bicarbonate and extracted with DCM (3×50 ml). The combined organic layer was washed with water, brine, dried over anhydrous sodium sulfate, filtered and concentrated under reduced pressure to afford 400 mg (54%) of methyl 2-cyano-3-(4-(4-methylpiperazin-1-yl)phenyl)butanoate as a colorless liquid.

Step D: Preparation of 3-(4-(4-Methylpiperazin-1-yl)phenyl)butanenitrile. A mixture of methyl 2-cyano-3-(4-(4-methylpiperazin-1-yl)phenyl)butanoate (700 mg, 2.32 mmol), sodium chloride (405 mg, 6.90 mmol), DMSO (5 ml) and water (2 ml, 3 vol %) and heated at 160-165° C. for 12 h. The reaction mixture was poured into water and extracted with ethyl acetate. The organic layer was washed with water, brine, dried over anhydrous sodium sulfate, filtered and concentrated in vacuo to afford 450 mg (79.6%) of 3-(4-(4-methylpiperazin-1-yl)phenyl)butanenitrile as a colorless liquid.

Step E: Preparation of 3-(4-(4-Methylpiperazin-1-yl)phenyl)butanamide. A suspension of 3-(4-(4-methylpiperazin-1-yl)phenyl)butanenitrile (450 mg, 1.85 mmol) and poly phosphoric acid (4.5 g) was heated at 90° C. for 3 h. The reaction mixture was cooled to room temperature, diluted with cold water and basified with saturated sodium bicarbonate solution. The aqueous layer was extracted with DCM, washed with water and brine solution. The organic layer was dried over sodium sulfate, filtered and concentrated in vacuo to afford 360 mg (74%) of 3-(4-(4-methylpiperazin-1-yl)phenyl)butanamide as light yellow color solid.

Preparation of Example 29. Example 29 was synthesized according to Method B starting from the above described 3-(4-(4-methylpiperazin-1-yl)phenyl)butanamide (120 mg, 0.46 mmol), 2-chloro-4-(4-fluoro-2-methoxyphenyl)pyridine (130 mg, 0.55 mmol), $Cs_2CO_3$ (223 mg, 0.68 mmol), xantphos (24 mg, 40 μmol) and Tetrakis(triphenylphosphine)palladium (0) (21 mg, 18 μmol) in 1,4-dioxane (8 ml) at 125° C. for 4 h in a sealed tube, and was purified after usual workup by preparative TLC to afford the product in a yield of 28.2%, followed by conversation to the HCl-salt by dissolving the above obtained compound (60.0 mg, 129 μmol) in acetone (2 ml) and addition of 2.2 eq. of ethereal HCl (0.28 ml, 0.28 mmol, 1 M) at 0° C. for 1 h. The reaction mixture was triturated with ether and dried in vacuum to give the HCl-salt in a yield of 77.1% as a light yellow solid. $^1$H-NMR (HCl-salt, 400 MHz, DMSO-$d_6$): δ=10.60 (s, 1H), 10.07 (s, br., 1H), 8.29 (d, 1H), 8.13 (s, 1H), 7.37 (dd, 1H), 7.22 (dd, 1H), 7.19-7.14 (m, 2H), 7.08 (dd, 1H), 6.95-6.89 (m, 3H), 3.81 (s, 3H), 3.80-3.71 (m, 2H), 3.50-3.43 (m, 2H), 3.26-3.16 (m, 1H), 3.16-3.05 (m, 2H), 3.03-2.90 (m, 2H), 2.80 (d, 3H), 2.70-2.61 (m, 2H), 1.20 (d, 3H), HPLC (λ=214 nm, [A]): rt 11.3 min (97.0%), mp: starting at 70° C. and completely melts at 160° C.

Example 30

N-(4-(4-Fluoro-2-methoxyphenyl)pyridin-2-yl)-4-(pyridin-2-ylamino)-cis-cyclohexanecarboxamide Step A: Preparation of 2-Azabicyclo[2.2.2]octan-3-one. cis-4-Aminocyclohexyl carboxylic acid (1.60 g, 11.2 mmol) was heated to 290° C. for 15 min. After completion of the reaction, the reaction mixture was suspended in DCM and filtered. The organic layer was evaporated to dryness to afford 1.20 g (86.3%) of 2-azabicyclo[2.2.2]octan-3-one as an off white solid.

Step B: Preparation of 2-(Pyridin-2-yl)-2-aza-bicyclo[2.2.2]octan-3-one. A mixture of 2-azabicyclo[2.2.2]octan-3-one (0.6 g, 4.8 mmol), 2-chloropyridine (0.65 g, 5.76 mmol), $Cs_2CO_3$ (2.36 g, 7.20 mmol) and xantphos (0.22 g, 0.38 mmol) in 1,4-dioxane (30 ml) was purged with argon gas for 15 min. Tetrakis(triphenylphosphine)palladium (0) (0.22 g, 0.19 mmol) was added and continued purging for another 10 min. The reaction mixture was heated at 125° C. for 3 h. The reaction mixture was cooled to room temperature and filtered. The filtrate was concentrated and dried under reduced pressure to afford the crude compound. Purification by column chromatography over neutral alumina using 15% ethyl acetate in petroleum ether as eluent afforded 600 mg (61.9%) of 2-(pyridin-2-yl)-2-aza-bicyclo[2.2.2]octan-3-one as pale yellow solid.

Step C: Preparation of cis-4-(Pyridin-2-ylamino)cyclohexanecarboxylic acid. A solution of 2-(pyridin-2-yl)-2-azabicyclo[2.2.2]octan-3-one (0.60 g, 2.97 mmol) in 2N HCl (15 ml) was heated at reflux for 17 h. The solvent was removed under reduced pressure and water was added. The reaction mixture was made alkaline using saturated sodium bicarbonate solution and extracted with DCM. The combined organic layer was washed with water, brine solution, dried over anhydrous sodium sulfate, filtered and concentrated to afford 500 mg of cis-4-(pyridin-2-ylamino)cyclohexanecarboxylic acid (76.5%) as off-white solid.

Step D: Preparation of cis-4-(Pyridin-2-ylamino)cyclohexanecarboxamide.cis-4-(pyridin-2-ylamino)cyclohexanecarboxylic acid (0.22 g, 1.00 mmol) was dissolved in thionyl chloride (2 ml) at room temperature and stirred for 1 h. The reaction mixture was concentrated under reduced pressure to yield the crude acid chloride, which was added to liquid ammonia/THF (1:1, 15 ml) and allowed to stir at room temperature. The reaction mixture was diluted with DCM and filtered. The filtrate was concentrated under reduced pressure to afford 100 mg of cis-4-(pyridin-2-ylamino)cyclohexanecarboxamide as off white solid.

Preparation of Example 30. Example 30 was synthesized according to Method B starting from the above described cis-4-(pyridin-2-ylamino)cyclohexanecarboxamide (100 mg, 0.45 mmol), $Cs_2CO_3$ (225 mg, 0.68 mmol), 2-chloro-4-(4-fluoro-2-methoxyphenyl)pyridine (130 mg, 0.54 mmol), xantphos (21 mg, 36 μmol) and Tetrakis(triphenylphosphine) palladium (0) (21 mg, 18 μmol) in dry 1,4-dioxane (5 ml) at 120-125° C. for 3 h in a sealed tube. The compound was purified after usual workup by preparative TLC to afford the product in a yield of 29.4%, followed by conversation to the HCl-salt by dissolving the above obtained compound (60.0 mg, 0.14 mmol) in acetone (4 ml) and addition of 1.2 eq. of ethereal HCl (0.17 ml, 0.17 mmol, 1 M) at 0° C. for 30 min. The reaction mixture was triturated with n-pentane, dried, dissolved in Millipore water and evaporated under reduced pressure at 50° C. to afford 50 mg (76.5%) of the HCl-salt as off white solid. $^1$H-NMR (HCl-salt, 400 MHz, DMSO-$d_6$): δ=13.84 (s, br., 1H), 11.54 (s, br., 1H), 8.89 (s, 1H), 8.35 (d, 1H), 8.20 (s, 1H), 7.95-7.84 (m, 2H), 7.52-7.41 (m, 2H), 7.22 (d, 1H), 7.14 (dd, 1H), 7.01-6.93 (m, 1H), 6.84 (d, 1H), 4.08-3.98 (m, 1H), 3.86 (s, 3H), 2.81-2.71 (m, 1H), 2.02-1.90 (m, 2H), 1.86-1.71 (m, 6H), HPLC (λ=214 nm, [A]): rt 10.2 min (99.6%).

Example 31

N-(4-(4-Fluoro-2-methoxyphenyl)pyridin-2-yl)-2-(2-(4-methylpiperazin-1-yl)pyridin-4-yl)acetamide Step A: Preparation of 2-tert-Butyl-1,3-dicyclohexylisourea. A suspension of dicyclohexyl carbodiimide (2.00 g, 9.70 mmol), tert-butanol (1.00 ml, 10.6 mmol) and a catalytic amount of copper chloride (9.0 mg, 90 μmol) was stirred at room temperature for 24 h. The reaction mixture was filtered through a pad of celite, washed with $CHCl_3$ (5 ml) and the solvent was evaporated under vacuum to afford 2.5 g (74%) of compound 2-tert-butyl-1,3-dicyclohexylisourea as a pale green thick liquid.

Step B: Preparation of Diethyl 2-(2-chloropyridin-4-yl)malonate. 2-Chloro-4-picoline was added to a solution of potassium hydride (1.80 g, 15.8 mmol) in diethyl carbonate (10 ml) at 0° C. The reaction mixture was allowed to attain room temperature and stirred overnight. The reaction mixture was quenched with saturated ammonium chloride (15 ml) and extracted with ethyl acetate. The combined organic layer was dried over anhydrous sodium sulfate, filtered and concentrated in vacuum to afford the crude product. Purification by column chromatography over silica gel (60-120 mesh) using 8% ethyl acetate in petroleum ether as eluent afforded 750 mg (36%) of diethyl 2-(2-chloropyridin-4-yl)malonate as colorless liquid.

Step C: Preparation of 2-(2-Chloropyridin-4-yl)acetic acid. A solution of diethyl 2-(2-chloropyridin-4-yl)malonate (1.30 g, 4.79 mmol) in conc. HCl (15 ml) was refluxed for 18 h. The reaction mixture was cooled to room temperature, concentrated and co-distilled with toluene (2×20 ml) to afford the crude product. Purification by triturating with diethyl ether afforded 500 mg (57%) of 2-(2-chloropyridin-4-yl)acetic acid as a white solid.

Step D: Preparation of tert-Butyl 2-(2-chloropyridin-4-yl)acetate. Compound 2-tert-butyl-1,3-dicyclohexylisourea (650 mg, 2.30 mmol) was added to a solution of 2-(2-chloropyridin-4-yl)acetic acid (200 mg, 1.16 mmol) in DCM (5 ml) at room temperature. The reaction mixture was stirred for 24 h, filtered, washed with DCM (5 ml) and saturated sodium bicarbonate solution (10 ml). The solvent was evaporated in vacuum to afford 200 mg (77%) of tert-butyl 2-(2-chloropyridin-4-yl)acetate as a colorless liquid.

Step E: Preparation of 1-(4-Methylpiperazin-1-yl)-2-(2-(4-methylpiperazin-1-yl)pyridin-4-yl)ethanone. A suspension of tert-butyl 2-(2-chloropyridin-4-yl)acetate (600 mg, 2.64 mmol) and N-methyl piperazine (2 ml) was heated in a sealed tube for 24 h at 140° C. The reaction mixture was cooled to room temperature, water was added and extracted with DCM. The combined organic layer was washed with brine, dried over anhydrous sodium sulfate, filtered and concentrated under vacuum to get the crude product. Purification by column chromatography over neutral alumina using 5% MeOH in $CHCl_3$ as eluent afforded 600 mg (71%) of 1-(4-methylpiperazin-1-yl)-2-(2-(4-methylpiperazin-1-yl)pyridin-4-yl)ethanone as colorless liquid.

Step F: Preparation of 2-(2-(4-Methylpiperazin-1-yl)pyridin-4-yl)acetic acid. A solution of 1-(4-methylpiperazin-1-yl)-2-(2-(4-methylpiperazin-1-yl)pyridin-4-yl)ethanone (800 mg, 2.52 mmol) in conc. HCl (10 ml) was refluxed for 12 h. The reaction mixture was cooled to room temperature and concentrated. The residue was co-distilled with toluene twice to afford crude 450 mg of 2-(2-(4-methylpiperazin-1-yl)pyridin-4-yl)acetic acid. The crude was taken as such for the next step.

Step G: Preparation of Methyl 2-(2-(4-methylpiperazin-1-yl)pyridin-4-yl)acetate. Thionyl chloride (0.9 ml) was added to a solution of 2-(2-(4-methylpiperazin-1-yl)pyridin-4-yl)acetic acid (900 mg, 3.82 mmol) in MeOH (15 ml) at 0° C. The reaction mixture was heated for 4 h at 85° C. and concentrated. The residue was partitioned between ethyl acetate and saturated sodium bicarbonate solution. The organic layer was separated and the aqueous layer was extracted with ethyl acetate. The combined organic layer was washed with brine, dried over anhydrous sodium sulfate, filtered and concentrated under vacuum to afford 750 mg (78%) of methyl 2-(2-(4-methylpiperazin-1-yl)pyridin-4-yl)acetate as a colorless liquid.

Step H: Preparation of 2-(2-(4-Methylpiperazin-1-yl)pyridin-4-yl)acetamide. A solution of methyl 2-(2-(4-methylpiperazin-1-yl)pyridin-4-yl)acetate (750 mg, 2.81 mmol) in methanolic ammonia (10 ml) was heated in a steel bomb at 90° C. for 72 h. The reaction mixture was cooled to room temperature, concentrated and dried in vacuum to afford the crude product. Purification by triturating with diethyl ether afforded 370 mg (31%) of 2-(2-(4-methylpiperazin-1-yl)pyridin-4-yl)acetamide as a light brown color solid.

Preparation of Example 31. Example 31 was synthesized according to Method B starting from the above described 2-(2-(4-methylpiperazin-1-yl)pyridin-4-yl)acetamide (150.0 mg, 0.650 mmol), 2-chloro-4-(4-fluoro-2-methoxyphenyl)pyridine (182.0 mg, 0.754 mmol), $Cs_2CO_3$ (313 mg, 0.96 mmol), xantphos (34 mg, 50 mol) and Tetrakis(triphenylphosphine)palladium (0) (29 mg, 25 μmol) in 1,4-dioxane (10 ml) at 120-125° C. for 4 h in a sealed tube, and was purified after usual workup by preparative TLC to afford the product in a yield of 19.6%, followed by conversation to the HCl-salt by dissolving the above obtained compound in acetone (2 ml) and addition of 1.1 eq. of ethereal HCl (0.10 ml, 0.10 mmol, 1M) at 0° C. for 1 h. The reaction mixture was triturated with diethyl ether and dried in vacuum to afford 35 mg (81%) of the HCl-salt as a pale yellow solid. $^1$H-NMR (HCl-salt, 400 MHz, DMSO-d): δ=11.35-11.28 (m, 1H), 8.96 (s, 1H), 8.65 (s, 1H), 8.09 (d, 1H.02), 7.98 (dd, 1H), 7.37-7.27 (m, 1H), 7.12 (dd, 1H), 7.02-6.91 (m, 2H), 4.52-4.40 (m, 2H), 3.97-3.92 (m, 2H), 3.86 (s, 3H), 3.59-3.49 (m, 4H), 3.23-3.11 (m, 2H), 2.81-2.77 (m, 3H), HPLC (λ=214 nm, [A]): rt 9.1 min (100%).

Example 32 cis-N-(4-(4-Fluoro-2-methoxyphenyl)pyridin-2-yl)-4-(pyridin-4-ylamino)-cyclohexanecarboxamide Step A: Preparation of 2-Azabicyclo[2.2.2]octan-3-one
2-Azabicyclo[2.2.2]octan-3-one was prepared as described above.

Step B: Preparation of 2-(Pyridin-4-yl)-2-aza-bicyclo[2.2.2]octan-3-one
A mixture of 2-azabicyclo[2.2.2]octan-3-one (0.6 g, 4.8 mmol), 4-bromopyridine hydrochloride (1.17 g, 5.76 mmol), $Cs_2CO_3$ (2.36 g, 7.20 mmol) and xantphos (0.22 g, 0.38 mmol) was purged with argon gas for 10 min. Tetrakis(triphenylphosphine)palladium (0) (0.22 g, 0.19 mmol) was added and degassed for another 10 min. The reaction mixture was heated at 125° C. for 3 h. The reaction mixture was cooled to room temperature and filtered. The filtrate was concentrated and dried under reduced pressure to afford the crude compound. Purification by column chromatography over neutral alumina using 0.5% MeOH in $CHCl_3$ as eluent afforded 600 mg (61.9%) of 2-(pyridin-4-yl)-2-aza-bicyclo[2.2.2]octan-3-one as pale yellow solid.

Step C: Preparation of cis-4-(Pyridin-4-ylamino)cyclohexanecarboxylic acid. A solution of 2-(pyridin-4-yl)-2-azabicyclo[2.2.2]octan-3-one (0.60 g, 2.97 mmol) in 2N HCl (15 ml) was heated at reflux for 17 h. The solvent was removed and dried under reduced pressure to afford 600 mg of cis-4-(pyridin-4-ylamino)cyclohexanecarboxylic acid (76.5%) as off-white solid which was used for the next step.

Step D: Preparation of cis-4-(Pyridin-4-ylamino)cyclohexanecarboxamide. cis-4-(Pyridin-4-ylamino)cyclohexanecarboxylic acid (600 mg, 2.74 mmol) was dissolved in thionyl chloride (2 ml) at room temperature and stirred for 1 h. The reaction mixture was concentrated under reduced pressure to yield the crude acid chloride, which was added to liquid ammonia/THF (1:1, 15 ml) and allowed to stir at room temperature. The reaction mixture was diluted with DCM and filtered. The filtrate was concentrated under reduced pressure to afford 400 mg (68%) of cis-4-(pyridin-4-ylamino)cyclohexanecarboxamide as white solid.

Preparation of Example 32. Example 32 was synthesized according to Method B starting from the above described cis-4-(pyridin-4-ylamino)cyclohexanecarboxamide (100 mg, 0.45 mmol), $Cs_2CO_3$ (225 mg, 0.68 mmol), 2-chloro-4-(4-fluoro-2-methoxyphenyl)pyridine (130 mg, 0.54 mmol), xantphos (21 mg, 36 mol) and Tetrakis(triphenylphosphine)palladium (0) (21 mg, 18 mmol) in 1,4-dioxane (5 ml) at 120-125° C. for 4 h in a sealed tube, and was purified after usual workup by column chromatography over neutral alumina using 0-1% MeOH in $CHCl_3$ to afford the product in a yield of 26.0%, followed by the conversation to the HCl-salt by dissolving the above obtained compound (60.0 mg, 0.14 mmol) in acetone (4 ml) and addition of 2.0 eq. of ethereal HCl (0.28 ml, 0.28 mmol, 1 M). The reaction mixture was triturated with n-pentane and dissolved in water and evaporated under reduced pressure at 50° C. to obtain the HCl-salt in a yield of 76.5% as a pale yellow solid. $^1$H-NMR (HCl-salt, 400 MHz, DMSO-$d_6$): δ=13.35-13.18 (m, 1H), 8.56-8.48 (m, 1H), 8.31 (d, 1H), 8.23-8.18 (m, 2H), 8.08-8.04 (m, 1H), 7.42-7.36 (m, 1H), 7.26-7.21 (m, 1H), 7.12-7.07 (m, 1H), 7.03-6.99 (m, 1H), 6.95-6.88 (m, 1H), 3.82 (s, 3H), 2.72-2.65 (m, 1H), 1.94-1.66 (m, 9H), HPLC (λ=214 nm, [A]): rt 10.4 min (98.3%), mp: 260° C.

Example 33 cis-3-Acetamido-N-(4-(4-fluoro-2-methoxyphenyl)pyridin-2-yl)cyclo-hexanecarboxamide Step A: Preparation of cis-Methyl 3-aminocyclohexanecarboxylate. Thionyl chloride (0.6 ml) was added to solution of cis-3-amino-cyclohexanecarboxylic acid (bought from AMRI, USA, cat.-no.: A00342, 0.50 g, 2.80 mmol) in MeOH (20 ml) at 0° C. and stirred at reflux for 12 h. The volatiles were evaporated in vacuo and the resulting residue was partitioned between saturated sodium bicarbonate solution and ethyl acetate. The separated organic layer was washed with brine, dried over anhydrous sodium sulfate, filtered and concentrated under vacuo to afford 400 mg (90.9%) of cis-methyl 3-aminocyclohexanecarboxylate as colorless liquid.

Step B: Preparation of cis-Methyl 3-acetamidocyclohexanecarboxylate. Acetic anhydride (1.20 ml, 12.7 mmol) was added to a stirred solution of cis-methyl 3-aminocyclohexanecarboxylate (0.40 g, 2.54 mmol) in pyridine (10 ml) under an atmosphere of argon and stirred for 3 h at room temperature. The excess pyridine was removed under vacuo and the resulting residue was partitioned between DCM and saturated sodium bicarbonate solution. The separated organic layer was washed with water, brine, dried over anhydrous sodium sulfate, filtered and concentrated under vacuo to afford cis-methyl 3-acetamidocyclohexanecarboxylate (350 mg, 69.0%) as a colorless liquid.

Step C: Preparation of cis-3-Acetamidocyclohexanecarboxamide. A mixture of cis-methyl 3-acetamidocyclohexanecarboxylate (350 mg, 1.75 mmol) and methanolic ammonia (20 ml) was stirred for 72 h at 90° C. in a steel bomb. The reaction mixture was cooled to room temperature and concentrated under reduced pressure to afford the crude product which was washed with n-pentane to afford 200 mg (57.1%) of cis-3-acetamidocyclohexanecarboxamide as white color solid.

Preparation of Example 33. Example 33 was synthesized according to Method B starting from the above described cis-3-acetamidocyclohexanecarboxamide (250 mg, 1.35 mmol), 2-chloro-4-(4-fluoro-2-methoxyphenyl)pyridine (386 mg, 1.63 mmol), Cs$_2$CO$_3$ (660 mg, 2.02 mmol), xantphos (71.0 mg, 121 µmol) and Tetrakis(triphenylphosphine)palladium (0) (62 mg, 54 µmol) in 1,4-dioxane (10 ml) at 125° C. for 4 h in a sealed tube, and was purified after usual workup by preparative TLC to afford the product in a yield of 31.8%, followed by conversation to the HCl-salt by dissolving the above obtained compound (100 mg, 0.26 mmol) in acetone (5 ml) and addition of 1.2 eq. of ethereal HCl (0.31 ml, 0.31 mmol, 1 M) at 0° C. for 30 min. The reaction mixture was triturated with diethyl ether and dried to give the HCl-salt in a yield of 64.2%. $^1$H-NMR (HCl-salt, 400 MHz, DMSO-d$_6$): δ=8.31 (d, 1H), 8.06 (s, 1H), 7.80 (d, 1H), 7.45-7.40 (m, 1H), 7.34-7.30 (m, 1H), 7.10 (dd, 1H), 6.95-6.89 (m, 1H), 3.82 (s, 3H), 3.62-3.53 (m, 1H), 2.66-2.54 (m, 1H), 1.94-1.88 (m, 1H), 1.82-1.72 (m, 5H), 1.34-1.22 (m, 4H), 1.13-1.03 (m, 1H), HPLC (λ=214 nm, [A]): rt 11.4 min (100%), mp: 198° C.

Example 34

(1R,3S)-3-Acetamido-N-(4-(4-fluoro-2-methoxyphenyl)pyridin-2-yl)cyclopentanecarboxamide Step A: Preparation of (1R,3S)-Methyl 3-aminocyclopentanecarboxylate. Thionyl chloride (1.30 ml, 18.2 mmol) was added to a stirred solution of (1R,3S)-3-amino cyclo pentyl carboxylic acid (2.00 g, 12.1 mmol) in MeOH (20 ml) and refluxed for 3 h. The reaction mixture was concentrated under reduced pressure and co-distilled with toluene to afford 1.9 g (87%) of (1R,3S)-methyl 3-aminocyclopentanecarboxylate as off-white solid.

Step B: Preparation of (1R,3S)-Methyl 3-acetamidocyclopentanecarboxylate. Acetic anhydride (0.07 ml, 7.00 mmol) was added to a stirred solution of (1R,3S)-methyl 3-aminocyclopentanecarboxylate (200 mg, 1.39 mmol) in pyridine (5 ml) and stirred for 15 h at ambient temperature. The reaction mixture was concentrated under reduced pressure, water and CHCl$_3$ were added. The organic layer was separated and washed with saturated sodium bicarbonate solution, brine solution, dried over anhydrous sodium sulfate, filtered and concentrated under reduced pressure to afford 180 mg (69%) of (1R,3S)-methyl 3-acetamidocyclopentanecarboxylate as brown oil.

Step C: Preparation of (1R,3S)-3-Acetamidocyclopentanecarboxamide. Ammonia gas was passed into a solution of (1R,3S)-methyl 3-acetamidocyclopentanecarboxylate (180 mg, 0.96 mmol) in MeOH (5 ml) at −78° C. in a pressure bomb. The reaction mixture was slowly warmed up to room temperature and stirred for 18 h at 100° C. The reaction mixture was concentrated under reduced pressure to afford 150 mg of (1R,3S)-3-acetamidocyclopentanecarboxamide as brown oil.

Preparation of Example 34. Example 34 was synthesized according to Method B starting from the above described (1R,3S)-3-Acetamidocyclopentanecarboxamide (300 mg, 1.76 mmol), 2-chloro-4-(4-fluoro-2-methoxyphenyl)pyridine (501 mg, 2.11 mmol), Cs$_2$CO$_3$ (870 mg, 2.64 mmol), xantphos (82.0 mg, 0.141 µmol) and Tetrakis(triphenylphosphine)palladium (0) (82 mg, 70 µmol) in 1,4-dioxane (10 ml) at 120-125° C. for 15 h in a sealed tube, and was purified after usual workup by column chromatography over neutral alumina using 0-2% MeOH in CHCl$_3$ and triturating with ether to afford the product in a yield of 9.8%, followed by conversation to the HCl-salt by dissolving the above obtained compound in acetone (3 ml) and addition of 1.2 eq. of ethereal HCl (0.20 ml, 0.19 mmol, 1 M) to obtain the HCl-salt after usual workup as an off white solid in a yield of 83.9%. $^1$H-NMR (HCl-salt, 400 MHz, DMSO-d$_6$): δ=8.34 (d, 1H), 8.12 (s, 1H), 7.96 (d, 1H), 7.50-7.45 (m, 1H), 7.41 (d, 1H), 7.14 (dd, 1H), 6.99-6.93 (m, 1H), 4.08-4.00 (m, 1H), 3.85 (s, 3H), 3.07-2.98 (m, 1H), 2.23-2.15 (m, 1H), 1.92-1.83 (m, 3H), 1.78 (s, 3H), 1.67-1.56 (m, 1H), 1.54-1.44 (m, 1H), HPLC (λ=214 nm, [A]): rt 10.8 min (100%), mp: 95° C.

Example 35 cis-N-(4-(4-Fluoro-2-methoxyphenyl)pyridin-2-yl)-4-(thiazol-2-ylamino)-cyclohexanecarboxamide Step A: Preparation of 2-Azabicyclo[2.2.2]octan-3-one. 2-Azabicyclo[2.2.2]octan-3-one was prepared as described above.

Step B: Preparation of 2-(Thiazol-2-yl)-2-aza-bicyclo[2.2.2]octan-3-one. A mixture of 2-azabicyclo[2.2.2]octan-3-one (0.5 g, 4.0 mmol), 2-bromothiazole (0.79 g, 4.81 mmol), Cs$_2$CO$_3$ (2.0 g, 6.0 mmol), xantphos (0.19 g, 0.32 mmol) and 1,4-dioxane (25 ml) was degassed with argon gas for 15 min. Tetrakis(triphenylphosphine)palladium (0) (0.18 g, 0.16 mmol) was added, degassed for another 15 min and stirred at 125° C. for 3 h in a sealed tube. After cooling to room temperature the reaction mixture was filtered and the filtrate was evaporated under reduced pressure to afford the crude compound. Purification by column chromatography over neutral alumina using 10% ethyl acetate in petroleum ether as eluent afford 500 mg (60%) of 2-(thiazol-2-yl)-2-aza-bicyclo[2.2.2]octan-3-one as pale yellow solid.

Step C: Preparation of cis-4-(Thiazol-2-ylamino)cyclohexanecarboxylic acid. A solution of 2-(thiazol-2-yl)-2-azabicyclo[2.2.2]octan-3-one (0.50 g, 2.43 mmol) in 2N HCl (15 ml) was heated at reflux for 17 h. The solvent was removed under reduced pressure and the residue was partitioned between saturated sodium bicarbonate solution and CHCl$_3$. The separated organic layer was washed with brine solution, dried over anhydrous sodium sulfate, filtered and evaporated to dryness to afford 0.2 g of cis-4-(thiazol-2-ylamino)cyclohexanecarboxylic acid (36.8%) as off white solid.

Step D: Preparation of cis-4-(Thiazol-2-ylamino)cyclohexanecarboxamide. A solution of cis-4-(thiazol-2-ylamino)cyclohexanecarboxylic acid (200 mg, 0.88 mmol) in thionyl chloride (1 ml) was stirred for 1 h at room temperature. The excess thionyl chloride was removed in vacuo to give the crude acid chloride. Liquid ammonia/THF (1:1, 15 ml) was added to the above prepared acid chloride solution at −60° C. and allowed to warm up to room temperature. The reaction mixture was diluted with 10% MeOH in DCM and filtered. The filtrate was concentrated under reduced pressure to afford 140 mg (70%) of cis-4-(thiazol-2-ylamino)cyclohexanecarboxamide as white solid.

Preparation of Example 35. Example 35 was synthesized according to Method B starting from the above described cis-4-(thiazol-2-ylamino)cyclohexanecarboxamide (140 mg, 0.62 mmol), Cs$_2$CO$_3$ (310 mg, 0.93 mmol), 2-chloro-4-(4-fluoro-2-methoxyphenyl)pyridine (170 mg, 0.74 mmol), xantphos (28 mg, 49 mol) and Tetrakis(triphenylphosphine)palladium (0) (28 mg, 25 µmol) in 1,4-dioxane (4 ml) at 125° C. for 3 h in a sealed tube, and was purified after usual workup by column chromatography over neutral alumina using 0-2% MeOH in CHCl$_3$ to afford the product in a yield of 30.1%, followed by conversation to the HCl-salt by dissolving the above obtained compound (80.0 mg, 0.19 mmol) in acetone (4 ml) and addition of 1.2 eq. of ethereal HCl (0.23 ml, 0.23 mmol, 1 M) to obtain the HCl-salt after trituration the compound with n-pentane and lyophilization in a yield of 72.5% as pale yellow solid. $^1$H-NMR (HCl-salt, 400 MHz, DMSO-d$_6$): δ=8.34-8.31 (m, 1H), 8.17 (s, br., 1H), 7.45-7.38 (m, 1H), 7.36-7.33 (m, 1H), 7.31-7.22 (m, 1H), 7.14-7.08 (m, 1H), 6.98-6.90 (m, 2H), 3.82 (s, 3H), 2.71-2.63 (m, 1H), 2.54-2.50 (m, 1H), 1.90-1.78 (m, 4H), 1.77-1.65 (m, 4H), HPLC (λ=214 nm, [A]): rt 10.4 min (95.4%), mp: 85° C.

Example 36 cis-N-(4-(4-Fluoro-2-methoxyphenyl)pyridin-2-yl)-4-(phenylamino)-cyclohexanecarboxamide Step A: Preparation of 2-Azabicyclo[2.2.2]octan-3-one. 2-Azabicyclo[2.2.2]octan-3-one was prepared as described above.

Step B: Preparation of 2-Phenyl-2-aza-bicyclo[2.2.2]octan-3-one. A mixture of 2-azabicyclo[2.2.2]octan-3-one (0.6 g, 4.8 mmol), iodo benzene (1.16 g, 5.76 mmol), Cs$_2$CO$_3$ (2.36 g, 7.20 mmol), xantphos (0.22 g, 0.38 mmol) and 1,4-dioxane (30 ml) was charged in a sealed tube and degassed with argon gas for 15 min. Tetrakis(triphenylphosphine)palladium (0) (0.22 g, 0.19 mmol) was added and degassed for another 15 min and heated at 125° C. for 3 h. The reaction mixture was filtered and concentrated under reduced pressure to afford the crude compound. This was purified by column chromatography over neutral alumina using 0.5% MeOH in CHCl$_3$ as eluent to afford 600 mg (62%) of 2-phenyl-2-aza-bicyclo[2.2.2]octan-3-one as pale yellow solid.

Step C: Preparation of cis-4-(Phenylamino)cyclohexanecarboxylic acid hydrochloride. A solution of 2-phenyl-2-aza-bicyclo[2.2.2]octan-3-one (0.60 g, 2.97 mmol) and 2N HCl (15 ml) was heated at reflux for 17 h. After completion of the reaction, the solvent was removed under reduced pressure and dried to afford 600 mg of cis-4-(phenylamino)cyclohexanecarboxylic acid hydrochloride (76.5%) as off-white solid which was used for the next step.

Step D: Preparation of cis-Methyl 4-(phenylamino)cyclohexanecarboxylate. Thionyl chloride (0.65 g, 5.47 mmol) was added to a stirred solution of cis-4-(phenylamino)cyclohexanecarboxylic acid hydrochloride (600 mg, 2.74 mmol) in MeOH (10 ml) at room temperature and heated at reflux for 5 h. The reaction mixture was concentrated under reduced pressure. The crude product was basified with saturated sodium bicarbonate solution and extracted with DCM (2×25 ml). The combined organic layer was washed with brine, dried over anhydrous sodium sulfate, filtered and concentrated under reduced pressure to afford the crude compound which was purified by column chromatography over neutral alumina by eluting in 10% ethyl acetate in petroleum ether to afford 500 mg of cis-methyl 4-(phenylamino)cyclohexanecarboxylate (78%) as colorless oily liquid.

Step E: Preparation of cis-4-(Phenylamino)cyclohexanecarboxamide. cis-Methyl 4-(phenylamino)cyclohexanecarboxylate (0.50 g, 2.14 mmol) was dissolved in methanolic ammonia (15 ml) in a pressure bomb and heated at 100° C. for three days. The reaction mixture was cooled to room temperature and concentrated under reduced pressure to afford the crude compound which was washed with n-pentane and dried in vacuo to afford 300 mg (63%) of cis-4-(phenylamino) cyclohexanecarboxamide as white solid.

Preparation of Example 36. Example 36 was synthesized according to Method B starting from the above described cis-4-(phenylamino)cyclohexanecarboxamide (150 mg, 0.91 mmol), Cs$_2$CO$_3$ (0.34 mg, 1.36 mmol), 2-chloro-4-(4-fluoro-2-methoxyphenyl)pyridine (0.20 g, 1.09 mmol), xantphos (32 mg, 50 mol) and Tetrakis(triphenylphosphine)palladium (0) (32 mg, 25 μmol) in dry 1,4-dioxane (10 ml) at 120-125° C. for 3 h in a sealed tube, and purified after usual workup by column chromatography over neutral alumina using ethyl acetate (40-50%) in petroleum ether to afford the product in a yield of 34.6%, followed by conversation to the HCl-salt by dissolving the above obtained compound (100 mg, 0.24 mmol) in DCM and addition of 2.2 eq. of ethereal HCl (0.52 ml, 0.52 mmol, 1 M) at 0° C. for 30 min to obtain the HCl-salt in a yield of 68.1%. $^1$H-NMR (HCl-salt, 400 MHz, DMSO-d$_6$): δ=8.36 (d, 1H), 8.20 (s, 1H), 7.53-7.37 (m, 7H), 7.17-7.12 (m, 1H), 7.00-6.94 (m, 1H), 3.86 (s, 3H), 3.57-3.50 (m, 1H), 2.83-2.77 (m, 1H), 2.18-2.08 (m, 2H), 1.95-1.85 (m, 2H), 1.83-1.75 (m, 2H), 1.73-1.64 (m, 2H), HPLC (λ=214 nm, [A]): rt 11.8 min (100%), mp: 170° C.

Example 37

(1R,3S)-3-(Benzylamino)-N-(4-(4-fluoro-2-methoxyphenyl)pyridin-2-yl)cyclopentanecarboxamide Step A: Preparation of (1R,3S)-Methyl 3-aminocyclopentanecarboxylate. (1R,3S)-Methyl 3-aminocyclopentanecarboxylate was prepared as described above.

Step B: Preparation of (1R,3S)-Methyl 3-(benzylamino) cyclopentanecarboxylate. Potassium carbonate (462 mg, 3.30 mmol) was added to a solution of (1R,3S)-methyl 3-aminocyclopentanecarboxylate (400 mg, 2.22 mmol) in MeOH (10 ml) and stirred for 1 h. Benzyl bromide (0.2 ml, 1.8 mmol) was added to the reaction mixture and stirred for 15 h at 60-65° C. The reaction mixture was concentrated and the resulting residue was partitioned between water and CHCl$_3$. The organic layer was separated and washed with water, brine solution, dried over anhydrous sodium sulfate, filtered and concentrated to afford the crude product. Purification by column chromatography over neutral alumina using 2% MeOH in CHCl$_3$ as eluent afforded 180 mg of (1R,3S)-methyl 3-(benzylamino)cyclopentanecarboxylate with a purity of 75% which was proceeded for the next step.

Step C: Preparation of (1R,3S)-3-(Benzylamino)cyclopentanecarboxamide. Ammonia gas was passed into a solution of (1R,3S)-methyl 3-(benzylamino)cyclopentanecarboxylate (250 mg, 1.14 mmol) in MeOH (5 ml) at −78° C. in a steel bomb. The reaction mixture was slowly warmed to room temperature, heated further to 100° C. and stirred for 24 h. The reaction mixture was concentrated and dried under vacuum to afford 250 mg of (1R,3S)-3-(benzylamino)cyclopentanecarboxamide with 50% purity as brown liquid which was proceeded as crude compound for the next step.

Preparation of Example 37. Example 37 was synthesized according to Method B starting from the above described (1R,3S)-3-(benzylamino)cyclopentanecarboxamide (250 mg, 1.15 mmol, 50% pure), 2-chloro-4-(4-fluoro-2-methoxyphenyl)pyridine (163 mg, 0.69 mmol), Cs$_2$CO$_3$ (560 mg, 1.72 mmol), xantphos (53 mg, 91 μmol) and Tetrakis(triphenylphosphine)palladium (0) (53 mg, 45 μmol) in 1,4-dioxane (5 ml) at 120-125° C. for 3 h in a sealed tube, and purified after usual workup by column chromatography over neutral alumina using MeOH (2%) in CHCl$_3$, further purified by preparative TLC using MeOH (5%) in CHCl$_3$ to afford the product in a yield of 59.0%, followed by conversation to the HCl-salt by dissolving the above obtained compound (75.0 mg, 0.17 mmol) in acetone (3 ml) and addition of 1.2 eq. of ethereal HCl (0.21 ml, 0.21 mmol, 1 M) at 0° C. for 30 min, purified by evaporating acetone at room temperature, adding water and lyophilizing to afford the product in a yield of 79.8% as an off white solid. $^1$H-NMR (HCl-salt, 400 MHz, DMSO-d$_6$): δ=10.78-10.74 (m, 1H), 9.22-9.10 (m, 1H), 8.34-8.31 (m, 1H), 8.19 (d, 1H), 7.58-7.53 (m, 2H), 7.48-7.43 (m, 3H), 7.42-7.36 (m, 1H), 7.26-7.23 (m, 1H), 7.10 (dt, 1H), 6.95-6.89 (m, 1H), 4.19-4.14 (m, 1H), 3.82 (s, 3H), 3.66-3.52 (m, 1H), 3.28-3.20 (m, 1H), 3.12-3.02 (m, 1H), 2.38-2.22 (m, 1H), 2.20-2.10 (m, 1H), 2.08-1.90 (m, 2H), 1.90-1.70 (m, 1H), HPLC ($\lambda$=214 nm, [A]): rt 11.4 min (100%).

Example 38 cis-4-(Benzylamino)-N-(4-(4-fluoro-2-methoxyphenyl)pyridin-2-yl)cyclo-hexanecarboxamide Step A: Preparation of 2-Azabicyclo[2.2.2]octan-3-one. 2-Azabicyclo[2.2.2]octan-3-one was prepared as described above.

Step B: Preparation of 2-Benzyl-2-aza-bicyclo[2.2.2]octan-3-one. Compound 2-azabicyclo[2.2.2]octan-3-one (1.1 g, 8.8 mmol) in THF (10 ml) was added to a stirred suspension of sodium hydride (0.42 g, 10.6 mmol, 60%) in THF (10 ml) at 0° C. and stirred for 15 min. Benzyl bromide (1.05 ml, 8.80 mmol) was added to the reaction mixture at 0° C. and stirred for 4 h at room temperature. The reaction mixture was quenched with saturated ammonium chloride and extracted with ethyl acetate. The combined organic layer was washed with water, brine, dried over anhydrous sodium sulfate, filtered and concentrated under reduced pressure to afford the crude compound. The crude compound was triturated with n-pentane to afford 900 mg (47.6%) of 2-benzyl-2-aza-bicyclo[2.2.2]octan-3-one as solid.

Step C: Preparation of cis-4-(Benzylamino)cyclohexanecarboxylic acid. A solution of 2-benzyl-2-aza-bicyclo[2.2.2]octan-3-one (0.9 g, 4.2 mmol) in 2N HCl (15 ml) was heated at reflux for 18 h. The reaction mixture was allowed to warm up to room temperature and the aqueous layer was washed with ethyl acetate. The aqueous layer was concentrated under reduced pressure to afford 550 mg of cis-4-(benzylamino)cyclohexanecarboxylic acid (56.7%) as solid.

Step D: Preparation of cis-Methyl 4-(benzylamino)cyclohexanecarboxylate. Thionyl chloride was added to a solution of compound cis-4-(benzylamino)cyclohexanecarboxylic acid (0.5 g, 2.1 mmol) in MeOH (7 ml) at 0° C. and the reaction mixture was heated at reflux for 18 h. Then volatiles were removed in vacuo and the reaction mixture was basified using saturated sodium bicarbonate. The aqueous layer was extracted with ethyl acetate, water and brine solution. The organic layer was dried over anhydrous sodium sulfate, filtered and concentrated under reduced pressure to afford 350 mg of cis-methyl 4-(benzylamino)cyclohexanecarboxylate (66%) as brown color solid.

Step E: Preparation of tert-Butyl-cis-4-(methoxycarbonyl) cyclohexylbenzylcarbamate. Boc-anhydride (0.2 ml, 0.9 mmol) was added to a stirred solution of cis-methyl 4-(benzylamino)cyclohexanecarboxylate (0.2 g, 0.8 mmol) in DCM (5 ml) and triethylamine (0.16 ml, 1.21 mmol) at 0° C. and stirred for 18 h. The reaction mixture was diluted with DCM and washed with water, brine solution, dried over anhydrous sodium sulfate, filtered and concentrated under reduced pressure to afford 250 mg of tert-butyl-cis-4-(methoxycarbonyl) cyclohexylbenzylcarbamate (89.3%) as a brown color liquid.

Step F: Preparation of tert-Butyl benzyl-cis-4-carbamoylcyclohexylcarbamate. tert-Butyl-cis-4-(methoxycarbonyl) cyclohexylbenzylcarbamate (0.25 g, 0.72 mmol) was dissolved in methanolic ammonia (15 ml) in a pressure bomb and heated at 100° C. for three days. The reaction mixture was cooled to room temperature and concentrated under reduced pressure to afford 200 mg of tert-butyl benzyl-cis-4-carbamoylcyclohexylcarbamate as crude compound. The crude compound (LC-MS shows 30% amide) was directly taken for next step.

Step G: The Boc-protected precursor of Example 38 tert-butyl cis-4-(4-(4-fluoro-2-methoxyphenyl)pyridin-2-ylcarbamoyl)cyclohexylbenzylcarbamate was synthesized according to Method B starting from the above described tert-butyl benzyl-cis-4-carbamoylcyclohexylcarbamate (200 mg, 0.18 mmol), 2-chloro-4-(4-fluoro-2-methoxyphenyl)pyridine (38.0 mg, 0.16 mmol), $Cs_2CO_3$ (88.0 mg, 0.27 mmol), xantphos (6.0 mg, 10 µmol) and Tetrakis(triphenylphosphine)palladium (0) (4 mg, 3 µmol) in 1,4-dioxane (3 ml) at 125° C. for 4 h in a sealed tube and was purified after usual workup by preparative HPLC (Gemini C-18 (50×30 mm, 10µ), Mobile phase: MeOH/water/HCOOH:70/30/0.01, flow rate: 40 ml min$^{-1}$) to give tert-butyl cis-4-(4-(4-fluoro-2-methoxyphenyl)pyridin-2-ylcarbamoyl)cyclohexylbenzylcarbamate in a yield of 4.6% as a gummy solid.

Preparation of Example 38. Example 38 was synthesized according to Method C starting from the above described tert-butyl cis-4-(4-(4-fluoro-2-methoxyphenyl)pyridin-2-ylcarbamoyl)cyclohexylbenzylcarbamate by means of TFA (0.2 ml) in DCM (5 ml) at room temperature for 1 h, triturated with n-pentane to give the compound as a pale brown solid, followed by conversation to the HCl-salt by dissolving the above obtained compound (20 mg, 46 µmol) in acetone (3 ml) and addition of 1.2 eq. of ethereal HCl (0.05 ml, 0.05 mmol, 1 M) to obtain the HCl-salt in a yield of 92.2% as an off-white solid. Purification was performed by evaporating acetone at room temperature, adding water and lyophilizing to afford the product in a yield of 92% as an off white solid. $^1$H-NMR (HCl-salt, 400 MHz, DMSO-d$_6$): $\delta$=10.75 (s, 1), 9.17 (s, br., 1H), 8.98 (s, br., 1H), 8.32 (t, 1H), 8.18 (d, 1H), 7.57 (t, 2H), 7.45-7.38 (m, 4H), 7.26 (s, 1H), 7.10 (d, 1H), 6.91-6.89 (m, 1H), 3.82 (s, 3H), 3.07 (d, 1H), 2.22-2.03 (m, 1H), 1.98-1.76 (m, 4H), 1.39-1.73 (m, 2H), 1.51-1.33 (m, 2H), 1.23 (s, 2H), HPLC ($\lambda$=214 nm. [A]): rt 11.5 min (97.8%).

Example 39

(1R,3S)—N-(4-(4-Fluoro-2-methoxyphenyl)pyridin-2-yl)-3-(phenylamino)-cyclopentanecarboxamide Step A: Preparation of (1R,3S)-Methyl 3-aminocyclopentanecarboxylate. (1R,3S)-Methyl 3-aminocyclopentanecarboxylate was prepared as described above.

Step B: Preparation of tert-Butyl (1S,3R)-3-(methoxycarbonyl)cyclopentylcarbamate. Boc-anhydride (2.90 ml, 13.1 mmol) was added to a solution of (1R,3S)-methyl 3-aminocyclopentanecarboxylate (1.70 g, 11.9 mmol) and potassium carbonate (3.29 g, 23.8 mmol) in THF (10 ml), water (20 ml) and stirred for 24 h. The reaction mixture was extracted with DCM (2×50 ml). The combined organic layer was washed with water (20 ml), brine solution (20 ml), dried over anhydrous sodium sulfate, filtered and concentrated under vacuo to afford 2.5 g (87%) of tert-butyl (1S,3R)-3-(methoxycarbonyl)cyclopentylcarbamate as a colorless liquid.

Step C: Preparation of tert-Butyl (1S,3R)-3-carbamoylcyclopentylcarbamate. Ammonia gas was passed into a solution of tert-butyl (1S,3R)-3-(methoxycarbonyl)cyclopentylcarbamate (2.0 g, 8.2 mmol) in MeOH (20 ml) at −78° C. in a steal bomb. The reaction mixture was slowly warmed to room temperature, heated to 80° C. and stirred further for 48 h. The reaction mixture was cooled to room temperature and concentrated to afford 1.6 g (85.5%) of tert-butyl (1S,3R)-3-carbamoylcyclopentylcarbamate as brownish solid.

Step D: Preparation of tert-Butyl (1S,3R)-3-(4-(4-fluoro-2-methoxyphenyl)pyridin-2-ylcarbamoyl)cyclopentylcarbamate. tert-Butyl (1S,3R)-3-(4-(4-fluoro-2-methoxyphenyl)pyridin-2-ylcarbamoyl)cyclopentylcarbamate was prepared according to Method B using tert-butyl (1S,3R)-3-carbamoylcyclopentylcarbamate (750 mg, 3.28 mmol), 2-chloro-4-(4-fluoro-2-methoxyphenyl)pyridine (930 mg, 3.94 mmol), Cs$_2$CO$_3$ (1.63 g, 4.92 mmol), xantphos (173 mg, 0.29 mmol), Tetrakis(triphenylphosphine)palladium (0) (150 mg, 0.13 mmol) and 1,4-dioxane (10 ml) brought to reaction at 120° C. for 4 h in a sealed tube.

Step E: Preparation of (1R,3S)-3-Amino-N-(4-(4-fluoro-2-methoxyphenyl)pyridin-2-yl)cyclopentanecarboxamide. (1R,3S)-3-Amino-N-(4-(4-fluoro-2-methoxyphenyl)pyridin-2-yl)cyclopentanecarboxamide was prepared according to Method C using tert-Butyl (1S,3R)-3-(4-(4-fluoro-2-methoxyphenyl)pyridin-2-ylcarbamoyl)cyclopentylcarbamate (1.00 g, 2.33 mmol), TFA (2 ml) in DCM (6 ml) starting at 0° C. which was allowed to warm up to room temperature and stirred for 2 h.

Preparation of Example 39. Phenyl boronic acid (900 mg, 4.10 mmol), copper acetate (746 mg, 4.10 mmol) and pyridine (0.40 ml, 4.10 mmol) were added to a solution of tert-butyl (1S,3R)-3-(4-(4-fluoro-2-methoxyphenyl)pyridin-2-ylcarbamoyl)cyclopentylcarbamate (600 mg, 2.73 mmol) in DCM (10 ml) at room temperature. The reaction mixture stirred for 24 h at the same temperature. The reaction mixture was filtered, the filtrate was diluted with DCM (50 ml), then the organic layers were washed with water (25 ml), brain solution (25 ml). The combined organic layers were dried over sodium sulfate, filtered and concentrated. The crude product was purified by column chromatography using 25% ethyl acetate in petroleum ether to afford 200 mg (18%) of Example 39 in a yield of 57% as a brownish solid, followed by the conversation to the HCl-salt by dissolving the above obtained compound (200.0 mg, 0.493 mmol) in acetone (5 ml) and addition of 2.2 eq. of ethereal HCl (1000 µl, 1.084 mmol, 1 M) at 0° C. for 30 min, purified by evaporating acetone at room temperature, adding water and lyophilizing to afford the product in a yield of 74% as an off white solid. $^1$H-NMR (HCl-salt, 400 MHz, DMSO-d$_6$): δ=10.99 (s, 1H), 8.92 (s, 1H), 8.72 (s, 1H), 7.98 (t, 1H), 7.44-7.16 (m, 5H), 7.14 (d, 1H), 6.94 (t, 1H), 3.94-3.86 (m, 1H), 3.91 (s, 3H), 3.10-3.06 (m, 1H), 2.29-2.08 (m, 2H), 1.96-1.81 (m, 5H), HPLC (λ=214 nm, [A]): rt 13.3 min (100%), mp: starting at 180° C. and completely melts at 200° C.

Example 40

(1R,3S)-3-Acetamido-N-(4-(4-fluoro-2-methoxyphenyl)pyridin-2-yl)cyclohexanecarboxamide Step A: Preparation of cis-3-Aminocyclohexanecarboxylic acid. A 7% (w/v) stock solution of hydrazoic acid in CHCl$_3$ (196 ml, 0.32 mol, the stock solution was prepared by adding 400 g of NaN$_3$ into 400 ml of water to CHCl$_3$ (2 l)). Sulfuric acid (167 ml) was added under stirring at 0° C. slowly. The upper CHCl$_3$ layer was decanted, dried over anhydrous sodium sulfate, filtrated and kept in the refrigerator. Titration analysis was done before usage. The solution was added dropwise over a period of 8 h to a solution of cis-cyclohexane-1,3-dicarboxylic acid (50.0 g, 0.29 mol) in a mixture of sulfuric acid (150 ml) and CHCl$_3$ (500 ml) at 35° C. After the completion of addition, the reaction mixture was stirred at 40° C. for 10 h and further stirred at 50° C. for 3 h. The reaction mixture was cooled to room temperature and the acid layer was separated. The acid layer was basified with barium hydroxide to pH~9 and the suspension was filtered. The filtrate was neutralized with diluted sulfuric acid and the suspension was filtered again. The filtrate was concentrated under vacuo to get the crude compound which was washed with MeOH (30 ml) to get 39.0 g (93.8%) of cis-3-aminocyclohexanecarboxylic acid as solid. [TLC system: 15% MeOH in CHCl$_3$, R$_f$ 0.1].

Step B: Preparation of tert-Butyl-cis-3-aminocyclohexanecarboxylic acid. Boc-anhydride (353 ml, 1.54 mol) was added to a solution of cis-3-aminocyclohexanecarboxylic acid (200 g, 1.40 mol), DIPEA (974 ml, 5.59 mol) in a mixture of dioxane (1 l) and water (1 l) at 0° C. The reaction mixture was warmed up to room temperature and stirred for 4 h. The reaction mixture was again cooled to 0° C., acidified to pH 2 with 2N HCl, extracted with DCM (3×11) and the combined organic layers were washed with water (2×1), brine (2×11), dried over anhydrous sodium sulfate and filtered. Concentration under vacuo gave the crude compound which was washed with petroleum ether (300 ml) to get 202 g (59.4%) of tert-Butyl-cis-3-aminocyclohexanecarboxylic acid as solid. [TLC system: 20% MeOH in CHCl$_3$, R$_f$ 0.1].

Step C: Preparation of 1R,3S-Methyl 3-aminocyclohexanecarboxylate. 1R,3S-Methyl 3-aminocyclohexanecarboxylate was prepared by addition of R-(+)-1-Phenylethylamine to a solution of tert-butyl-cis-3-aminocyclohexanecarboxylic acid in ethyl acetate at reflux and stirring the mixture for 1 h. The reaction mixture was filtered at reflux and washed with hot ethyl acetate. The solid was taken in ethyl acetate and washed with 0.1 N HCl, water and brine. The ethyl acetate layer was concentrated under vacuo to get the desired 1R,3S-Methyl 3-aminocyclohexanecarboxylate.

Step D: Preparation of tert-Butyl (1S,3R)-3-carbamoylcyclohexylcarbamate. tert-Butyl (1S,3R)-3-carbamoylcyclohexylcarbamate was prepared the reaction of carbonyldiimidazole and 1R,3S-Methyl 3-aminocyclohexanecarboxylate in dry DMF.

Step E: Preparation of tert-Butyl (1S,3R)-3-(4-(4-fluoro-2-methoxyphenyl)pyridin-2-ylcarbamoyl)cyclohexylcarbamate. tert-Butyl (1S,3R)-3-(4-(4-fluoro-2-methoxyphenyl)pyridin-2-ylcarbamoyl)cyclohexylcarbamate was prepared according to Method B in a yield of 61.2%.

Step F: Preparation of (1R,3S)-3-Amino-N-(4-(4-fluoro-2-methoxyphenyl)pyridin-2-yl)cyclohexanecarboxamide. (1R,3S)-3-Amino-N-(4-(4-fluoro-2-methoxyphenyl)pyridin-2-yl)cyclohexanecarboxamide was prepared according to Method C in a yield of 96.3%.

Preparation of Example 40. Example 40 was synthesized by means of acetic anhydride starting from the above described (1R,3S)-3-amino-N-(4-(4-fluoro-2-methoxyphenyl)pyridin-2-yl)cyclohexanecarboxamide in a yield of 74.9%. $^1$H-NMR (400 MHz, CDCl$_3$): δ=8.32-8.25 (m, 2H), 8.14-8.07 (m, 1H), 7.33 (t, 1H), 7.22-7.20 (m, 1H), 6.76-6.69 (m, 2H), 5.45 (d, 1), 3.89-3.83 (m, 4H), 2.43-2.40 (m, 1H), 2.26-2.23 (m, 1H), 1.97-1.89 (m, 6H), 1.51-1.37 (m, 3H), 1.16-1.12 (m, 1H), HPLC (λ=214 nm, [A]): rt 11.1 min (100%), Chiral HPLC: 99.18%, mp: 234-236° C.

Example 41

(1S,3R)-3-Acetamido-N-(4-(4-fluoro-2-methoxyphenyl)pyridin-2-yl)cyclopentanecarboxamide Step A: Preparation of 1-Azabicyclo[2.2.1]heptan-3-one. (1S)-(+) Azabicyclo[2,2,1]hept-5-ene-3-one (1.00 g, 11.9 mmol) was hydrogenated over Palladium on carbon (50 mg, 10 wt. %) in a Parr Hydrogenation Apparatus at 50 psi for 5 h. The reaction mixture was filtered through a pad of celite and washed with ethyl acetate. The combined filtrate and washings was concentrated in vacuo to afford 1.00 g (95.75%) of 1-azabicyclo[2.2.1]heptan-3-one as white solid.

Step B: Preparation of (1S,3R)-3-Aminocyclopentanecarboxylic acid hydrochloride. A solution of 1-azabicyclo[2.2.1]heptan-3-one (1.00 g, 9.01 mmol) in 3N HCl (20 ml) was refluxed for 4 h. The volatiles were evaporated in vacuo, co-distilled with toluene and dried under reduced pressure to afford 1.30 g (87.2%) of (1S,3R)-3-aminocyclopentanecarboxylic acid hydrochloride as white solid.

Step C: Preparation of (1S,3R)-Cyclopentanecarboxylic acid, 3-[[(1,1-dimethylethoxy)carbonyl]amino]. Aqueous potassium carbonate (2.20 g, 15.7 mmol) in water (20 ml) was added to a suspension of (1S,3R)-3-aminocyclopentanecarboxylic acid hydrochloride (1.30 g, 7.85 mmol) in THF (20 ml) at 0° C., stirred for 15 min and Boc-anhydride (2.70 ml, 11.8 mmol) was added. The reaction mixture was warmed to room temperature and stirred for 20 h. The reaction mixture was acidified with 10% acetic acid to a pH of 4.0-5.0 and extracted with ethyl acetate (2×30 ml). The combined organic layer was washed successively with water, brine, dried over anhydrous sodium sulfate and concentrated to afford 1.30 g (72.2%) of (1S,3R)-cyclopentanecarboxylic acid, 3-[[(1,1-dimethylethoxy)carbonyl]amino] as pale yellow liquid.

Step D: Preparation of Carbamic acid, [(1S,3R)-3-(aminocarbonyl)cyclopentyl]-, 1,1-dimethylethyl ester. N,N'-carbonyl diimidazole (2.76 g, 17.0 mmol) was added to a solution of (1S,3R)-cyclopentanecarboxylic acid, 3-[[(1,1-dimethylethoxy)carbonyl]amino](1.32 g, 5.73 mmol) in THF (20 ml) and heated at 60° C. for 1 h. The reaction mixture was cooled to 0° C. and ammonium acetate (2.62 g, 34.0 mmol) was added. The reaction mixture was warmed to room temperature and stirred for 4 h. Water was added and extracted with ethyl acetate (2×30 ml). The combined organic layer was washed successively with water, brine, dried over anhydrous sodium sulfate and concentrated in vacuo to afford 1.3 g of crude. The crude compound was suspended in diethyl ether, stirred for 15 min, filtered, washed with diethyl ether and the solid was dried under reduced pressure to afford 300 mg (23.2%) of carbamic acid, [(1S,3R)-3-(aminocarbonyl)cyclopentyl]-, 1,1-dimethylethyl ester as white solid.

Step E: Preparation of tert-Butyl (1R,3S)-3-(6-(4-fluoro-2-methoxyphenyl)pyrimidin-4-ylcarbamoyl)cyclopentylcarbamate. tert-Butyl (1R,3S)-3-(6-(4-fluoro-2-methoxyphenyl)pyrimidin-4-ylcarbamoyl)cyclopentylcarbamate was synthesized according to Method B starting from the above described carbamic acid, [(1S,3R)-3-(aminocarbonyl)cyclopentyl]-, 1,1-dimethylethyl ester (150 mg, 0.66 mmol), 2-chloro-4-(4-fluoro-2-methoxyphenyl)pyridine (155 mg, 0.66 mmol), $Cs_2CO_3$ (321 mg, 0.98 mmol), xantphos (19.0 mg, 328 μmol) and tetrakis(triphenylphosphine)palladium (0) (29 mg, 26 μmol) in 1,4-dioxane (5 ml) at 110° C. for 20 h in a sealed tube, and was purified after usual workup by column chromatography over neutral alumina using 0-2% MeOH in $CHCl_3$ and triturating with ether to afford the product in a yield of (70.9%) as pale yellow solid.

Step F: Preparation of (1S,3R)-3-Amino-N-(6-(4-fluoro-2-methoxyphenyl)pyrimidin-4-yl)cyclopentanecarboxamide. (1S,3R)-3-Amino-N-(6-(4-fluoro-2-methoxyphenyl)pyrimidin-4-yl)cyclopentanecarboxamide was prepared according to Method C starting from the above described tert-butyl (1R,3S)-3-(6-(4-fluoro-2-methoxyphenyl)pyrimidin-4-ylcarbamoyl)cyclopentylcarbamate (200 mg, 0.46 mmol) in a yield of (71.8%) as yellow solid.

Preparation of Example 41. Acetic anhydride (0.035 ml, 0.304 mmol) was added to a solution of (1S,3R)-3-Amino-N-(6-(4-fluoro-2-methoxyphenyl)pyrimidin-4-yl)cyclopentanecarboxamide (100 mg, 0.30 mmol) in DCM (5 ml) and catalytic amount of AcOH (0.1 ml) at 0° C. The reaction mixture was warmed to room temperature and stirred for 2.5 h. Water was added to the reaction mixture and extracted with DCM (3×25 ml). The combined organic layer was washed with water, brine and dried over anhydrous sodium sulfate and concentrated in vacuo to afford 90 mg (80.3%) of (1S,3R)-3-acetamido-N-(4-(4-fluoro-2-methoxyphenyl)pyridin-2-yl)cyclopentanecarboxamide as an off white solid. $^1$H-NMR (400 MHz, DMSO-$d_6$): δ=10.52 (s, 1H), 8.31 (s, 1H), 8.21 (s, 1H), 7.92 (t, 1H), 7.39-7.36 (m, 1H), 7.19-7.02 (m, 2H), 6.92 (q, 1H), 4.02 (t, 1H), 3.90 (s, 3H), 2.98 (t, 1H), 2.17-2.10 (m, 1H), 1.91-1.62 (m, 6H), 1.59-1.42 (m, 2H), HPLC (λ=214 nm, [A]): rt 10.4 min (100%), Chiral HPLC: 98.52%, mp: 125-129° C.

Biological Examples, Evaluation, Determination of $IC_{50}$-Values of Kinase-Inhibitors Biological Example 1

In Vitro Kinase Inhibition Assays

In vitro kinase assay analysis may be performed using standard techniques described in the art. These techniques are also used by commercial services providers in order to offer in vitro kinase activity assay services, e.g. the assays offered by Millipore Inc. (worldwide website www(dot)millipore.com), ProQinase GmbH (worldwide website www(dot)proqinase.de) and others.

The following protocol describes one possible way to conduct the experiment.

1. Test Compounds

Compounds were be used as $1 \times 10^{-02}$ M stock solutions in 100% DMSO, 100% each in column 2 of three 96-well V-shaped microtiterplates. (in the following, said plates are referred to as "master plates").

Subsequently, the $1 \times 10^{-02}$ M stock solutions in column 2 of the master plates were subjected to a serial, semi-logarithmic dilution using 100% DMSO as a solvent, resulting in 10 different concentrations, the dilution endpoint being $3 \times 10^{-07}$ M/100% DMSO in column 12. Column 1 and 7 were filled with 100% DMSO as controls. Subsequently, 2×5 μl of each well of the serial diluted copy plates were aliquoted in 2 identical sets of "compound dilution plates", using a 96-channel pipettor.

On the day of the kinase inhibition assay, 451 μl $H_2O$ were added to each well of a set of compound dilution plates. To minimize precipitation, the $H_2O$ was added to the plates only a few minutes before the transfer of the compound solutions into the assay plates. The plates were shaken thoroughly, resulting in "compound dilution plates/10%/DMSO" with a concentration of $1 \times 10^{-03}$ M/10% DMSO to $3 \times 10^{-08}$ M/10% DMSO in semilog steps. These plates were used for the transfer of 5 μl compound solution into the "assay plates". The compound dilution plates were discarded at the end of the working day. For the assays (see below), 5 μl solution from each well of the compound dilution plates were transferred into the assay plates. The final volume of the assay was 50 μl. All compounds were tested at 10 final assay concentrations in the range from $1 \times 10^{-04}$ M to $3 \times 10^{-09}$ M. The final DMSO concentration in the reaction mixtures was 1% in all cases.

2. Recombinant Protein Kinases

For the determination of inhibitory profiles, the following 5 protein kinases were used: CDK2/CycA, CDK4/CycD1, CDK5/p35NCK, CDK6/CycD1 and CDK9/CycT. Said protein kinases were expressed in Sf9 insect cells as human recombinant GST-fusion proteins or His-tagged proteins by means of the baculovirus expression system. Kinases were purified by affinity chromatography using either GSH-agarose (Sigma) or Ni-NTH-agarose (Qiagen). The purity of each kinase was determined by SDS-PAGE/silver staining and the identity of each kinase was verified by western blot analysis with kinase specific antibodies or by mass spectroscopy.

3. Protein Kinase Assay

All kinase assays were performed in 96-well FlashPlates™ from Perkin Elmer/NEN (Boston, Mass., USA) in a 50 µl reaction volume. The reaction mixture was pipetted in four steps in the following order:

20 µl of assay buffer (standard buffer)
5 µl of ATP solution (in $H_2O$)
5 µl of test compound (in 10% DMSO)
10 µl of substrate/10 µl of enzyme solution (premixed)

The assay for all enzymes contained 60 mM HEPES-NaOH (pH 7.5), 3 mM $MgCl_2$, 3 mM $MnCl_2$, 3 µM Na-Orthovanadate, 1.2 mM DTT, 50 µg/ml PEG2000, 1 µM [$^{33}P$]-ATP (approx. 5 ×1005 cpm per well).

The following amounts of enzyme and substrate were used per well:

| # | Kinase | Kinase Lot # | Kinase ng/50 µl | Substrate | Substrate ng/50 µl |
|---|---|---|---|---|---|
| 1 | CDK2/CycA | SP005 | 100 | Histone H1 | 250 |
| 1 | CDK4/CycD1 | SP005 | 50 | Rb-CTF (Lot 009) | 500 |
| 3 | CDK5/p35NCK | SP001 | 50 | Rb-CTF (Lot 009) | 1000 |
| 3 | CDK6/CycD1 | SP003 | 400 | Rb-CTF (Lot 009) | 500 |
| 4 | CDK9/CycT | 003 | 100 | Rb-CTF (Lot 009) | 1000 |

Reaction mixtures were incubated at 30° C. for 80 min. The reaction was stopped with 50 µl of 2% (v/v) $H_3PO_4$, plates were aspirated and washed two times with 200 µl $H_2O$ or 200 µl 0.9% (w/v) NaCl. Incorporation of $^{33}P$ was determined with a microplate scintillation counter (Microbeta, Wallac).

All assays were performed with a BeckmanCoulter/Sagian robotic system.

4. Evaluation of Raw Data

The median value of the counts in column 1 (n=8) of each assay plate was defined as "low control". This value reflects unspecific binding of radioactivity to the plate in the absence of a protein kinase but in the presence of the substrate. The median value of the counts in column 7 of each assay plate (n=8) was taken as the "high control", i.e. full activity in the absence of any inhibitor. The difference between high and low control was referred to as 100% activity. As part of the data evaluation, the low control value from a particular plate was subtracted from the high control value as well as from all 80 "compound values" of the corresponding plate. The residual activity (in %) for each well of a particular plate was calculated by using the following formula:

Res. Activity(%)=100×[(cpm of compound−low control)/(high control−low control)]

The residual activities for each concentration and the compound IC50 values were calculated using *Quattro Workflow* V2.0.1.3 (Quattro Research GmbH, Munich, Germany; worldwide website www(dot)quattro-research.com). The model used was "Sigmoidal response (variable slope)" with parameters "top" fixed at 100% and "bottom" at 0%.

Table 1 shows the results of the in vitro kinase inhibition assays for Example compounds 1 to 39.

TABLE 1

List of Examples, Structures and Activities (TNF-alpha, CDK5 and CDK9)

| Exam. | Structure | Formula | Mol.-Weight |
|---|---|---|---|
| 1 | 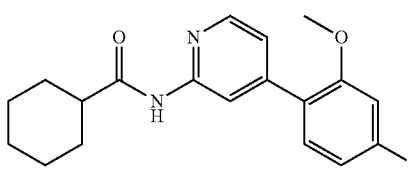 | $C_{19}H_{21}FN_2O_2$ | 328.38 |
| 2 | 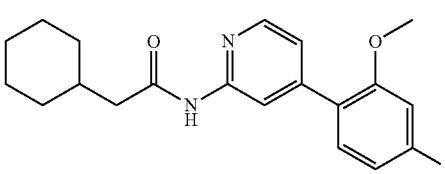 | $C_{20}H_{23}FN_2O_2$ | 342.41 |
| 3 | 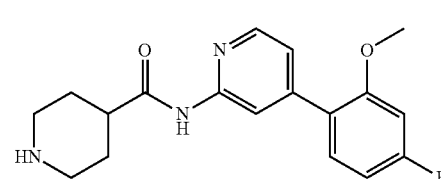 | $C_{18}H_{20}FN_3O_2$ | 329.37 |

TABLE 1-continued

List of Examples, Structures and Activities (TNF-alpha, CDK5 and CDK9)

| # | Structure | Formula | MW |
|---|---|---|---|
| 4 | (structure) | C₁₉H₂₂FN₃O₂ | 343.39 |
| 5 | (structure) | C₁₇H₁₆FN₃O₃ | 329.33 |
| 6 | (structure) | C₂₁H₁₉FN₂O₃ | 366.39 |
| 7 | (structure) | C₂₀H₁₇FN₂O₂ | 336.36 |
| 8 | (structure) | C₁₉H₁₆FN₃O₂ | 337.35 |
| 9 | (structure) | C₁₈H₁₅FN₂O₂S | 342.39 |
| 10 | (structure) | C₂₁H₁₉FN₂O₂ | 350.39 |
| 11 | (structure) | C₂₂H₂₁FN₂O₃ | 380.41 |

TABLE 1-continued

List of Examples, Structures and Activities (TNF-alpha, CDK5 and CDK9)

| | Structure | Formula | MW |
|---|---|---|---|
| 12 | | $C_{20}H_{18}FN_3O_2$ | 351.37 |
| 13 | | $C_{20}H_{18}FN_3O_2$ | 351.37 |
| 14 | | $C_{20}H_{18}FN_3O_3$ | 367.37 |
| 15 | | $C_{20}H_{18}FN_3O_2$ | 351.37 |
| 16 | | $C_{20}H_{18}FN_3O_2$ | 351.37 |
| 17 | | $C_{19}H_{17}FN_2O_2S$ | 356.41 |
| 18 | | $C_{19}H_{17}FN_2O_2S$ | 356.41 |
| 19 | | $C_{19}H_{15}ClFN_3O_2$ | 371.79 |

TABLE 1-continued
List of Examples, Structures and Activities (TNF-alpha, CDK5 and CDK9)
| | | | |
|---|---|---|---|
| 20 | 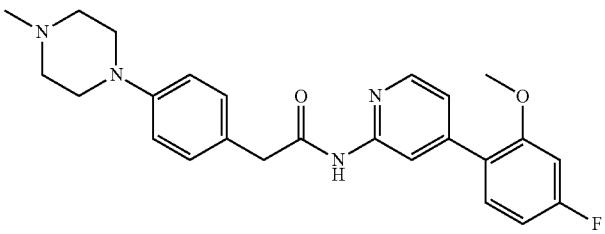 [SMILES: COc1cc(F)ccc1-c1ccnc(NC(=O)Cc2ccc(N3CCN(C)CC3)cc2)c1] | C$_{25}$H$_{27}$FN$_4$O$_2$ | 434.51 |
| 21 | 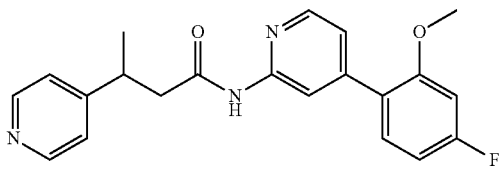 [SMILES: COc1cc(F)ccc1-c1ccnc(NC(=O)CC(C)c2ccncc2)c1] | C$_{21}$H$_{20}$FN$_3$O$_2$ | 365.40 |
| 22 | 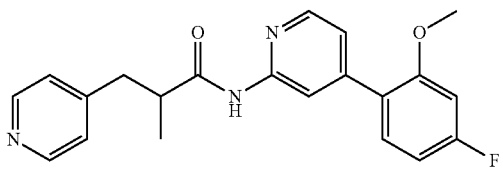 | C$_{21}$H$_{20}$FN$_3$O$_2$ | 365.40 |
| 23 | 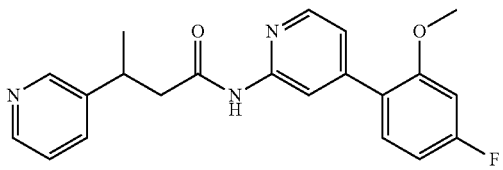 [SMILES: COc1cc(F)ccc1-c1ccnc(NC(=O)CC(C)c2cccnc2)c1] | C$_{21}$H$_{20}$FN$_3$O$_2$ | 365.40 |
| 24 | 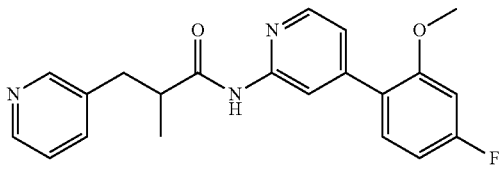 [SMILES: COc1cc(F)ccc1-c1ccnc(NC(=O)C(C)Cc2cccnc2)c1] | C$_{21}$H$_{20}$FN$_3$O$_2$ | 365.40 |
| 25 | 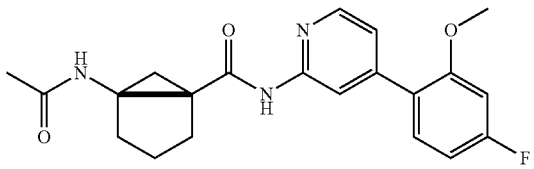 | C$_{21}$H$_{24}$FN$_3$O$_3$ | 385.43 |
| 26 | 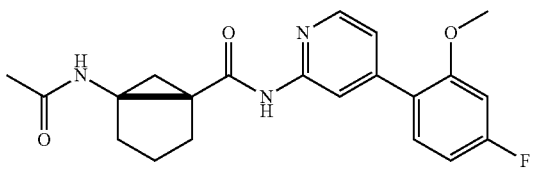 | C$_{21}$H$_{24}$FN$_3$O$_3$ | 385.43 |
| 27 | 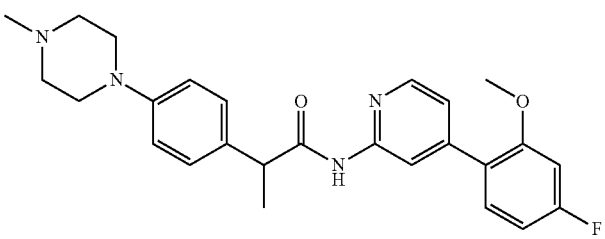 [SMILES: COc1cc(F)ccc1-c1ccnc(NC(=O)C(C)c2ccc(N3CCN(C)CC3)cc2)c1] | C$_{26}$H$_{29}$FN$_4$O$_2$ | 448.53 |

TABLE 1-continued

List of Examples, Structures and Activities (TNF-alpha, CDK5 and CDK9)

| | | | |
|---|---|---|---|
| 28 | | $C_{27}H_{31}FN_4O_2$ | 462.56 |
| 29 | | $C_{27}H_{31}FN_4O_2$ | 462.56 |
| 30 | | $C_{24}H_{25}FN_4O_2$ | 420.48 |
| 31 | | $C_{24}H_{26}FN_5O_2$ | 435.49 |
| 32 | | $C_{24}H_{25}FN_4O_2$ | 420.48 |
| 33 | | $C_{21}H_{24}FN_3O_3$ | 385.43 |
| 34 | | $C_{22}H_{22}FN_3O_3$ | 371.40 |

US 9,067,888 B2
81 82
TABLE 1-continued
List of Examples, Structures and Activities (TNF-alpha, CDK5 and CDK9)
| 35 | 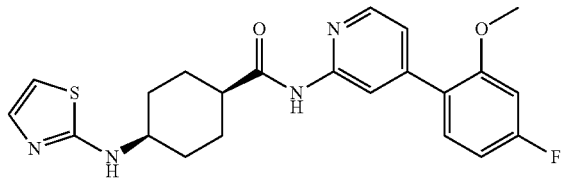 [SMILES: COc1cc(F)ccc1-c1ccnc(NC(=O)[C@H]2CC[C@@H](Nc3nccs3)CC2)c1] | $C_{23}H_{24}FN_4O_2S$ | 426.51 |
| 36 | 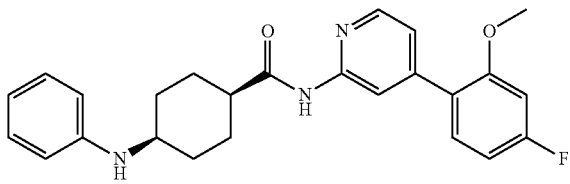 [SMILES: COc1cc(F)ccc1-c1ccnc(NC(=O)[C@H]2CC[C@@H](Nc3ccccc3)CC2)c1] | $C_{25}H_{26}FN_3O_2$ | 419.49 |
| 37 | 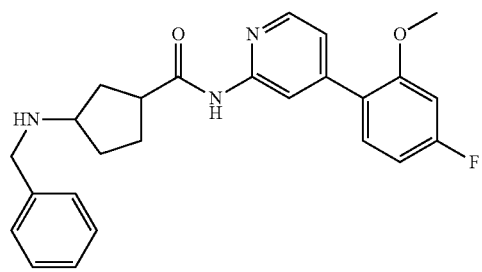 [SMILES: COc1cc(F)ccc1-c1ccnc(NC(=O)C2CCC(NCc3ccccc3)C2)c1] | $C_{25}H_{26}FN_3O_2$ | 419.49 |
| 38 | 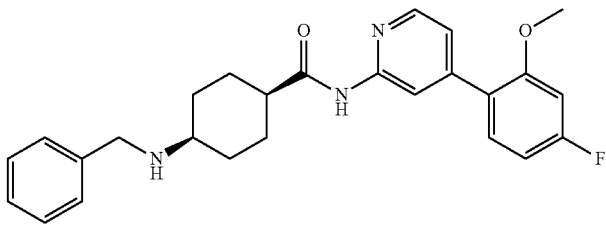 [SMILES: COc1cc(F)ccc1-c1ccnc(NC(=O)[C@H]2CC[C@@H](NCc3ccccc3)CC2)c1] | $C_{26}H_{28}FN_3O_2$ | 433.51 |
| 39 | 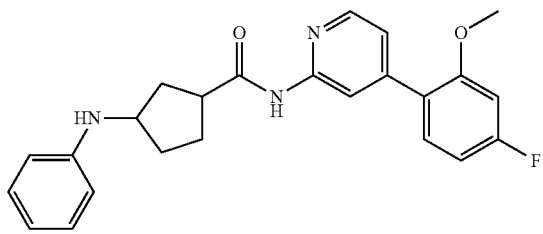 [SMILES: COc1cc(F)ccc1-c1ccnc(NC(=O)C2CCC(Nc3ccccc3)C2)c1] | $C_{24}H_{24}FN_3O_2$ | 405.46 |
| 40 | 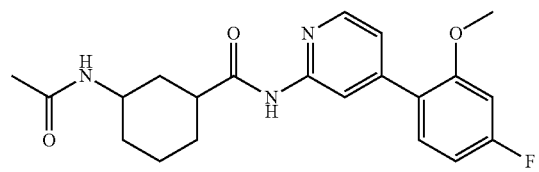 [SMILES: COc1cc(F)ccc1-c1ccnc(NC(=O)C2CCCC(NC(C)=O)C2)c1] | $C_{21}H_{24}FN_3O_3$ | 385.43 |
| 41 | 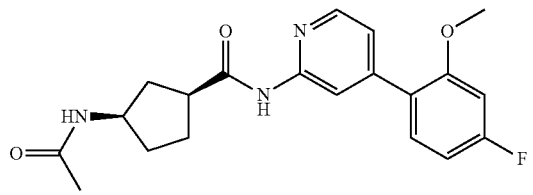 [SMILES: COc1cc(F)ccc1-c1ccnc(NC(=O)[C@H]2CC[C@@H](NC(C)=O)C2)c1] | $C_{20}H_{22}FN_3O_3$ | 371.40 |

TABLE 1-continued

List of Examples, Structures and Activities (TNF-alpha, CDK5 and CDK9)

| Exam. | ESI-MS (M + H⁺) | Efficacy (ratio to DMSO) TNF-alpha induced response | CDK9 100 nM (RA in %) | CDK9 10 nM (RA in %) | CDK9 1 μM (RA in %) |
|---|---|---|---|---|---|
| 1 | 329.1 | 0.23 | 23 | 88 | 106 |
| 2 | 343.3 | 0.49 | 33 | 78 | 77 |
| 3 | 330.4 | 0.05 | 9 | 86 | 118 |
| 4 | 344.2 | 0.05 | 4 | 59 | 107 |
| 5 | 330.3 | 0.04 | 5 | 46 | 39 |
| 6 | 367.1 | 0.07 | 16 | 68 | 27 |
| 7 | 337.2 | 0.08 | 17 | 78 | 47 |
| 8 | 338.2 | 0.04 | 7 | 93 | 34 |
| 9 | 343.0 | 0.04 | 16 | 76 | 42 |
| 10 | 351.3 | 0.10 | 10 | 68 | 56 |
| 11 | 381.4 | 0.07 | 6 | 36 | 6 |
| 12 | 352.5 | 0.83 | 96 | 94 | 94 |
| 13 | 352.3 | 0.04 | 2 | 66 | 17 |
| 14 | 368.2 | 0.04 | 7 | 25 | 10 |
| 15 | 352.2 | 0.83 | 64 | 84 | 80 |
| 16 | 352.2 | 0.04 | 7 | 65 | 28 |
| 17 | 357.1 | 0.88 | 97 | 114 | 79 |
| 18 | 357.1 | 0.07 | 5 | 32 | 102 |
| 19 | 372.1 | 0.06 | 9 | 49 | 99 |
| 20 | 435.5 | 0.08 | 5 | 39 | 26 |
| 21 | 366.4 | 0.82 | 29 | 88 | 106 |
| 22 | 366.3 | 0.98 | 39 | 93 | 106 |
| 23 | 366.3 | 0.89 | 35 | 95 | 117 |
| 24 | 366.3 | 1.04 | 32 | 92 | 128 |
| 25 | 386.3 | 0.92 | 78 | 99 | 100 |
| 26 | 386.3 | 0.03 | 5 | 33 | 63 |
| 27 | 449.4 | 0.08 | 8 | 65 | 36 |
| 28 | 463.5 | 1.21 | 49 | 88 | 92 |
| 29 | 463.5 | 1.05 | 39 | 95 | 94 |
| 30 | 421.4 | 0.03 | 4 | 29 | 56 |
| 31 | 436.4 | 0.04 | 8 | 58 | 36 |
| 32 | 421.4 | 0.04 | 4 | 34 | 72 |
| 33 | 386.5 | 0.03 | 3 | 29 | 43 |
| 34 | 372.3 | 0.07 | 8 | 50 | 81 |
| 35 | 427.3 | 0.02 | 4 | 36 | 36 |
| 36 | 420.4 | 0.26 | 12 | 59 | 73 |
| 37 | 420.4 | 0.02 | 2 | 20 | 35 |
| 38 | 434.4 | 0.02 | 4 | 65 | 102 |
| 39 | 406.5 | 0.05 | 6 | 60 | 61 |
| 40 | 386.2 | 0.46 | 38 | 89 | 114 |
| 41 | 372.4 | 0.03 | 8 | 38 | 93 |

In vitro kinase inhibition results shown in columns 7 to 9 in Table 1 were obtained by employing the KinaseProfiler™ service of Millipore and used to select compounds displaying specificity for CDK9. Specifically, it was intended to distinguish the CDK9-specific compounds from other compounds having significant inhibitory potency also with regard to other CDKs.

Furthermore, these data were used to establish structure activity relationships (SAR) supporting the design of new and even improved structures/compounds with respect to potency and selectivity.

Table 2: Kinase Activity assay IC50 Profiles

IC50 profiles of compound 33 and 34 were determined for cyclin-dependent kinases CDK1/CycB, CDK2/CycA, CDK3/CycE, CDKS/p35NCK, CDK6/CycD3, CDK7/CycH/MAT1, CDK9/CycT GSK3-alpha, GSK3-beta and IRAK1 in enzymatic kinase inhibition assays in vitro. The results are shown in Table 2.

TABLE 2

Selectivity data for Compounds 33 and 34 (IC50)

| IC50s [nM] | CDK1/B | CDK2/A | CDK3/E | CDK5/p35 | CDK6/D3 | CDK7/H/MAT1 | CDK9/T1 | GSK3a | GSK3b | IRAK1 |
|---|---|---|---|---|---|---|---|---|---|---|
| cpd 33 | 94 | 168 | 219 | 1077 | >5000 | >5000 | 3 | 160 | 903 | >5000 |
| cpd 34 | 1877 | 913 | 1449 | 1337 | >5000 | >5000 | 10 | 99 | 857 | >5000 |

IC50 values as obtained in these assays were used for evaluating the specific selectivity and potency of the compounds with respect to CDK9 inhibition.

Results obtained in these assays were used to select compounds displaying specificity for CDK9. Specifically, it was intended to distinguish the CDK9-specific compounds from other compounds having significant inhibitory potency also with regard to other CDKs, i.e. on some or all of CDKs 1, 2, 3, 5, 6, and 7.

Furthermore, these data were used to establish structure activity relationships (SAR) supporting the design of new and even improved structures/compounds with respect to potency and selectivity.

Biological Example 2

In Vitro Kinase Binding Assay

In vitro kinase binding assays may be performed using standard techniques described in the art.

These techniques are also used by commercial services providers in order to offer in vitro kinase binding assay services, e.g. the KINOMEscan™ service offered by Ambit Biosciences Inc. (worldwide website www(dot)ambit-bio.com).

The following protocol describes one possible way to conduct the experiment.

For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 µm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween™ 20, 1 mM DTT) to remove unbound ligand and to reduce non-specific phage binding. Binding reactions were assembled by combining kinases, liganded affinity beads, and test compounds in 1× binding buffer (20% SeaBlock™, 0.17×PBS, 0.05% Tween™ 20, 6 mM DTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween™ 20). The beads were then re-suspended in elution buffer (1×PBS, 0.05% Tween™ 20, 0.5 M non-biotinylated affinity ligand) and incubated at room temperature with shaking for 30 minutes. The kinase concentration in the eluates was measured by qPCR.

Biological Example 3

Inhibition of TNF-Alpha-Induced Cellular Effects

CDK9 has been reported to mediate effects mediated by exposition of cells to TNF-alpha, which results in intracellular signal transduction events and transcriptional response (MacLachlan, T. K. et al., J Cell Biochem. 1998, 71, 467-78, Brasier, A. R., Cell Cycle. 2008, 7, 2661-6).

TNF-alpha responsive cell lines like the human HeLa cell line can be used to study cellular responses to TNF-alpha, e.g. transcriptional regulation of a transfected TNF-alpha responsive reporter gene, and effects of kinase inhibitors on this response.

The following protocol describes one possible way to conduct the experiment.

In order to analyse compound effects on TNF-alpha mediated transcriptional response, a HeLa-derived cell line stably transfected with a TNF-alpha inducible reporter gene was used (Panomics Catalog No. RC0013). The cell line was obtained by co-transfection of a luciferase reporter gene (Panomics P/N LR0051) and pHyg into human cervical epithelial HeLa cells, followed by hygromycin selection. TNFα-induced luciferase activity was used to select clones from the hygromycin-resistant cells. The cell line was maintained and stimulated according to the manufacturer's instructions. Briefly, cells were seeded at $5\times10^5$/well in 1 ml of growth medium in a 12-well plate and incubated in a humidified incubator at 37° C. and 5% CO2 for 24 hours. Medium was replaced with 1 ml of serum free medium and compounds were added up to concentrations of 10 M. After 1 hour of incubation, TNF-alpha was added to achieve a final concentration of 50 ng/ml. The culture dish was further incubated in a humidified incubator at 37° C. and 5% CO2 for 6 hours, medium was removed and 100 µL of lysis buffer were added to each well and the assay for luciferase activity was performed according to assay manufacturer's (Promega P/N E1500) recommendations. For more information about this cell line, go to worldwide website www(dot)panomics.com.

Table 1

Examples

Compound effects on TNF-alpha-induced reporter gene expression is shown in column 6 in Table 1 given below. Indicated is the remaining luciferase activity after incubation in presence of 3 µM of compound as a ratio of the activity of DMSO-treated cells without compound. Specifically, it was intended to distinguish cell permeable compounds from other compounds having significant inhibitory potency with regard to other CDKs, but fail to penetrate cells or are unstable under the conditions of the experiment. Furthermore, these data were used to establish structure activity relationships (SAR) supporting the design of new and even improved structures/compounds with respect to potency and cellular efficacy.

Biological Example 4

Inhibition of Lps-Induced Cytokine Release from THP-1 Cells

It has been recognized that inflammatory mediators such as the cytokines TNFα, IL6 and IL1β can contribute to persistent pain states as well as to inflammatory disorders. After being released from immune cells like macrophages in peripheral and microglia in CNS tissues, these mediators seem to play a pivotal role not only in inflammatory and neuropathic pain but also in inflammatory disorders such as rheumatoid arthritis (Marchand, F. et al., Nat Rev Neurosci 2005, 6, 521-532). Hence inhibition of tumor necrosis factor α (TNFα) represents a relevant target in the treatment of inflammatory disorders as well (Lavagno, L. et al., Eur J Pharmacol 2004, 501, 199-208).

The human THP-1 cell line can be utilized as an in vitro model of cytokine expression as mediated by Lipopolysaccharide (Lps) or Tumor Necrosis Factorα [TNFα]. Monocytic THP-1 cells (ATCC; TIB-202) can be differentiated into macrophage-like cells expressing pro-inflammatory cytokines like TNFα, IL6 and L1β upon induction with Lps or by TNFα (autocrine induction) itself. Therefore, the THP-1 in vitro assay can be used as a powerful screening model to address pharmacological inhibition of cytokine expression (Singh, U. et al., Clin Chem 2005, 51, 2252-2256; Rutault, K. et al., J Biol Chem 2001, 276, 6666-6674).

The following protocol describes one possible way to conduct the experiment.

THP-1 cells are grown in modified RPMI-1640 medium (ATCC, Cat. No. 30-2001) supplemented with 10% FCS and 1% Pen/Strep. For cytokine inhibition assays, cells are seeded at a density of $5 \times 10^5$ cells/ml into 6-well plates in standard growth medium supplemented with 100 ng/ml PMA (Sigma, P1585) to induce differentiation into macrophage-like cells. After 24 hours, the medium is replaced with standard growth medium (without PMA) and the cells are incubated for another 48 hours to complete differentiation.

After 72 h of differentiation, the medium is replaced with serum free growth medium, and CDK-inhibiting compounds as well as reference compounds such as positive and negative controls, each dissolved in DMSO were added at concentrations ranging from 0.5 to 5 µM (final concentration of DMSO in the well is 0.1%). Cells are incubated for 60 minutes with compounds prior to stimulation with 100 ng/ml Lps (Sigma, L2630) for another 4-48 hours. Supernatants are collected and assayed immediately for cytokine expression, e.g. for TNFα, IL-6 and IL-1b using commercially available sandwich ELISA assays (eBioscience, Cat. No 88-7346, 88-7066, 88-7010) or kept frozen at 20° C. until evaluation.

Concentrations of TNFα, IL6 and IL1β within the cell culture supernatants are measured by using commercial ELISA Kits (eBioscience) according to the manufacturer's instructions.

Biological Example 5

Carrageenan Assay in Mice

The model of carrageenan induced paw edema is a standard laboratory assay used to predict anti-inflammatory activity and reduction of inflammation-induced pain perception of respective compounds. The following protocol describes one possible way to conduct the experiment.

The basic measurement constitutes in the measurement of edema and mechanical as well as thermal hypersensitivity in response to irritants, such as carrageenan.

Inflammation and resulting inflammatory pain is induced by subcutaneous injection of 25 µl of 1% carrageenan (in saline) into mice hind paw (ipsi-lateral paw). Each group of 10 mice receives administration of a compound according to Formula (I), 30 mg/kg body weight, vehicle ((400 µl) of 2% Hydroxprolylcellulose, 0.25% Lactic acid (85% solution)) and saline (physiol. NaCl) by i.p. injection 30 minutes prior to carrageenan injection. Contra-lateral paws do not receive carrageenan injection.

Paw edema induced by carrageenan injection are detected by increased paw size measured from dorsal to plantar at the metatarsus region of the injected (ipsi-lateral) paws. Sizes of ipsi- and contra-lateral paws serve as surrogate markers for inflammation and are measured at several time points after carrageenan injection: before injection (−1), 2 h (2), 3 h (3), 4 h (4), 5 h (5), 6 h (6), 24 h (24) after injection.

The paw size of all mice may increase, e.g., by 2 to 3 mm (+10%) within the first hour after carrageenan injection, independent of the type of treatment substance injected 30 minutes prior to carrageenan. During the time course, mice which received treatment with a CDK-inhibiting compound prior to carrageenan injection may display a reduction of the edema until 24 hours after carrageenan injection: the increase in paw size could drop e.g. from 10% down to 8%. In contrast, the paw size of the control mice could increase by 30% in average at this time point. After 24 hours post carrageenan injection, the size of all paws treated with carrageenan may increase to reach its maximum at 96 hours after injection.

As a read-out of the carrageenan assay, a Hargreaves Assay may be performed, wherein said assay allows the measuring of thermal sensitivity to radiant heat. The Hargreaves assay (Hargreaves et al., 1988) measures nociceptive sensitivity in a freely moving animal by focusing a radiant heat source on the plantar surface of an animal's hind paw as it stands in a plexiglass chamber. Specifically, the lower side of a paw is exposed to a luminous source, generating a temperature of, e.g. 55° C. Thermal sensitivity is measured as latency between start of exposure and lifting/pulling the exposed paw.

Mice treated with a CDK9 inhibitor as disclosed herein and carrageenan, or with Naproxen and carrageenan, or with solvent and carrageenan, respectively, are subjected to a Hargreaves assay. Mice treated with a CDK inhibitor and carrageenan could display a longer latency, compared to negative control mice. This observation would be indicative for a hypoalgesic effect of the CDK inhibitors as disclosed herein.

Biological Example 6

Carrageenan Assay in Rats

The following depicts one possible way of performing the carrageenan assay in rats.

Said assay detects analgesic/anti-inflammatory activity in rats with inflammatory pain, following the protocol as described by Winter et al. (Proc. Soc. Exp. Biol. Med., 1962, 111, 544-547).

Rats (200-250 g) are injected with a suspension of carrageenan into the lower surface of the right hind paw (0.75 mg per paw in 0.05 ml physiological saline). Two hours later rats are submitted consecutively to tactile and thermal stimulation of both hind paws.

For tactile stimulation, the animal is placed under an inverted acrylic plastic box (18×11.5×13 cm) on a grid floor. The tip of an electronic Von Frey probe (Bioseb, Model 1610) is then applied with increasing force first to the non-inflamed and then the inflamed hind paw and the force required to induce paw-withdrawal is automatically recorded. This procedure is carried out 3 times and the mean force per paw is calculated.

For thermal stimulation, the apparatus consists of individual acrylic plastic boxes (17×11×13 cm) placed upon an elevated glass floor. A rat is placed in the box and left free to habituate for 10 minutes. A mobile infrared radiant source (96±10 mW/cm$^2$) is then focused first under the non-inflamed and then the inflamed hind paw and the paw-withdrawal latency is automatically recorded. In order to prevent tissue damage the heat source is automatically turned off after 45 seconds.

After the behavioral measures, the paw edema is evaluated by measuring the volume of each hind paw using a digital plethysmometer (Letica, Model 7500), which indicates water displacement (in ml) induced by paw immersion.

10 rats are studied per group. The test is performed blind.

The test substance, such as a CDK inhibitor according to Formula (I) as presented herein, will be evaluated at 2 doses (10 and 30 mg/kg), administered p.o. 60 minutes before the test, and compared with a vehicle control group.

Morphine (128 mg/kg p.o.) and acetylsalicylic acid (512 mg/kg p.o.), administered under the same experimental conditions, will be used as reference substances.

The experiment will therefore include 6 groups. Data will be analyzed by comparing treated groups with vehicle control using unpaired Student's t tests.

Rats treated with a CDK9 inhibitor as disclosed herein and carrageenan, or with Naproxen and carrageenan, or with solvent and carrageenan, respectively, are subjected to a Hargreaves assay. Rats treated with a CDK inhibitor and carrageenan should display a longer latency, compared to negative control rats. This observation would be indicative for a hypoalgesic effect of the CDK inhibitors as disclosed herein.

Biological Example 7

In Vivo Lps Assay

The following depicts one possible way of performing the in vivo Lps assay in mice.

For the Lps induced model of septic shock, mice receive an intraperitoneal (i.p.) injection of 30 µg bacterial Lipopolysaccharide (Lps; L2630 SIGMA) in saline. Said Lps-mediated initiation of the inflammatory signaling cascade results in increasing blood serum concentrations of cytokines such as e.g. TNFα, IL-6 and IL1β. Blood can be taken from these animals at defined time points. Thereafter, serum will be separated and the samples can be stored at −80° C. until cytokine concentrations are measured using commercial ELISA assays (Moreira, A. L. et al., Braz J Med Biol Res, 1997, 30, 1199-1207).

It has been recognized that inflammatory mediators such as the cytokines TNFα, IL6 and IL1β can contribute to persistent pain states as well as inflammatory disorders. After being released from immune cells like macrophages in peripheral and microglia in CNS tissues, these mediators seem to play a pivotal role not only in inflammatory and neuropathic pain but also in inflammatory disorders such as rheumatoid arthritis (Marchand, F. et al., Nat Rev Neurosci 2005, 6, 521-532). Thus, inhibition of tumor necrosis factor α (TNFα) represents a relevant target for the treatment of inflammatory diseases as well (Lavagno, L. et al., Eur J Pharmacol 2004, 501, 199-208).

The Lps in vivo assay can be used as a powerful model to address repression of cytokine expression by pharmacological treatments.

Wildtype mice (strain C3HeB/FeJ) (age, sex and weight matched) were injected with 30 µg Lps (SIGMA) intraperitoneally. 90 minutes after Lps administration these animals were anaesthetized with 0.1 ml/10 g bodyweight Ketamine-Rompun (50/20 mg/ml), and blood for serum preparation was taken via cardiac puncture.

Pharmacological treatment groups (n=4) of Lps mice received intraperitoneal (i. p.) injections of CDK-inhibiting compounds or the vehicle (negative control), respectively.

10 or 30 mg/kg (compound per bodyweight) of a CDK inhibitor, dissolved in 20% DMSO, 5% Tween 80, 10% Tris 1 M pH 8, 20% PEG400, 45% PBS was administered as a single dosage 30 minutes prior to Lps stimulation. Vehicle control was administered in the same manner.

90 minutes after Lps stimulation, blood samples were taken from the mice. Previously, the 90 minutes time point had been identified as the peak of TNF alpha expression in this animal model by a time course experiment.

The effect of pharmacological treatment with CDK inhibitors on cytokine levels in Lps mice was analyzed in commercial ELISA assays as described below.

Blood samples (~500 µl/animal) from the Lps animals were incubated on wet ice for 30 minutes after cardiac puncture. Afterwards the samples were centrifuged for 15 minutes at 13.000 rpm. Serum was separated from the clot and stored frozen at −80° C.

Serum concentrations of TNF alpha and IL6 within the samples were measured by using commercial ELISA Kits (Natutec) according to the manufacturer's instructions.

Biological Example 8

Spared Nerve Injury (SNI)

Model of Chronic Neuropathic Pain

The following depicts one possible way of performing the Spared nerve injury (SNI)—Model of chronic neuropathic pain assay in mice.

Several animal models for the analysis of inflammatory and neuropathic pain are known. Said models share the common feature that after e.g., induction of a nerve lesion (e.g., spared nerve injury, SNI) or after exposing experimental animals to a noxious stimulus (e.g., injection of formalin or carrageenan), the signs of pain as induced by said interventions are measured by quantifiable behavioral components such as, e.g., paw withdrawal threshold to mechanical stimulation with von Frey hairs (or to thermal stimulation using a laser source or licking behaviour). These reactions are interpreted as being equivalent to mechanical and thermal allodynia (hypersensitivity to mechanical stimuli) or hyperalgesia in humans.

The spared nerve injury model (SNI model, as developed by Decosterd and Woolf (Decosterd, I., Woolf, C. J., Pain 2000, 87, 149-158), is characterized by the induction of clinically relevant nerve lesions and after surgical intervention, subsequent behavioral experiments (e.g., von Frey Assay). Said model constitutes a common nerve injury model which consists of ligation and section of two branches of the sciatic nerve (namely tibial and common peroneal nerves) leaving the sural nerve intact. The SNI model results in early (less than 24 hours), prolonged and substantial changes in mechanical and cold sensitivity that closely mimic the features of clinical neuropathic pain. Animals with these types of nerve injury have been shown to develop abnormal pain sensations and hypersensitivity to mechanical stimuli (allodynia) similar to those reported by neuropathic pain patients.

Alternatively, the formalin assay in mice is a valid and reliable behavioral model of nociception in inflammatory and neuropathic pain. It is sensitive to various classes of analgesic drugs (Hunskaar, S., Hole, K., Pain 1987, 30, 103-114). The noxious stimulus consists of an injection of 10 µl diluted formalin (2% in saline) under the skin of the dorsal surface of the left hind paw (subcutaneous or interplantar into the left hind paw). The response is licking and flinching of the injected paw.

For the carrageenan assay a subcutaneous injection of 25 µl of 1% carrageenan (in saline) into a single hind paw (ipsilateral paw) of mice is applied. Subsequent inflammation results in long lasting swelling and hypersensitivity (against mechanical and thermal stimuli) of the paw. The carrageenan assay is a standard laboratory assay used to predict anti-inflammatory activity of test compounds. Paw edema measurements and Hargreaves Assay (withdrawal of paws due to thermal stimulation via a light source) are used for read out.

Regarding the present invention, the effect of administration of cyclin-dependent kinase (CDK)-inhibiting compounds according to Formula (I) on the development of inflammatory and neuropathic pain is assayed in a SNI model, in a carrageenan and in a formalin assay. The experimental procedure and results are described in detail below.

Spared Nerve Injury (SNI)—Model of Chronic Neuropathic Pain

As outlined above, the spared nerve injury (SNI) model involves a lesion of two of the three terminal branches of the sciatic nerve (tibial and common peroneal nerves) of experimental animals, leaving the sural nerve intact. SNI results in mechanical and thermal allodynia in the non-injured sural nerve skin territory (Decosterd, I., Woolf, C. J., Pain 2000, 87, 149-158; Tsujino, H. et al., Mol. Cel. Neurosci. 2000, 15, 170-182).

Wildtype mice (strain C3HeB/FeJ) (age, sex and weight matched) were anesthetized with Hypnorm (0.315 mg/ml fentanyl citrate+10 mg/ml fluanisone; Janssen)/Hypnovel (5 mg/ml midazolam; Roche Applied Sciences)/water at a ratio of 1:1:2 at 4 µl/g prior to surgical preparation.

Subsequently, an incision was made under aseptic precautions in the ipsi-lateral right hind leg of all mice just above the level of the knee, exposing the three terminal branches of the sciatic nerve: the common peroneal, tibial, and sural nerves. The common peroneal and tibial nerves were ligated tightly with 7/0 silk and sectioned distal to the ligation removing ≈2 mm of distal nerve stump. The sural branch remained untouched during the procedure (denoted herein "SNI ipsi"). The overlying muscle and skin was sutured, and the animals were allowed to recover and to permit wound healing. In the same mice the sciatic nerve branches of the contra-lateral left hind leg were exposed but not lesioned (denoted herein "SNI contra-lateral"). Mice that underwent spared nerve injury are hereinafter denoted "SNI mice".

After recovery from surgery and wound healing, SNI mice received per oral (p.o.) injections of CDK-inhibiting compounds.

30 mg/kg of a CDK inhibitor, dissolved in 400 µl of 2% Hydroxprolylcellulose, 0.25% Lactic acid (85% solution) was administered via per oral application 30 minutes prior to von Frey measurements (mechanical allodynia). As a negative control, the same amount (400l) of 2% Hydroxprolylcellulose, 0.25% Lactic acid (85% solution) vehicle was administered by a single per oral application 30 minutes prior to von Frey measurements.

Injection of inhibitor or vehicle, and subsequent measurements of paw withdrawal threshold to mechanical stimulation in von Frey assays were performed at day 107 post SNI. Reflex nociceptive responses to mechanical stimulation were measured in a von Frey assay 30 minutes after each injection.

The effect of administration of CDK inhibitors to SNI mice on the development of mechanical allodynia was analyzed in a von Frey assay, as described below.

Mice that underwent SNI and subsequent administration of the compounds of the present invention were tested for signs of mechanical allodynia post nerve injury and post administration in a von Frey assay (Decosterd, I., Woolft C. J., Pain 2000, 87, 149-158). This assay determines the mechanical threshold upon which a stimulus, which normally is not painful, is recognized by an animal as uncomfortable or painful. SNI ipsi and SNI contra baselines, respectively, were established.

Mechanical thresholds of SNI mice were quantified using the up-down method based on Chaplan, S. R. et al. (Journal of Neuroscience Methods, 1994, 53, 55-63) and Malmberg, A. B. and Basbaum, A. I. (Pain 1998, 76, 215-222).

Mice were placed in plexiglass cylinders of about 9.5 cm in diameter, 14 cm high with four vent holes toward the top and a plexiglass lid. The cylinders were placed on an elevated mesh surface (7×7 mm squares). Prior to the day of testing, the mice were acclimated to the testing cylinders for 1-2 hours. On the day of testing the mice were acclimated to the cylinders for about an hour, wherein the acclimation time depends on factors such as the strain of the mouse and the number of times they have been tested previously. In general, testing may begin once the mice are calm and stop exploring the new environment.

For testing mice, filaments 2.44, 2.83, 3.22, 3.61, 3.84, 4.08, and 4.31 (force range=0.04 to 2.0 g) were used. The 3.61 mN filament was applied first. Said filament was gently applied to the plantar surface of one paw, allowed to bend, and held in position for 2-4 seconds. Whenever a positive response to the stimulus (flexion reaction) occurred the next weaker von Frey hair was applied; whenever a negative response (no reaction) occurred the next stronger force was applied. The test was continued until the response to 4 more stimuli after the first change in response had been obtained. The highest force tested was 4.31. The cut-off threshold was 2 g.

The series of scores (i.e., "flexion reaction" and "no reaction") and the force of the last filament applied were used to determine the mechanical threshold as described in Chaplan, S. R. et al. (Journal of Neuroscience Methods, 1994, 53, 55-63). The threshold determined is that to which the animal would be expected to respond to 50% of the time. Mice were sacrificed after von Frey measurements were accomplished.

Biological Example 9

Formalin Assay

Model of Inflammatory Processes/Inflammatory and Chronic Neuropathic Pain

The following depicts one possible way of performing the Formalin Assay, a model of inflammatory processes as well as inflammatory and chronic neuropathic pain assay in mice.

The formalin assay in mice is a valid and reliable behavioral model of nociception and is sensitive to various classes of analgesic drugs (Hunskaar, S., Hole, K., Pain 1987, 30, 103-114). The noxious stimulus is an injection of 10 µl diluted formalin (2% in saline) subcutaneous or intraplantar into the left hind paw. The response is licking and flinching of the injected paw. The response shows two phases, which reflect different parts of the inflammatory process (Abbott, F. V. et al., Pain 1995, 60, 91-102), an early/acute phase 0-5 minutes post-injection, and a late/chronic phase 5-30 minutes post-injection. The following protocol describes one possible way to conduct the experiment:

Age, sex and weight matched wildtype mice (C3HeB/FeJ) are used in this assay. Prior to formalin injection the animals are randomly subdivided into experimental groups of 10 animals each. Thirty minutes prior to formalin injection, a suitable dose of a CDK inhibitor dissolved in (400 µl) of 2% Hydroxprolylcellulose, 0.25% Lactic acid (85% solution) can be administered by i.p. injection.

For formalin injection the mouse is held with a paper towel, in order to avoid disturbance of the injection by movements. The injected hind paw is held between thumb and forefinger and 10 µl of Formalin (2%) is injected subcutaneously (s.c.) between the two front tori into the plantar hind paw using a Hamilton syringe. The behavior of the formalin- and inhibitor-treated mice is analyzed as described below.

The behaviour of the formalin-treated mice, i.e. licking and flinching, is monitored by an automated tracking system (Ethovision 3.0 Color Pro, Noldus, Wageningen, Netherlands) over a defined period of time: measurement is initiated 5 minutes after formalin injection and terminated 30 minutes after formalin injection. This time frame covers phase II of formalin-induced nociception (pain), which is hyperalgesia.

Two different fluorescent dyes are used for topically marking the injected hind paw (yellow dye) (Lumogenyellow; BASF Pigment, Cologne, Germany) and the contralateral paw (blue dye) (Lumogenviolet; Kremer Pigmente, Aichstetten, Germany) respectively. To determine licking behaviour, mice are monitored with a CCD camera. After monitoring and recording, the video is analyzed using the EthoVision software (Ethovision 3.0 Color Pro, Noldus, Wageningen, Netherlands) or by manual analysis. Fluorescent dot sizes and fluorescence intensities were measured and reduction of fluorescent dot size through licking and biting was calculated. The overall licking time intensity was automatically calculated by comparison of dot size reduction of treated versus untreated paws.

As another variant of assay read out, the licking behaviour of the individual animals was tracked manually based on video files. Licking times were recorded over 30 minutes after formalin injection and subdivided for three different licking zones (dorsum, plantar, toes). Overall licking times can be calculated for each animal as well as each experimental group and be used as a parameter for determination of compound efficacy.

As a result it was found that mice receiving vehicle treatment prior to formalin injection (negative control) displayed a prolonged licking time and a significant reduction of fluorescent dot size at the formalin-treated paw.

In contrast, a reduction in licking time and in consequence no significant reduction of fluorescent dot size of the formalin-treated paw could be observed in test compound/formalin-treated mice. The same effect, i.e. a reduction in licking time and a minor change in fluorescent dot size, was observed in control mice treated with Ikappa kinase inhibitor.

This observation is indicative for reduced inflammatory/chronic inflammatory pain perception in CDK inhibitor-treated mice and for a hypoalgesic effect of the tested compound.

The invention claimed is:

1. A method for the treatment of pain, the method comprising administering to a subject in need of such treatment an effective amount of a compound of Formula (I):

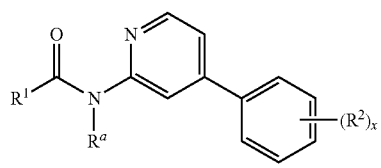

Formula (I)

or a pharmaceutically acceptable salt, polymorph, tautomer and stereoisomer thereof wherein:
$R^a$ is H or methyl;
$R^1$ is selected from the group consisting of:
carbocyclic or —$C_{1-6}$ alkyl-carbocyclic, wherein the carbocyclic group is cyclohexyl or cyclopentyl;
heterocyclic or —$C_{1-6}$ alkyl-heterocyclic group, wherein the heterocyclic group is piperidine, piperazine, morpholine or pyrrolidine;
aryl or alkyl-aryl;
heteroaryl or —$C_{1-6}$ alkyl-heteroaryl, wherein the heteroaryl group is pyridine, thiazole or thiophene;
wherein any of the aforesaid carbocyclic, heterocyclic, aryl or heteroaryl groups may optionally be substituted by one or more groups independently selected from:
halo, OH, $NH_2$ and, for carbocyclic and heterocyclic groups, =O; or
$C_{1-4}$ alkyl, —O($C_{1-4}$ alkyl), —NH($C_{1-4}$ alkyl), —NHC(O)($C_{1-4}$ alkyl), —S($C_{1-4}$ alkyl), —SO($C_{1-4}$ alkyl), —$SO_2$($C_{1-4}$ alkyl) or —$SO_2$NH($C_{1-4}$ alkyl) any of which may be further substituted with halo or OH; or
$R^3$, —$C_{1-4}$ alkyl-$R^3$, $OR^3$, $NHR^3$, —$NHC_{1-4}$ alkyl-$R^3$, —$OC_{1-4}$ alkyl-$R^3$, $SR^3$, $SOR^3$ or $SO_2R^3$;
wherein $R^3$ is an aryl, heteroaryl, carbocyclic or heterocyclic group any of which may be substituted with one or more halo, $C_{1-4}$ alkyl, —O($C_{1-4}$ alkyl), $NH_2$, —NH($C_{1-4}$ alkyl), —C(O)($C_{1-4}$ alkyl), —NHC(O)($C_{1-4}$ alkyl) groups, any of which alkyl groups may be substituted with halo or OH;
each $R^2$ is independently halo, OH, $NH_2$; or
$C_{1-4}$ alkyl, —O($C_{1-4}$ alkyl), —NH($C_{1-4}$ alkyl), —C(O)($C_{1-4}$ alkyl), any of which may be further substituted with halo or OH; or
$R^4$, —$C_{1-4}$ alkyl-$R^4$, $OR^4$, $NHR^4$, alkyl-$R^4$, —$OC_{1-4}$ alkyl-$R^4$, $SR^4$, $SOR^4$ or $SO_2R^4$;
wherein $R^4$ is an aryl, heteroaryl, carbocyclic or heterocyclic group any of which may be further substituted with one or more halo, OH, $C_{14}$ alkyl, —O($C_{1-4}$ alkyl), $NH_2$, —NH($C_{1-4}$ alkyl), —C(O)($C_{1-4}$ alkyl), —NHC(O)($C_{1-4}$ alkyl) groups, any of which alkyl groups may be substituted with halo or OH; and
x is 0-4.

2. The method of claim 1, wherein in Formula (I) $R^a$ is H.

3. The method of claim 1 wherein in Formula (I) x is 2.

4. The method of claim 1 wherein in Formula (I) $R^2$ is halo, $C_{1-4}$ alkyl, $C_{1-4}$ haloalkyl, $C_{1-4}$ alkoxy or $C_{1-4}$ haloalkoxy.

5. The method of claim 4, wherein in Formula (I) there are two $R^2$ groups, one of which is halo and the other of which is methoxy or halomethoxy.

6. The method of claim 1 wherein in Formula (I) $R^1$ is $C_5$ or $C_6$ carbocyclic, $C_5$ or $C_6$ heterocyclic, —$C_{1-3}$ alkyl-phenyl, —$C_{1-3}$ alkyl($C_5$ or $C_6$ heteroaryl), —$C_{1-3}$ alkyl($C_5$ or $C_6$ carbocyclic), —$C_{1-3}$ alkyl($C_5$ or $C_6$ heterocyclic), phenyl or $C_5$ or $C_6$ heteroaryl, wherein any of the aforesaid cyclic groups may optionally be substituted as described in claim 1.

7. The method of claim 1 wherein in Formula (I) $R^1$ is cyclohexyl, cyclopentyl, —$C_{1-3}$ alkyl(cyclohexyl), —$C_{1-3}$ alkyl(cyclopentyl); or $R^1$ is piperidine, piperazine, morpholine and pyrrolidine, —$C_{1-3}$ alkyl(piperidine), —$C_{1-3}$ alkyl(piperazine), —$C_{1-3}$ alkyl(morpholine), —$C_{1-3}$ alkyl(pyrrolidine); or $R^1$ is phenyl or —$C_{1-3}$ alkyl-phenyl; or $R^1$ is pyridine, thiazole, thiophene, —$C_{1-3}$ alkyl(pyridine), —$C_{1-3}$ alkyl(thiazole) or —$C_{1-3}$ alkyl(thiophene), wherein any of the aforesaid cyclic groups may optionally be substituted as described in claim 1.

8. The method of claim 1 wherein in Formula (I) $R^1$ is a —$C_{1-3}$ alkyl(carbocyclic), —$C_{1-3}$ alkyl(heterocyclic), —$C_{1-3}$ alkyl(aryl) or —$C_{1-3}$ alkyl(heteroaryl) group, and the —$C_{1-3}$ alkyl linker is:
—$CH_2$—;
—CH($CH_3$)—;
—$CH_2$CH($CH_3$)—;
—CH($CH_3$)$CH_2$—; or
—$CH_2CH_2$—.

9. The method of claim 1, wherein in Formula (I) $R^1$ is unsubstituted or is substituted, with one or more groups chosen from:

halo, OH, $NH_2$ and, for carbocyclic and heterocyclic groups, =O; or $C_{1-4}$ alkyl, —O($C_{1-4}$ alkyl), —NH($C_{1-4}$ alkyl), —NHC(O) ($C_{1-4}$ alkyl), any of which may be further substituted with halo or OH; or $R^3$, —$C_{1-4}$ alkyl-$R^3$, $OR^3$, $NHR^3$, —$NHC_{1-4}$ alkyl-$R^3$, —$OC_{1-4}$ alkyl-$R^3$;

wherein $R^3$ is an aryl, heteroaryl, carbocyclic or heterocyclic group any of which may be substituted with one or more halo, OH, $NH_2$ or $C_{1-4}$ alkyl or —O($C_{1-4}$ alkyl) groups, either of which alkyl groups may be substituted with halo.

10. The method of claim 9, wherein in Formula (I) $R^1$ is unsubstituted or is substituted with one or more groups chosen from $NH_2$, methyl, ethyl, methoxy, ethoxy, chloro, fluoro, trifluoromethyl, trifluoromethoxy, =O (for carbocyclic and heterocyclic groups), NHC(O)Me, $R^3$, $NHR^3$, and $NHCH_2R^3$;

wherein $R^3$ is an aryl, heteroaryl, carbocyclic or heterocyclic group any of which may be substituted with one or more halo, OH, $NH_2$ or $C_{1-4}$ alkyl or —O($C_{1-4}$ alkyl) groups, either of which alkyl groups may be substituted with halo.

11. The method of claim 9, wherein in Formula (I) $R^3$ is piperidine, 4-methylpiperidine, piperazine, 4-methylpiperazine, thienyl, thien-2-yl, thiazolyl, thiazol-2-yl, pyridinyl, pyridin-2-yl, pyridine-3-yl, pyridine-4-yl, and phenyl.

12. The method of claim 1 wherein the compound is selected from the group consisting of:

N-(4-(4-Fluoro-2-methoxyphenyl)pyridin-2-yl)cyclohexanecarboxamide;
2-Cyclohexyl-N-(4-(4-fluoro-2-methoxyphenyl)pyridin-2-yl)acetamide;
N-(4-(4-Fluoro-2-methoxyphenyl)pyridin-2-yl)piperidine-4-carboxamide;
4-Amino-N-(4-(4-fluoro-2-methoxyphenyl)pyridin-2-yl)cyclohexane-carboxamide;
N-(4-(4-Fluoro-2-methoxyphenyl)pyridin-2-yl)-5-oxopyrrolidine-3-carboxamide;
N-(4-(4-Fluoro-2-methoxyphenyl)pyridin-2-yl)-2-(4-methoxyphenyl)-acetamide;
N-(4-(4-Fluoro-2-methoxyphenyl)pyridin-2-yl)-2-phenylacetamide;
N-(4-(4-Fluoro-2-methoxyphenyl)pyridin-2-yl)-2-(pyridin-4-yl)acetamide;
N-(4-(4-Fluoro-2-methoxyphenyl)pyridin-2-yl)-2-(thiophen-2-yl)acetamide;
(2S)-N-(4-(5-Fluoro-2-methoxyphenyl)pyridin-2-yl)-2-phenylpropanamide;
(2S)-N-(4-(4-Fluoro-2-methoxyphenyl)pyridin-2-yl)-2-(4-methoxyphenyl)-propanamide;
isomers of N-(4-(4-Fluoro-2-methoxyphenyl)pyridin-2-yl)-2-(pyridin-3-yl)propanamide;
N-(4-(4-Fluoro-2-methoxyphenyl)pyridin-2-yl)-2-(6-methoxypyridin-3-yl)acetamide;
isomers of N-(4-(4-Fluoro-2-methoxyphenyl)pyridin-2-yl)-2-(pyridin-4-yl)propanamide;
isomers of (2R)-N-(4-(5-Fluoro-2-methoxyphenyl)pyridin-2-yl)-2-(thiophen-2-yl)propanamide;
2-(2-Chloropyridin-4-yl)-N-(4-(4-fluoro-2-methoxyphenyl)pyridin-2-yl)acetamide;
N-(4-(4-Fluoro-2-methoxyphenyl)pyridin-2-yl)-2-(4-(4-methylpiperazin-1-yl)phenyl)acetamide;
N-(4-(4-Fluoro-2-methoxyphenyl)pyridin-2-yl)-3-(pyridin-4-yl)butanamide;
N-(4-(4-Fluoro-2-methoxyphenyppyridin-2-yl)-2-((pyridin-4-yl)methyl)-propanamide;
N-(4-(4-Fluoro-2-methoxyphenyl)pyridin-2-yl)-3-(pyridin-3-yl)butanamide;
N-(4-(4-Fluoro-2-methoxyphenyl)pyridin-2-yl)-2-((pyridin-3-yl)methyl)-propanamide;
trans-3-Acetamido-N-(4-(4-fluoro-2-methoxyphenyl)-pyridin-2-yl)cyclohexanecarboxamide;
N-(4-(4-Fluoro-2-methoxyphenyl)pyridin-2-yl)-2-(4-(4-methylpiperazin-l-yl)phenyl)propanamide;
2-(4-(4-Methylpiperazin-1-yObenzyl)-N-(4-(4-fluoro-2-methoxyphenyl)-pyridin-2-yl)propanamide;
N-(4-(4-Fluoro-2-methoxyphenyl)pyridin-2-yl)-3-(4-(4-methylpiperazin-l-yl)phenyl)butanamide;
N-(4-(4-Fluoro-2-methoxyphenyl)pyridin-2-yl)-4-(pyridin-2-ylamino)-cis-cyclohexanecarboxamide;
N-(4-(4-Fluoro-2-methoxyphenyl)pyridin-2-yl)-2-(2-(4-methylpiperazin-l-yl)pyridin-4-yl)acetamide;
cis-N-(4-(4-Fluoro-2-methoxyphenyl)pyridin-2-yl)-4-(pyridin-4-ylamino)-cyclohexanecarboxamide;
(1R,3S)-3-Acetamido-N-(4-(4-fluoro-2-methoxyphenyl)pyridin-2-yl)cyclo-pentanecarboxamide;
cis-N-(4-(4-Fluoro-2-methoxyphenyppyridin-2-yl)-4-(thiazol-2-ylamino)-cyclohexanecarboxamide;
cis-N-(4-(4-Fluoro-2-methoxyphenyl)pyridin-2-yl)-4-(phenylamino)-cyclohexanecarboxamide;
(1R,3S)-3-(Benzylamino)-N-(4-(4-fluoro-2-methoxyphenyl)pyridin-2-yl)cyclopentanecarboxamide;
cis-4-(Benzylamino)-N-(4-(4-fluoro-2-methoxyphenyl)pyridin-2-yl)cyclo-hexanecarboxamide;
(1R,3S)-N-(4-(4-Fluoro-2-methoxyphenyl)pyridin-2-yl)-3-(phenylamino)-cyclopentanecarboxamide;
(1R,3S)-3-Acetamido-N-(4-(4-fluoro-2-methoxyphenyl)pyridin-2-yl)cyclohexanecarboxamide;
(1S,3R)-3-Acetamido-N-(4-(4-fluoro-2-methoxyphenyl)pyridin-2-yl)cyclopentanecarboxamide; or a pharmaceutically acceptable salt, polymorph, tautomer and stereoisomer thereof.

13. The method of claim 1 wherein the compound is cis-3-acetamido-N-(4-(4-fluoro-2-methoxyphenyl)pyridin-2-yl)cyclo-hexanecarboxamide.

* * * * *

UNITED STATES PATENT AND TRADEMARK OFFICE
CERTIFICATE OF CORRECTION

PATENT NO. : 9,067,888 B2
APPLICATION NO. : 14/011057
DATED : June 30, 2015
INVENTOR(S) : Lutz Zeitlmann et al.

It is certified that error appears in the above-identified patent and that said Letters Patent is hereby corrected as shown below:

In the Specification

Column 2,
Line 33, "1312-4327" should be -- 1312-1327 --.
Line 44, "MK" should be -- CDK --.

Column 3,
Line 21, "549-57" should be -- S49-57 --.
Line 34, "14334439" should be -- 1433-1439 --.
Line 36, "15584570" should be -- 1558-1570 --.
Line 43, "12404252" should be -- 1240-1252 --.

Column 4,
Line 18, delete "Rx".
Line 26, "TNF" should be -- TNFα --.
Line 39, "Chose" should be -- Ghose --.

Column 5,
Line 7, after "e.g. a" insert -- $C_{2-4}$ --.
Lines 26-27, "cyclooetenyl" should be -- cyclooctenyl --.

Column 6,
Line 50, "2-(4-ethyl-phenyl)-ethyl-yl" should be -- 2-(4-ethyl-phenyl)-eth-1-yl --.
Line 51, after "methyl-" (first occurrence), insert a -- , -- and a space.
Line 55, after "ethyl-" (first occurrence), insert a -- , -- and a space.
Line 60, after "methyl-", insert a -- , -- and a space.
Line 67, after "methyl-,", insert -- indan-1-on-2-yl-methyl-, indan-1-on-2-yl- --.

Signed and Sealed this
Twelfth Day of April, 2016

Michelle K. Lee
*Director of the United States Patent and Trademark Office*

CERTIFICATE OF CORRECTION (continued)
U.S. Pat. No. 9,067,888 B2

Column 7,
Line 2, after "methyl" insert a -- - -- and a -- , --.
Line 10, "pyrrol-4-pyridino-methyl-," should be -- pyrrol-1-ethyl-, 4-pyridino-methyl-, --.
Line 24, "$C_{2-4}$alkylene" should be -- $C_{1-4}$ alkylene --.
Line 55, "(O-di-p-toluoyl-L-tartaric" should be -- (+)-di-p-toluoyl-L-tartaric --.

Column 8,
Line 23, after "maleic," insert -- malic, --.
Line 63, "ed. 11." should be -- ed. H. --.

Column 9,
Line 25, "CDSK" should be -- CDK --.

Column 31,
Line 1, "cone." should be -- conc. --.

Column 35,
Line 29, "40 mmol" should be -- 40 μmol --.

Column 48,
Line 51, "cone." should be -- conc. --.

Column 49,
Line 38, "pH-6" should be -- pH~6 --.

Column 51,
Line 11, "45 mol" should be -- 45 μmol --.
Line 12, "38 mmol" should be -- 38 μmol --.
Line 17, "137 mol" should be -- 137 μmol --.

Column 53,
Line 24, "cone." should be -- conc. --.

Column 59,
Line 13, "50 mol" should be -- 50 μmol --.
Line 23, "DMSO-d" should be -- DMSO-$d_6$ --.
Line 24, "(d, 1H.02)" should be -- (d, 1H) --.

Column 60,
Line 9, "36 mol" should be -- 36 μmol --.
Line 10, "18 mmol" should be -- 18 μmol --.

Column 62,
Line 58, "49 mol" should be -- 49 μmol --.

Column 63,
Line 66, "50 mol" should be -- 50 μmol --.

Column 66,
Line 33, "(s, 1)" should be -- (s, 1H) --.

Column 68,
Line 53, "(d, 1)" should be -- (d, 1H) --.

Column 70,
Line 35, "100%" (second occurrence) should be -- 100μl --.
Line 52, after "10%" delete the "/".

Column 71,
Line 19, "PEG2000" should be -- PEG20000 --.
Line 28, "1 CDK4/CycD1" should be -- 2 CDK4/CycD1 --.

Column 84,
Table 1 (continued), heading of last column, "CDK9" should be -- CDK5 --.
Line 50, "CDKS/p35NCK" should be -- CDK5/p35NCK --.

In the Claims

Column 94,
Line 1, "alkyl-aryl" should be -- -$C_{1-6}$ alkyl-aryl --.
Line 31, "$C_{14}$ alkyl" should be -- $C_{1-4}$ alkyl --.